(12) United States Patent
Kane, Jr. et al.

(10) Patent No.: US 11,530,216 B2
(45) Date of Patent: Dec. 20, 2022

(54) DEUTERATED COLONY STIMULATING FACTOR-1 RECEPTOR (CSF-1R) INHIBITORS

(71) Applicant: Genzyme Corporation, Cambridge, MA (US)

(72) Inventors: John L. Kane, Jr., Stow, MA (US); Nellwyn A. Hagan, Canton, MA (US); Maria A. Fitzgerald, Concord, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 17/669,950

(22) Filed: Feb. 11, 2022

(65) Prior Publication Data
US 2022/0204504 A1 Jun. 30, 2022

Related U.S. Application Data

(63) Continuation of application No. PCT/US2021/064831, filed on Dec. 22, 2021.

(60) Provisional application No. 63/129,939, filed on Dec. 23, 2020, provisional application No. 63/226,549, filed on Jul. 28, 2021.

(51) Int. Cl.
*C07D 471/04* (2006.01)
*A61P 37/06* (2006.01)

(52) U.S. Cl.
CPC ............ *C07D 471/04* (2013.01); *A61P 37/06* (2018.01); *C07B 2200/05* (2013.01)

(58) Field of Classification Search
CPC .............................. A61P 37/06; C07D 471/04
USPC ......................................................... 514/303
See application file for complete search history.

(56) References Cited

U.S. PATENT DOCUMENTS

| | | | |
|---|---|---|---|
| 4,612,323 A | 9/1986 | Kisida et al. | |
| 5,187,159 A | 2/1993 | Greenlee et al. | |
| 6,060,480 A * | 5/2000 | Nakamura | C07D 471/04 514/263.22 |
| 6,130,333 A | 10/2000 | Huang et al. | |
| 6,348,474 B1 * | 2/2002 | Kayakiri | C07D 241/52 546/112 |
| 11,274,108 B2 * | 3/2022 | Kane, Jr. | C07D 405/04 |
| 2003/0114468 A1 | 6/2003 | Wilde et al. | |
| 2003/0176400 A1 | 9/2003 | Torisu et al. | |
| 2005/0004097 A1 | 1/2005 | Torisu et al. | |
| 2005/0107343 A1 | 5/2005 | Kasibhatla et al. | |
| 2006/0025383 A1 | 2/2006 | Wishart et al. | |
| 2006/0116402 A1 | 6/2006 | Crew et al. | |
| 2006/0235222 A1 | 10/2006 | Bell et al. | |
| 2007/0043068 A1 | 2/2007 | Arnold et al. | |
| 2008/0013095 A1 | 1/2008 | Tai et al. | |
| 2008/0108648 A1 | 5/2008 | Alcouffe et al. | |
| 2008/0221148 A1 | 9/2008 | Ibrahim et al. | |
| 2009/0093516 A1 | 4/2009 | Li et al. | |
| 2009/0274698 A1 | 11/2009 | Bhagwat et al. | |
| 2009/0286782 A1 | 11/2009 | Ibrahim et al. | |
| 2010/0324011 A1 | 12/2010 | Bian et al. | |
| 2011/0166174 A1 | 7/2011 | Zhang et al. | |
| 2011/0281865 A1 | 11/2011 | Muthuppalaniappan et al. | |
| 2012/0129829 A1 | 5/2012 | Sinha et al. | |
| 2012/0252778 A1 | 10/2012 | Miltz et al. | |
| 2013/0018049 A1 | 1/2013 | Rosa et al. | |
| 2013/0196967 A1 | 8/2013 | Bartolozzi et al. | |
| 2014/0155398 A1 | 6/2014 | Verma et al. | |
| 2014/0309227 A1 | 10/2014 | Bungard et al. | |
| 2019/0016707 A1 * | 1/2019 | Kane, Jr. | C07D 471/04 |

FOREIGN PATENT DOCUMENTS

| | | | |
|---|---|---|---|
| CN | 101558070 A | | 10/2009 |
| CN | 104321322 A | | 1/2015 |
| CN | 110526916 | * | 3/2019 |
| EA | 7157 B1 | | 8/2006 |
| EP | 0186190 A2 | | 7/1986 |
| EP | 569013 | * | 6/1993 |
| EP | 0786460 A2 | | 7/1997 |
| EP | 812841 | * | 12/1997 |
| EP | 0995742 A1 | | 4/2000 |
| FR | 2693197 | * | 3/1992 |
| FR | 2693197 A1 | | 1/1994 |
| JP | 07138259 | * | 5/1995 |
| JP | H09202774 A | | 8/1997 |
| JP | H101471 A | | 1/1998 |

(Continued)

OTHER PUBLICATIONS

Denny; Expert Opinion on Therapeutic Patents, 2021, 31, 107-117. Published online Oct. 28, 2020. DOI: 10.1080/13543776.2021. 1839414 (Year: 2020).*

(Continued)

*Primary Examiner* — Daniel R Carcanague
(74) *Attorney, Agent, or Firm* — McNeill Baur, PLLC

(57) ABSTRACT

Disclosed herein are deuterated compounds of the formula

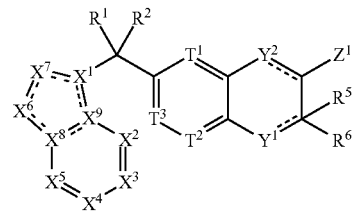

which are useful as colony stimulating factor-1 receptor inhibitors ("CSF-1R inhibitors").

28 Claims, 26 Drawing Sheets

(56) References Cited

FOREIGN PATENT DOCUMENTS

| | | | |
|---|---|---|---|
| JP | 2001039874 | * | 7/1999 |
| JP | 2002507996 | A | 3/2002 |
| JP | 2007500253 | A | 1/2007 |
| JP | 2007505933 | A | 3/2007 |
| JP | 2007520559 | A | 7/2007 |
| JP | 2008503473 | A | 2/2008 |
| JP | 2008521903 | A | 6/2008 |
| JP | 2008533111 | A | 8/2008 |
| JP | 2008545652 | A | 12/2008 |
| JP | 2008546797 | A | 12/2008 |
| JP | 2010510321 | A | 4/2010 |
| JP | 2010514695 | A | 5/2010 |
| JP | 2010532756 | A | 10/2010 |
| JP | 2010540643 | A | 12/2010 |
| JP | 2012524800 | A | 10/2012 |
| JP | 2013529207 | A | 7/2013 |
| JP | 2013543892 | A | 12/2013 |
| JP | 2014514293 | A | 6/2014 |
| JP | 2014515368 | A | 6/2014 |
| JP | 2014522858 | A | 9/2014 |
| JP | 2015511629 | A | 4/2015 |
| NO | 9900372 | A1 | 1/1999 |
| WO | 9400450 | A1 | 1/1994 |
| WO | 9413676 | A1 | 6/1994 |
| WO | 1994014434 | A1 | 7/1994 |
| WO | 9808514 | A1 | 3/1998 |
| WO | 9901454 | A1 | 1/1999 |
| WO | 2001066520 | A1 | 9/2001 |
| WO | 200250062 | A2 | 6/2002 |
| WO | 02092575 | A1 | 11/2002 |
| WO | 03092595 | A2 | 11/2003 |
| WO | 2004067529 | A1 | 8/2004 |
| WO | 2005028434 | A2 | 3/2005 |
| WO | 2005028448 | A1 | 3/2005 |
| WO | 2005074603 | A2 | 8/2005 |
| WO | 2006009755 | A2 | 1/2006 |
| WO | 2006009797 | A1 | 1/2006 |
| WO | 2006025715 | A1 | 3/2006 |
| WO | 2006060381 | A2 | 6/2006 |
| WO | 2006097625 | A1 | 9/2006 |
| WO | 2007002325 | A1 | 1/2007 |
| WO | 2007002433 | A1 | 1/2007 |
| WO | 2007013896 | A2 | 2/2007 |
| WO | 2007132308 | A1 | 11/2007 |
| WO | 2008008539 | A2 | 1/2008 |
| WO | 2008051805 | A2 | 5/2008 |
| WO | 2008063888 | A2 | 5/2008 |
| WO | 2008064255 | A2 | 5/2008 |
| WO | 2008064265 | A2 | 5/2008 |
| WO | 2008080001 | A2 | 7/2008 |
| WO | 2008130951 | A1 | 10/2008 |
| WO | 2009008992 | A2 | 1/2009 |
| WO | 2009045753 | A1 | 4/2009 |
| WO | 2009062118 | A2 | 5/2009 |
| WO | 2010124082 | A1 | 10/2010 |
| WO | 2011145035 | A1 | 11/2011 |
| WO | 2011156632 | A2 | 12/2011 |
| WO | 2012071184 | A1 | 5/2012 |
| WO | 2012107500 | A1 | 8/2012 |
| WO | 2012131633 | A1 | 10/2012 |
| WO | 2012160464 | A1 | 11/2012 |
| WO | 2013012649 | A1 | 1/2013 |
| WO | 2013056070 | A2 | 4/2013 |
| WO | 2013142427 | A1 | 9/2013 |
| WO | 2013144737 | A3 | 12/2013 |
| WO | 2014081820 | A1 | 5/2014 |
| WO | 2015089139 | A1 | 6/2015 |
| WO | 2015103137 | A1 | 7/2015 |
| WO | 2015168269 | A1 | 11/2015 |
| WO | 2016087586 | A1 | 6/2016 |
| WO | 2017015267 | A1 | 1/2017 |

OTHER PUBLICATIONS

Hagan; Cell Death and Disease 2020, 11, 904. Published: Oct. 23, 2020. DOI:10.1038/s41419-020-03084-7 (Year: 2020).*
Pirali; J. Med. Chem. 2019, 62, 5276-5297. DOI: 10.1021/acs.jmedchem.8b01808 (Year: 2019).*
Zhan; Chem. Res. Toxicol. 2018, 31, 11, 1213-1218. https://doi.org/10.1021/acs.chemrestox.8b00191 (Year: 2018).*
Hume; Blood 2012, 119, 8, 1810-1820. https://doi.org/10.1182/blood-2011-09-379214 (Year: 2012).*
Cassia S. Mizuno et al, "Design, Synthesis, and Docking Studies of Novel Benzimidazoles for the Treatment of Metabolic Syndrome", Journal of Medicinal Chemistry,vol. 53, No. 3, Feb. 11, 2010 (Feb. 11, 2010), p. 1076-1085.
Conway James G et al, "Inhibition of colony-stimulating-factor-1 signaling in vivo with the orally bioavailable cFMS kinase inhibitor GW2580", Proceedings of the National Academy of Sciences, National Academy of Sciences, US,vol. 102, No. 44, Nov. 1, 2005 (Nov. 1, 2005), p. 16078-16083.
Hao et al., "Alumina-supported heteropoly acid: An efficient catalyst for the synthesis of azaarene substituted 3-hydroxy-2-oxindole derivatives via C(sp3)-H bond functionalization", Chinese Chemical Letters, 26, pp. 599-602 (2015).
International Preliminary Report on Patentability in International Application No. PCT/US2016/042917, dated Jan. 23, 2018 (14 pages).
International Search Report and Written Opinion in International Application No. PCT/US2016/042917, dated Jan. 26, 2017 (30 pages).
John L. Kane at the 2018 (ACS-NE) Amercian Chemical Society—Northeastern Section: Medicinal Chemistry Symposium on Dec. 13, 2018.
Kubinyi, 3D QSAR in Drug Design: Ligand-Protein Interactions and Molecular Similarity, vol. 2-3 (1998), 800 pages.
Kumar et al., "β-Cyclodextrin catalysed C—C bond formation via C(sp3)-H functionalization of 2-methyl azaarenes with diones in aqueous medium", Green Chemistry, vol. 17, pp. 848-851 (Dec. 5, 2014).
Search Report with Opinion on Patentability issued in related Moroccan Application No. 42023, dated Feb. 2, 2019 (4 pages).
Shaogao Zeng et al., "Discovery of potent dipeptidyl peptidase IV inhibitors through pharmacophore hybridization and hit-to-lead optimization", Bioorganic & Medicinal Chemistry, vol. 21, pp. 1749-1755 (Feb. 8, 2013).
Shuang-Hong Hao et al., "Alumina-supported heteropoly acid: An efficient catalyst for the synthesis of azaarene substituted 3-hydroxy-2-oxindole derivatives via C(sp3)-H bond functionalization", Chinese Chemical Letters, vol. 26, pp. 599-602 (Jan. 3, 2015).
The Chemical Abstract Service Registralion No. 1347291-61-5 (Dec. 2, 2011).
The Chemical Abstract Service Registralion No. 1347338-13-9 (Dec. 2, 2011).
The Chemical Abstract Service Registration No. 1347343-41-2 (Dec. 2, 2011).
The Chemical Abstract Service Registration No. 1347464-55-4 (Dec. 2, 2011).
The Chemical Abstract Service Registration No. 1347528-83-9 (Dec. 2, 2011).
The Chemical Abstract Service Registration No. 1347650-16-1 (Dec. 2, 2011).
The Chemical Abstract Service Registration No. 1347673-50-0 (Dec. 2, 2011).
The Chemical Abstract Service Registration No. 1347698-95-6 (Dec. 2, 2011).
The Chemical Abstract Service Registration No. 1348223-10-8 (Dec. 4, 2011).
The Chemical Abstract Service Registration No. 1348621-97-5 (Dec. 4, 2011).
The Chemical Abstract Service Registration No. 1348972-34-8 (Dec. 5, 2011).
The Chemical Abstract Service Registration No. 1349135-12-1 (Dec. 5, 2011).
The Chemical Abstract Service Registration No. 1349276-26-1 (Dec. 5, 2011).

(56) References Cited

OTHER PUBLICATIONS

The Chemical Abstract Service Registration No. 1349470-05-8 (Dec. 6, 2011).
The Chemical Abstract Service Registration No. 1788907-60-7 (Jun. 25, 2015).
The Chemical Abstract Service Registration No. 1788907-62-9 (Jun. 25, 2015).
The Chemical Abstract Service Registration No. 1788907-64-1 (Jun. 25, 2015).
The Chemical Abstract Service Registration No. 1349831-67-9 (Dec. 6, 2011).
The Chemical Abstract Service Registration No. 1387586-18-6 (Aug. 7, 2012).
The Chemical Abstract Service Registration No. 1390476-30-8 (Aug. 13, 2012).
The Chemical Abstract Service Registration No. 1424499-72-8 (Mar. 17, 2013).
The Chemical Abstract Service Registration No. 1424601-42-2 (Mar. 17, 2013).
The Chemical Abstract Service Registration No. 1445131-94-1 (Jul. 17, 2013).
The Chemical Abstract Service Registration No. 1646259-46-2 (Feb. 10, 2015).
The Chemical Abstract Service Registration No. 1648159-37-8 (Feb. 16, 2015).
The Chemical Abstract Service Registration No. 1648351-85-2 (Feb. 16, 2015).
The Chemical Abstract Service Registration No. 1787479-54-2 (Jun. 24, 2015).
The Chemical Abstract Service Registration No. 1787486-49-0 (Jun. 24, 2015).
The Chemical Abstract Service Registration No. 1348052-74-3 (Dec. 4, 2011).
The Chemical Abstracts Registry (RN 1539612-75-3 and RN 1503608-00-1) (PD Feb. 9, 2015 and Dec. 25, 2013).
Weidel, E. et al., 'Composing compound libraries for hit discovery—rationality-driven preselection or random choice by structural diversity?', Future Medicinal Chemistry, pp. 2057-2072 (2014).
Wermuth, "The Practice of Medicinal Chemistry", 2d ed. (2003), 768 pages, for example p. 142.
Wu Z et al, "Design and synthesis of 3,7-diarylimidazopyridines as inhibitors of the VEGF-receptor KDR", Bioorganic & Medicinal Chemistry Letters, Pergamon, Amsterdam, NL,vol. 14, No. 4, Feb. 23, 2004 (Feb. 23, 2004), p. 909-912.
Yuan, H. et al, 'Molecular modeling of exquisitely selective c-Met inhibitors through #D-QSAR and molecular dynamics simulations', Journal of Chemical Information and Modeling, pp. 2544-2554 (2014).
Zeng et al., "Discovery of potent dipeptidyl peptidase IV inhibitors through pharmacophore hybridization and hit-to-lead optimization", Bioorganic & Medicinal Chemistry, 21, pp. 1749-1755 (2013).
Notification of Transmittal of The International Search Report and The Written Opinion of the International Searching Authority, or the Declaration, in International Application No. PCT/US2021/064831, dated Apr. 8, 2022 (11 pages).
Jia et al., "Discovery of (S)-1-(1-(Imidazo[1,2-a]pyridin-6-yl)ethyl)-6-(1-methyl-1H-pyrazol-4-yl)-1H-[1,2,3]triazolo[4,5-b] pyrazine (Volitinib) as a Highly Potent and Selective Mesenchymal-Epithelial Transition Factor (c-Met) Inhibitor in Clinical Development for Treatment of Cancer", J. Med. Chem., 57(18), pp. 7577-7589 (2014).
Tan et al., "Sulfonamides as a new scaffold for hypoxia inducible factor pathway inhibitors", Bioorganic & Medicinal Chemistry Letters, 21, pp. 528-5532 (2011).

\* cited by examiner

DEUTERATED COLONY STIMULATING FACTOR-1 RECEPTOR (CSF-1R) INHIBITORS

The application is a continuation of PCT/US2021/064831 filed Dec. 22, 2021, which claims the benefit of U.S. Provisional Application No. 63/226,549 filed Jul. 28, 2021, and U.S. Provisional Application No. 63/129,939, filed Dec. 23, 2020, each of which is incorporated herein by reference in its entirety.

BACKGROUND OF THE DISCLOSURE

Medicines can often suffer from poor absorption, distribution, metabolism and/or excretion (ADME) properties that prevent their wider use or limit their use in certain indications. Poor ADME properties can also be a major reason for the failure of drug candidates in clinical trials. Although formulation and prodrug strategies can be employed in some cases to improve certain ADME properties, these approaches often fail to address the underlying ADME problems that exist for many drugs and drug candidates.

One such problem is rapid metabolism that causes a number of drugs—which otherwise would be highly effective in treating a disease—to be cleared too rapidly from the body. A possible solution to rapid drug clearance is frequent or high dosing to attain a sufficiently high plasma level of drug. However, this approach has potential drawbacks, including poor patient compliance with the dosing regimen, side effects that become more acute with higher doses, and increased cost of treatment. Rapidly metabolized drugs may also expose patients to undesirable toxic or reactive metabolites.

Degradation of toxic or biologically reactive metabolites can also be a problem, leading to some patients receiving the drug to experience toxicities, or limits on safe dosing such that patients receive a suboptimal amount of the active agent. Sometimes, modifying dosing intervals or formulation approaches can help to reduce clinical adverse effects, but often the formation of such undesirable metabolites is intrinsic to the metabolism of the compound.

Enzymes in living organisms, such as aldehyde oxidase, can lead to unwanted metabolic degradation. Aldehyde oxidase (AO) is a cytosolic molybdenum-containing enzyme involved in the biotransformation of numerous drugs. The challenge represented by AO-mediated metabolism is driven by several overlapping factors, including the complex biology of the enzyme and the widespread use of structural motifs that are AO substrates (e.g., azaheterocycles and amides.) See, e.g., Manevski, N. et al, Metabolism by Aldehyde Oxidase: Drug Design and Complementary Approaches to Challenges in Drug Discovery, *J. Med. Chem.* 2019, 62, 10955-10994. Furthermore, differences in AO-mediated metabolism, not only between species, but also between individuals, contribute to variability in exposure and complicate human dose selection.

While a strategy of simply avoiding substrates that are susceptible to AO metabolism may seem attractive, this would impractically eliminate a vast number of potential pharmacores. Thus, various strategies have been advanced to modulate potential AO metabolism of pharmaceutical compounds. These include attempting to stop AO reactions (e.g., administering compound in conjunction with an AO inhibitor); attempting to decrease the rate of AO reactions; and using the AO metabolite as a novel scaffold or prodrug inspiration. See, e.g., Manevski et al. Moreover, in order to stop or mitigate the AO metabolism of a pharmacore, the reaction site between AO and the pharmacore must be determined. Manevski et al. provide a table of suggested strategies for mitigating AO metabolism, such as blocking the site of AO reaction, replacing carbons with heteroatoms, replacing nitrogens with carbons, removing aromaticity, reducing ring size, kinetic deuteration isotope effect ("KDIE"), and reducing logD; but in each instance knowledge of the AO degradation site is crucial. See Manevski et al. at Table 4. These strategies all include complementary measures to predict human clearance based on laboratory testing. In other words, there is no predictable way for one of ordinary skill to know if any one of the proposed strategies will work to develop a drug for a particular target, maintaining the desired effects of the drug for its intended purpose (e.g., high efficacy, target binding, or bioavailability), while also mitigating AO degradation, without extensive testing using appropriate biological samples.

BRIEF SUMMARY OF THE DISCLOSURE

It has surprisingly been found that CSF-1R inhibitor compounds as set forth in WO 2017/015267 that are substituted with deuterium can have improved ADME properties. In some aspects of the disclosure, CSF-1R inhibitor compounds substituted with deuterium at specific positions have improved ADME properties, in particular, significant resistance to AO degradation, thus potentially improving the drug efficacy and the exposure of the drug in vivo. Disclosed herein are deuterated Colony Stimulating Factor-1 Receptor inhibitors ("CSF-1R inhibitors") that are resistant to enzymatic degradation in vivo. The CSF-1R inhibitors of this disclosure are small molecule compounds that are capable of penetrating the blood-brain barrier to reach the central nervous system (CNS.) Because these compounds are advantageously able to penetrate the blood-brain barrier (a highly desirable property in neurological indications), the compounds need to be able to exhibit sufficient absorption, metabolism, distribution, and excretion (ADME) properties in order to ensure proper dosing. Metabolism issues can include rapid metabolism as well as metabolic degradation, both of which can lead to toxicities and/or suboptimal dosing of the active agent.

This disclosure relates to deuterated CSF-1R inhibitors and to the use of deuterated CSF-1R inhibitors and pharmaceutical compositions to treat disease, comprising CSF-1R inhibitors that have a surprising reduction of AO degradation and high efficacy as CSF-1R inhibitors to treat disease.

Such compounds include compounds of Formula (I):

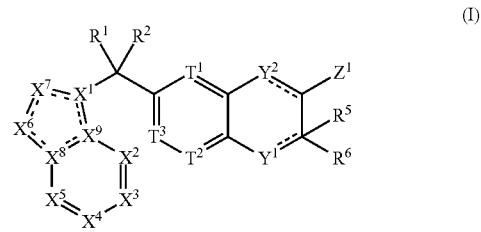

and/or or stereoisomers, optical isomers, racemic and diastereomeric mixtures, and/or pharmaceutically acceptable salts thereof, wherein:
the dashed lines represent optional double bonds;
$X^1$ is C, N, or $CR^7$;

$X^2$, $X^3$, $X^4$, $X^5$, $X^6$, and $X^7$, are each independently selected from N, $NR^7$, or $CR^7$;

$X^8$ and $X^9$ are each independently selected from N or C;

wherein each $R^7$ is independently selected from H, D, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_2-C_{10})$alkylnyl, $(C_1-C_{10})$alkylamine, $((C_1-C_{10})$alkyl$)_2$amine, $(C_2-C_{10})$alkynylamine, C(O)—, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^8$—$(C_1-C_{10})$alkyl-, $R^8$—$(C_3-C_{10})$cycloalkyl, $R^8$—$(C_2-C_9)$heterocycloalkyl, $R^8$—$(C_6-C_{14})$aryl, $R^8$—$(C_2-C_9)$heteroaryl, $R^8$—$(C_2-C_{10})$alkylnyl, $R^8$—$(C_1-C_{10})$alkylamine, $R^8$—$((C_1-C_{10})$alkyl$)_2$amine, $R^8$—$(C_2-C_{10})$alkynylamine, $R^8$—C(O)—, $R^8$—$(C_1-C_{10})$alkyl-C(O)O—, $R^8$—$(C_1-C_{10})$alkoxy-, $(C_3-C_{10})$cycloalkyl-O—, $(C_2-C_9)$heterocycloalkyl-O—, $(C_6-C_{14})$aryl-O—, $(C_2-C_9)$heteroaryl-O—, $R^8$—$(C_3-C_{10})$cycloalkyl-O—, $R^8$—$(C_2-C_9)$heterocycloalkyl-O—, $R^8$—$(C_6-C_{14})$aryl-O—, $R^8$—$(C_2-C_9)$heteroaryl-O—, HO—, halo, cyano, $H_2N$—, $(CH_3)$HN—, $(CH_3)_2N$—, $R^8R^9N$—, $R^8R^9N(O)C$—, $R^8(R^9C(O))N$—, $R^8R^9NC(O)O$—, $R^8C(O)$—, $R^8R^9NC(O)R^8N$—, $(C_1-C_{10})$alkyl-OC(O)$R^8N$—, $(C_3-C_{10})$cycloalkyl-OC(O)$R^8N$—, $(C_2-C_9)$heterocycloalkyl-OC(O)$R^8N$—, $(C_6-C_{14})$aryl-OC(O)$R^8N$—, $(C_2-C_9)$heteroaryl-OC(O)$R^8N$—, $F_3C$—, $F_2HC$—, $CH_3F_2C$—, $FH_2C$—, $CH_3FHC$—, $(CH_3)_2FC$—; NC—, $(C_1-C_{10})$alkyl(O)P—, $(C_1-C_{10})$alkyl-S—, $(C_1-C_{10})$alkyl-S—$(C_1-C_{10})$alkyl-, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_1-C_{10})$alkyl-S(O)—, $(C_3-C_{10})$cycloalkyl-S(O)—, $(C_6-C_{14})$aryl-S(O)—, $(C_2-C_9)$heterocycloalkyl-S(O)—, $(C_2-C_9)$heteroaryl-S(O)—, $(C_3-C_{10})$alkyl-S(O)$_2$—, $(C_3-C_{10})$cycloalkyl-S(O)$_2$—, $(C_6-C_{14})$aryl-S(O)$_2$—, $(C_2-C_9)$heterocycloalkyl-S(O)$_2$—, $(C_2-C_9)$heteroaryl-S(O)$_2$—, $R^8R^9NS(O)_2$—, $(C_1-C_{10})$alkyl-S(O)$_2R^8N$—, $(C_3-C_{10})$cycloalkyl-S(O)$_2R^8N$—, $(C_6-C_{14})$aryl-S(O)$_2R^8N$—, $(C_2-C_9)$heterocycloalkyl-SO$_2R^8N$—, and $(C_2-C_9)$heteroaryl-S(O)$_2R^8N$—;

wherein $R^8$ and $R^9$ are each independently selected from H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, $(CH_3)_2N$—, and $H_2N$—;

or $R^8$ and $R^9$ are taken together to form a 3 to 10 member cycloalkyl, heterocycloalkyl, aryl or heteroaryl ring;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—;

$T^1$, $T^2$, and $T^3$ is each independently selected from are each independently selected from N or $CR^{10}$, wherein each $R^{10}$ is independently selected from H, D, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_2-C_{10})$alkylnyl, $(C_1-C_{10})$alkylamine, $((C_1-C_{10})$alkyl$)_2$amine, $(C_2-C_{10})$alkynylamine, C(O)—, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{10A}$—$(C_1-C_{10})$alkyl-, $R^{10A}$—$(C_3-C_{10})$cycloalkyl, $R^{10A}$—$(C_2-C_9)$heterocycloalkyl, $R^{10A}$—$(C_6-C_{14})$aryl, $R^{10A}$—$(C_2-C_9)$heteroaryl, $R^{10A}$—$(C_2-C_{10})$alkylnyl, $R^{10A}$—$(C_1-C_{10})$alkylamine, $R^{10A}$—$((C_1-C_{10})$alkyl$)_2$amine, $R^{10A}$—$(C_2-C_{10})$alkynylamine, $R^{10A}$—C(O)—, $R^{10A}$—$(C_1-C_{10})$alkyl-C(O)O—, $R^{10A}$—$(C_1-C_{10})$alkoxy-, $(C_3-C_{10})$cycloalkyl-O—, $(C_2-C_9)$heterocycloalkyl-O—, $(C_6-C_{14})$aryl-O—, $(C_2-C_9)$heteroaryl-O—, $R^{10A}$—$(C_3-C_{10})$cycloalkyl-O—, $R^{10A}$—$(C_2-C_9)$heterocycloalkyl-O—, $R^{10A}$—$(C_6-C_{14})$aryl-O—, $R^{10A}$—$(C_2-C_9)$heteroaryl-O—, HO—, halo, cyano, $H_2N$—, $(CH_3)$HN—, $(CH_3)_2N$—, $R^{10A}R^{11}N$—, $R^{10A}R^{11}N(O)C$—, $R^{10A}(R^{11}C(O))N$—, $R^{10A}R^{11}NC(O)O$—, $R^{10A}(O)$—, $R^{10A}R^{11}NC(O)R^{10A}N$—, $(C_1-C_{10})$alkyl-OC(O)$R^{10A}N$—, $(C_3-C_{10})$cycloalkyl-OC(O)$R^{10A}N$—, $(C_2-C_9)$heterocycloalkyl-OC(O)$R^{10A}N$—, $(C_6-C_{14})$aryl-OC(O)$R^{10A}N$—, $(C_2-C_9)$heteroaryl-OC(O)$R^{10A}N$—, $F_3C$—, $F_2HC$—, $CH_3F_2C$—, $FH_2C$—, $CH_3FHC$—, $(CH_3)_2FC$—; NC—, $(C_1-C_{10})$alkyl(O)P—, $(C_1-C_{10})$alkyl-S—, $(C_1-C_{10})$alkyl-S—$(C_1-C_{10})$alkyl-, $(C_3-C_{10})$cycloalkyl-S—, $(C_6-C_{14})$aryl-S—, $(C_2-C_9)$heteroalkyl-S—, $(C_2-C_9)$heterocycloalkyl-S—, $(C_2-C_9)$heteroaryl-S—, $(C_1-C_{10})$alkyl-S(O)—, $(C_3-C_{10})$cycloalkyl-S(O)—, $(C_6-C_{14})$aryl-S(O)—, $(C_2-C_9)$heterocycloalkyl-S(O)—, $(C_2-C_9)$heteroaryl-S(O)—, $(C_3-C_{10})$alkyl-S(O)$_2$—, $(C_3-C_{10})$cycloalkyl-S(O)$_2$—, $(C_6-C_{14})$aryl-S(O)$_2$—, $(C_2-C_9)$heterocycloalkyl-S(O)$_2$—, $(C_2-C_9)$heteroaryl-S(O)$_2$—, $R^{10A}R^{11}NS(O)_2$—, $(C_1-C_{10})$alkyl-S(O)$_2R^{10A}N$—, $(C_3-C_{10})$cycloalkyl-S(O)$_2R^{10A}N$—, $(C_6-C_{14})$aryl-S(O)$_2R^{10A}N$—, $(C_2-C_9)$heterocycloalkyl-SO$_2R^{10A}N$—, and $(C_2-C_9)$heteroaryl-S(O)$_2R^{10A}N$—;

wherein $R^{10A}$ and $R^{11}$ are each independently selected from H, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, $(CH_3)_2N$—, and $H_2N$—;

or $R^{10A}$ and $R^{11}$ are taken together to form a 3 to 10 member cycloalkyl, heterocycloalkyl, aryl or heteroaryl ring;

wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from D, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, COOH—$(C_3-C_{10})$cycloalkyl, $(C_1-C_{10})$alkoxy-, $(C_1-C_{10})$alkoxy-$(C_1-C_{10})$alkyl-, $(C_3-C_{10})$cycloalkyl-O—, $(C_2-C_9)$heterocycloalkyl-O—, $(C_6-C_{14})$aryl-O—, $(C_2-C_9)$heteroaryl-O—, HO—, halo, or $H_2N$—

$Y^1$ is O, $NR^{12}$, or $CR^{12}R^{13}$, wherein R$^{12}$ is absent or R$^{12}$ and R$^{13}$ are each independently selected from H, D, (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, (C$_1$-C$_{10}$)alkylamine, ((C$_1$-C$_{10}$)alkyl)$_2$amine, (C$_1$-C$_3$)alkynylamine, (C$_1$-C$_{10}$)alkyl-C(O)O—, COOH—(C$_1$-C$_{10}$)alkyl, COOH—(C$_3$-C$_{10}$)cycloalkyl, (C$_1$-C$_{10}$)alkoxy-, (C$_1$-C$_{10}$)alkoxy-(C$_1$-C$_{10}$)alkyl-, (C$_3$-C$_{10}$)cycloalkyl-O—, (C$_2$-C$_9$)heterocycloalkyl-O—, (C$_6$-C$_{14}$)aryl-O—, (C$_2$-C$_9$)heteroaryl-O—, HO—, halo, and H$_2$N—;

R$^1$ together with the carbon to which it is attached to form a carbonyl and R$^2$ is absent, or R$^1$ and R$^2$ are each independently selected from H, (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, (C$_1$-C$_{10}$)alkylamine, ((C$_1$-C$_{10}$)alkyl)$_2$amine, (C$_1$-C$_3$)alkynylamine, (C$_1$-C$_{10}$)alkoxy-, (C$_1$-C$_{10}$)alkoxy-(C$_1$-C$_{10}$)alkyl-, (C$_3$-C$_{10}$)cycloalkyl-O—, (C$_2$-C$_9$)heterocycloalkyl-O—, (C$_6$-C$_{14}$)aryl-O—, (C$_2$-C$_9$)heteroaryl-O—, HO—, halo, and H$_2$N—, or R$^1$ and R$^2$ are taken together with the carbon to which they are attached to form a 3 to 10 member ring;

R$^5$ is absent or selected from H, D, (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, (C$_1$-C$_{10}$)alkylamine, ((C$_1$-C$_{10}$)alkyl)$_2$amine, (C$_1$-C$_3$)alkynylamine, (C$_1$-C$_{10}$)alkoxy-, (C$_1$-C$_{10}$)alkoxy-(C$_1$-C$_{10}$)alkyl-, (C$_3$-C$_{10}$)cycloalkyl-O—, (C$_2$-C$_9$)heterocycloalkyl-O—, (C$_6$-C$_{14}$)aryl-O—, (C$_2$-C$_9$)heteroaryl-O—, HO—, halo, and H$_2$N—;

R$^6$ is selected from H, D, (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, (C$_2$-C$_{10}$)alkylnyl, (C$_1$-C$_{10}$)alkylamine, ((C$_1$-C$_{10}$)alkyl)$_2$amine, (C$_2$-C$_{10}$)alkynylamine, C(O)—, (C$_1$-C$_{10}$)alkyl-C(O)O—, COOH—(C$_1$-C$_{10}$)alkyl-, COOH—(C$_3$-C$_{10}$)cycloalkyl-, (C$_1$-C$_{10}$)alkoxy-, R$^{14}$—(C$_1$-C$_{10}$)alkyl-, R$^{14}$—(C$_3$-C$_{10}$)cycloalkyl, R$^{14}$—(C$_2$-C$_9$)heterocycloalkyl-, R$^{14}$—(C$_6$-C$_{14}$)aryl, R$^{14}$—(C$_2$-C$_9$)heteroaryl, R$^{14}$—(C$_2$-C$_{10}$)alkylnyl, R$^{14}$—(C$_1$-C$_{10}$)alkylamine, R$^{14}$—((C$_1$-C$_{10}$)alkyl)$_2$amine, R$^{14}$—(C$_2$-C$_{10}$)alkynylamine, R$^{14}$—C(O)—, R$^{14}$—(C$_1$-C$_{10}$)alkyl-C(O)O—, R$^{14}$—(C$_1$-C$_{10}$)alkoxy-, (C$_3$-C$_{10}$)cycloalkyl-O—, (C$_2$-C$_9$)heterocycloalkyl-O—, (C$_6$-C$_{14}$)aryl-O—, (C$_2$-C$_9$)heteroaryl-O—, R$^{14}$—(C$_3$-C$_{10}$)cycloalkyl-O—, R$^{14}$—(C$_2$-C$_9$)heterocycloalkyl-O—, R$^{14}$—(C$_6$-C$_{14}$)aryl-O—, R$^{14}$—(C$_2$-C$_9$)heteroaryl-O—, HO—, halo, cyano, H$_2$N—, (CH$_3$)HN—, (CH$_3$)$_2$N—, R$^{14}$R$^{15}$N R$^{14}$R$^{15}$N(O)C— R$^{14}$(R$^{15}$C(O))N—, R$^{14}$R$^{15}$NC(O)O—, R$^{14}$C(O)—, R$^{14}$R$^{15}$NC(O)R$^{14}$N—, (C$_1$-C$_{10}$)alkyl-OC(O)R$^{14}$N—, (C$_3$-C$_{10}$)cycloalkyl-OC(O)R$^{14}$N—, (C$_2$-C$_9$)heterocycloalkyl-OC(O)R$^{14}$N—, (C$_6$-C$_{14}$)aryl-OC(O)R$^{14}$N—, (C$_2$-C$_9$)heteroaryl-OC(O)R$^{14}$N—, F$_3$C—, F$_2$HC—, CH$_3$F$_2$C—, FH$_2$C— CH$_3$FHC—, (CH$_3$)$_2$FC—; NC—, (C$_1$-C$_{10}$)alkyl(O)P—, (C$_1$-C$_{10}$)alkyl-S—, (C$_1$-C$_{10}$)alkyl-S—(C$_1$-C$_{10}$)alkyl-, (C$_3$-C$_{10}$)cycloalkyl-S—, (C$_6$-C$_{14}$)aryl-S—, (C$_2$-C$_9$)heteroalkyl-S—, (C$_2$-C$_9$)heterocycloalkyl-S—, (C$_2$-C$_9$)heteroaryl-S—, (C$_1$-C$_{10}$)alkyl-S(O)—, (C$_3$-C$_{10}$)cycloalkyl-S(O)—, (C$_6$-C$_{14}$)aryl-S(O)—, (C$_2$-C$_9$)heterocycloalkyl-S(O)—, (C$_2$-C$_9$)heteroaryl-S(O)—, (C$_3$-C$_{10}$)alkyl-S(O)$_2$—, (C$_3$-C$_{10}$)cycloalkyl-S(O)$_2$—, (C$_6$-C$_{14}$)aryl-S(O)$_2$—, (C$_2$-C$_9$)heterocycloalkyl-S(O)$_2$—, (C$_2$-C$_9$)heteroaryl-S(O)$_2$—, R$^{14}$R$^{15}$NS(O)$_2$—, (C$_1$-C$_{10}$)alkyl-S(O)$_2$R$^{14}$N—, (C$_3$-C$_{10}$)cycloalkyl-S(O)$_2$R$^{14}$N—, (C$_6$-C$_{14}$)aryl-S(O)$_2$R$^{14}$N—, (C$_2$-C$_9$)heterocycloalkyl-SO$_2$R$^{14}$N—, and (C$_2$-C$_9$)heteroaryl-S(O)$_2$R$^{14}$N—;

wherein R$^{14}$ and R$^{15}$ are each independently selected from H, D, (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, (C$_1$-C$_{10}$)alkylamine, ((C$_1$-C$_{10}$)alkyl)$_2$amine, (C$_1$-C$_3$)alkynylamine, (C$_1$-C$_{10}$)alkyl-C(O)O—, COOH—(C$_1$-C$_{10}$)alkyl, COOH—(C$_3$-C$_{10}$)cycloalkyl, (C$_1$-C$_{10}$)alkoxy-, (C$_1$-C$_{10}$)alkoxy-(C$_1$-C$_{10}$)alkyl-, (C$_3$-C$_{10}$)cycloalkyl-O—, (C$_2$-C$_9$)heterocycloalkyl-O—, (C$_6$-C$_{14}$)aryl-O—, (C$_2$-C$_9$)heteroaryl-O—, HO—, F$_2$HC—O—, halo, (CH$_3$)$_2$N—, H$_2$N—, F$_3$C—C(O)—, F$_3$C—, and F$_2$HC—;

or R$^{14}$ and R$^{15}$ are taken together to form a 3 to 10 member cycloalkyl, heterocycloalkyl, aryl or heteroaryl ring;

wherein each (C$_1$-C$_{10}$)alkyl, (C$_6$-C$_{14}$)aryl, (C$_2$-C$_9$)heteroaryl, (C$_3$-C$_{10}$)cycloalkyl, or (C$_2$-C$_9$)heterocycloalkyl are further optionally substituted by one to four groups selected from (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, (C$_1$-C$_{10}$)alkylamine, ((C$_1$-C$_{10}$)alkyl)$_2$amine, (C$_1$-C$_3$)alkynylamine, (C$_1$-C$_{10}$)alkyl-C(O)O—, COOH—(C$_1$-C$_{10}$)alkyl, COOH—(C$_3$-C$_{10}$)cycloalkyl, (C$_1$-C$_{10}$)alkoxy-, (C$_1$-C$_{10}$)alkoxy-(C$_1$-C$_{10}$)alkyl-, (C$_3$-C$_{10}$)cycloalkyl-O—, (C$_2$-C$_9$)heterocycloalkyl-O—, (C$_6$-C$_{14}$)aryl-O—, (C$_2$-C$_9$)heteroaryl-O—, HO—, halo, or H$_2$N—;

Z$^1$ is selected from H, halo, (C$_1$-C$_{10}$)alkyl, (C$_2$-C$_9$)heteroalkyl, (C$_1$-C$_{10}$)alkylamine, ((C$_1$-C$_{10}$)alkyl)$_2$amine, (C$_2$-C$_{10}$)alkynylamine, (C$_1$-C$_{10}$)alkoxy-, or H$_2$N—;

Y$^2$ is O, S, NR$^{17}$, or CR$^{17}$R$^{18}$, and wherein R$^{17}$ is absent or R$^{17}$ and R$^{18}$ are each independently selected from H, (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, (C$_1$-C$_{10}$)alkylamine, ((C$_1$-C$_{10}$)alkyl)$_2$amine, (C$_1$-C$_3$)alkynylamine, (C$_1$-C$_{10}$)alkyl-C(O)O—, COOH—(C$_1$-C$_{10}$)alkyl, COOH—(C$_3$-C$_{10}$)cycloalkyl, (C$_1$-C$_{10}$)alkoxy-, (C$_1$-C$_{10}$)alkoxy-(C$_1$-C$_{10}$)alkyl-, (C$_3$-C$_{10}$)cycloalkyl-O—, (C$_2$-C$_9$)heterocycloalkyl-O—, (C$_6$-C$_{14}$)aryl-O—, (C$_2$-C$_9$)heteroaryl-O—, HO—, halo, or H$_2$N—;

wherein at least one of R$^7$, R$^1$, or R$^2$ is D.

In at least one aspect the disclosure relates to compounds of Formula (I):

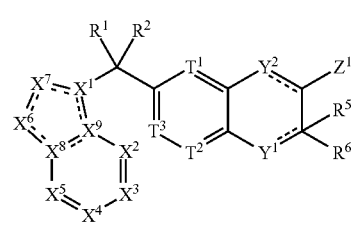

(I)

and/or stereoisomers, optical isomers, racemic and diastereomeric mixtures, and/or pharmaceutically acceptable salts thereof, wherein:

the dashed lines represent optional double bonds;

X$^1$, is C, N, or CR$^7$;

X$^2$, X$^3$, X$^4$, X$^5$, X$^6$, X$^7$, are each independently selected from N, NR$^7$, or CR$^7$;

X$^8$, and X$^9$ are each independently selected from N or C;

wherein each R$^7$ is independently selected from H, D, (C$_1$-C$_{10}$)alkyl, (C$_3$-C$_{10}$)cycloalkyl, (C$_2$-C$_9$)heterocycloalkyl, (C$_2$-C$_9$)heteroaryl, (C$_2$-C$_{10}$)alkynylamine, (C$_1$-C$_{10}$)alkyl-C(O)O—, (C$_1$-C$_{10}$)alkoxy-, R$^8$—(C$_2$-C$_9$)heterocycloalkyl, R$^8$—(C$_2$-C$_9$)heteroaryl, R$^8$—(C$_2$-C$_{10}$)alkylnyl, R$^8$—(C$_2$-C$_{10}$)alkynylamine, R$^8$—(C$_1$-

$C_{10}$)alkoxy-, $R^8$—($C_2$-$C_9$)heterocycloalkyl-O—, halo, cyano, $H_2N$—, $(CH_3)HN$—, $(CH_3)_2N$—, $R^8C(O)$—, $F_3C$—, $F_2HC$—, $CH_3F_2C$—, $FH_2C$—, $CH_3FHC$—, and $(CH_3)_2FC$;

wherein $R^8$ is each independently selected from H, ($C_1$-$C_{10}$)alkyl, ($C_2$-$C_9$)heterocycloalkyl, ($C_1$-$C_{10}$)alkylamine, ($C_1$-$C_{10}$)alkyl-C(O)O—, ($C_1$-$C_{10}$)alkoxy-, HO—, halo, $(CH_3)_2N$—, and $H_2N$—;

wherein each ($C_1$-$C_{10}$)alkyl, ($C_2$-$C_9$)heteroaryl, or ($C_2$-$C_9$)heterocycloalkyl are further optionally substituted by one to four groups selected from deuterium, ($C_1$-$C_{10}$)alkyl, or ($C_1$-$C_{10}$)alkylamine;

$T^1$, $T^2$, and $T^3$ are each independently selected from N or $CR^{10}$;

wherein each $R^{10}$ is independently selected from H, D, ($C_1$-$C_{10}$)alkyl, ($C_3$-$C_{10}$)cycloalkyl, ($C_1$-$C_{10}$)alkylamine, (($C_1$-$C_{10}$)alkyl)$_2$amine, ($C_2$-$C_{10}$)alkynylamine, ($C_1$-$C_{10}$)alkyl-C(O)O—, COOH—($C_1$-$C_{10}$)alkyl-, COOH—($C_3$-$C_{10}$)cycloalkyl-, ($C_1$-$C_{10}$)alkoxy-, $R^{10A}$—($C_1$-$C_{10}$)alkyl-, $R^{10A}$—($C_1$-$C_{10}$)alkylamine, $R^{10A}$—(($C_1$-$C_{10}$)alkyl)$_2$amine, $R^{10A}$—($C_2$-$C_{10}$)alkynylamine, $R^{10A}$—C(O)—, $R^{10A}$—($C_1$-$C_{10}$)alkyl-C(O)O—, $R^{10A}$—($C_1$-$C_{10}$)alkoxy-, HO—, and halo, cyano, $H_2N$—, $(CH_3)HN$—, $(CH_3)_2N$—, $R^{10A}R^{11}N$—, $R^{10A}R^{11}N(O)C$—, $R^{10A}(R^{11}C(O))N$—, $R^{10A}R^{11}NC(O)O$—, $R^{10A}C(O)$—, $R^{10A}R^{11}NC(O)R^{10A}N$—, ($C_1$-$C_{10}$)alkyl-OC(O)$R^{10A}N$—, $F_3C$—, $F_2HC$—, $CH_3F_2C$—, $FH_2C$—, $CH_3FHC$—, $(CH_3)_2FC$—;

wherein $R^{10A}$ and $R^{11}$ are each independently selected from H, D, ($C_1$-$C_{10}$)alkyl, ($C_1$-$C_{10}$)alkylamine, (($C_1$-$C_{10}$)alkyl)$_2$amine, ($C_1$-$C_3$)alkynylamine, ($C_1$-$C_{10}$)alkyl-C(O)O—, COOH—($C_1$-$C_{10}$)alkyl, ($C_1$-$C_{10}$)alkoxy-, ($C_1$-$C_{10}$)alkoxy-($C_1$-$C_{10}$)alkyl-, HO—, halo, $(CH_3)_2N$—, and $H_2N$—;

wherein each ($C_1$-$C_{10}$)alkyl are further optionally substituted by one to four groups selected from D, ($C_1$-$C_{10}$)alkyl, ($C_1$-$C_{10}$)alkylamine, (($C_1$-$C_{10}$)alkyl)$_2$amine, ($C_1$-$C_{10}$)alkoxy-, ($C_1$-$C_{10}$)alkoxy-($C_1$-$C_{10}$)alkyl-, HO—, halo, or $H_2N$—

$Y^1$ is O, $NR^{12}$, or $CR^{12}R^{13}$;

wherein $R^{12}$ is absent or $R^{12}$ and $R^{13}$ are each independently selected from H, D, ($C_1$-$C_{10}$)alkyl, ($C_1$-$C_{10}$)alkylamine, (($C_1$-$C_{10}$)alkyl)$_2$amine, ($C_1$-$C_3$)alkynylamine, ($C_1$-$C_{10}$)alkoxy-, ($C_1$-$C_{10}$)alkoxy-($C_1$-$C_{10}$)alkyl-, HO—, halo, and $H_2N$—;

$R^1$ and $R^2$ are each independently selected from H, D, ($C_1$-$C_{10}$)alkyl, HO—, halo, and $H_2N$;

$R^5$ is absent or selected from H, D, ($C_1$-$C_{10}$)alkyl, HO—, halo, and $H_2N$—; and $R^6$ is selected from D, ($C_1$-$C_{10}$)alkyl, ($C_3$-$C_{10}$)cycloalkyl, ($C_2$-$C_9$)heteroaryl, ($C_1$-$C_{10}$)alkylamine, (($C_1$-$C_{10}$)alkyl)$_2$amine, $R^{14}$—($C_3$-$C_{10}$)cycloalkyl, $R^{14}$—($C_6$-$C_{14}$)aryl, $R^{14}$—($C_2$-$C_9$)heteroaryl, and $R^{14}$—($C_1$-$C_{10}$)alkylamine;

wherein $R^{14}$ is each independently selected from H, D, ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, ($C_1$-$C_{10}$)alkylamine, (($C_1$-$C_{10}$)alkyl)$_2$amine, ($C_1$-$C_{10}$)alkoxy-, HO—, $F_2HC$—O—, halo, $(CH_3)_2N$—, $F_3C$—C(O)—, $F_3C$—, and $F_2HC$—;

wherein each ($C_1$-$C_{10}$)alkyl, ($C_6$-$C_{14}$)aryl, ($C_2$-$C_9$)heteroaryl, ($C_3$-$C_{10}$)cycloalkyl, or ($C_2$-$C_9$)heterocycloalkyl are further optionally substituted by one to four groups selected from ($C_1$-$C_{10}$)alkyl, ($C_3$-$C_{10}$)cycloalkyl, ($C_2$-$C_9$)heterocycloalkyl, ($C_6$-$C_{14}$)aryl, ($C_2$-$C_9$)heteroaryl, HO—, halo, or $H_2N$—; and $Z^1$ is selected from H, halo, and ($C_1$-$C_{10}$)alkyl;

$Y^2$ is O, $NR^{17}$, or $CR^{17}R^{18}$;

wherein $R^{17}$ is absent or $R^{17}$ and $R^{18}$ are each independently selected from H, ($C_1$-$C_{10}$)alkyl, HO—, halo, and $H_2N$—;

wherein at least one of $R^7$, $R^1$, or $R^2$ is D.

In at least one aspect the disclosure relates to compounds of Formula (I'):

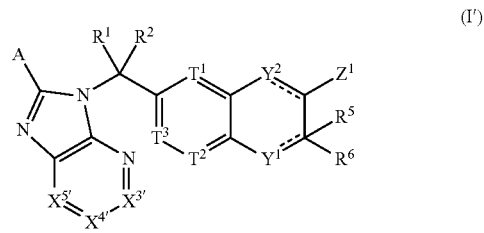

(I')

and/or stereoisomers, optical isomers, racemic and diastereomeric mixtures, and/or pharmaceutically acceptable salts thereof, wherein:

the dashed lines represent optional double bonds;

A is selected from H and D;

$X^{3'}$ is $CR^{3'}$ wherein $R^{3'}$ is selected from H and D;

$X^{4'}$ is $CR^{4'}$ wherein $R^{4'}$ is selected from H, D, and $R^7$; and $X^{5'}$ is $CR^{5'}$ wherein $R^{5'}$ is selected from H and D, wherein at least one of A, $R^{3'}$, $R^{4'}$, and $R^{5'}$ is D.

This disclosure also relates to pharmaceutical formulations comprising deuterated CSF-1R inhibitors and to the use, for treating disease, of deuterated CSF-1R inhibitors and pharmaceutical compositions comprising CSF-1R inhibitors. Further disclosed herein is the use of deuterated CSF-1R inhibitors and pharmaceutical compositions comprising deuterated CSF-1R inhibitors that are aldehyde oxidase degradation-resistant, for treating immune-mediated diseases, including multiple sclerosis, lupus nephritis, and rheumatoid arthritis, and neurological diseases, including amyotrophic lateral sclerosis (ALS), multiple system atrophy (MSA), progressive supranuclear palsy (PSP) and Huntington's disease.

With deuterium modification, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to materially affect the biochemical potency and selectivity of the drug as compared to the original chemical entity that contains only hydrogen.

It should be noted that the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). Results, however, have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The compounds of the disclosure are CSF-1R inhibitor compounds as set forth in WO 2017/015267 that are substituted with deuterium and have improved ADME properties, and are in particular, highly resistant to AO degradation, thus potentially improving the drug efficacy and the exposure of the drug in vivo. This result is highly surprising and unexpected given the interlocking and conflicting challenges of overcoming AO-mediated metabolism as described by Manevski et al, e.g., the need to assess and balance multiple conflicting factors such as compound structural motifs, experimentally determining in vitro and in vivo properties, e.g., in liver microsomes or hepatocytes; and the uncertainty noted above of obtaining improved ADME properties in particular, reduction in AO degradation, with deuterium substitution.

In an embodiment, the disclosure relates to a method of treating a disease or disorder mediated by colony stimulating factor-1 receptors (CSF-1R) or a disease or disorder in which CSF-1R is implicated in a subject in need of such treatment, comprising administering to the subject an effective amount of a compound according to Formula (I) or Formula (I'), and/or stereoisomers, optical isomers, racemic and diastereomeric mixtures, and/or pharmaceutically acceptable salts thereof. In another embodiment, the disease or disorder is a neurological and immune mediated disease, including Multiple Sclerosis, ALS, MSA, PSP, Huntington's disease, lupus, lupus nephritis, and rheumatoid arthritis in a subject in need of such treatment comprising administering to the subject an effective amount of a compound according to Formula (I) or Formula (I'), and/or stereoisomers, optical isomers, racemic and diastereomeric mixtures, and/or pharmaceutically acceptable salts thereof.

The disclosure also relates to pharmaceutical compositions comprising a compound according to Formula (I) or Formula (I').

DETAILED DESCRIPTION OF THE DISCLOSURE

Figure 1A:
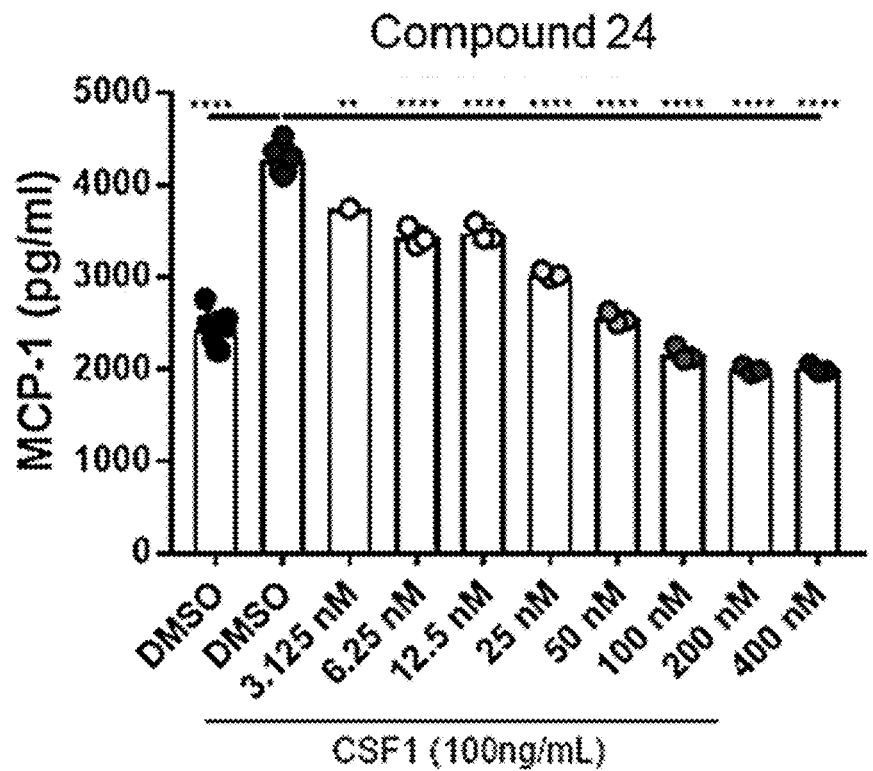
FIGS. 1A and 1B shows the impact of an exemplary CSF-1R inhibitory compound (Compound 24) on MCP-1 chemokine production following CSF-1 stimulation. The mean (FIG. 1A) and standard deviation (FIG. 1B) are shown.
Figure 1B:
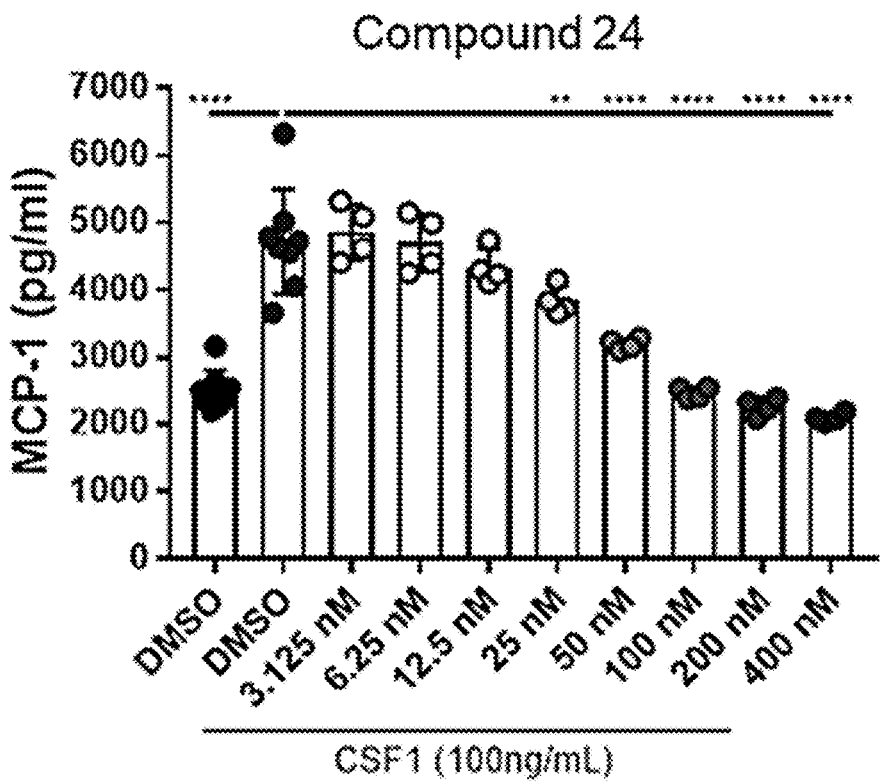
Figure 2A:
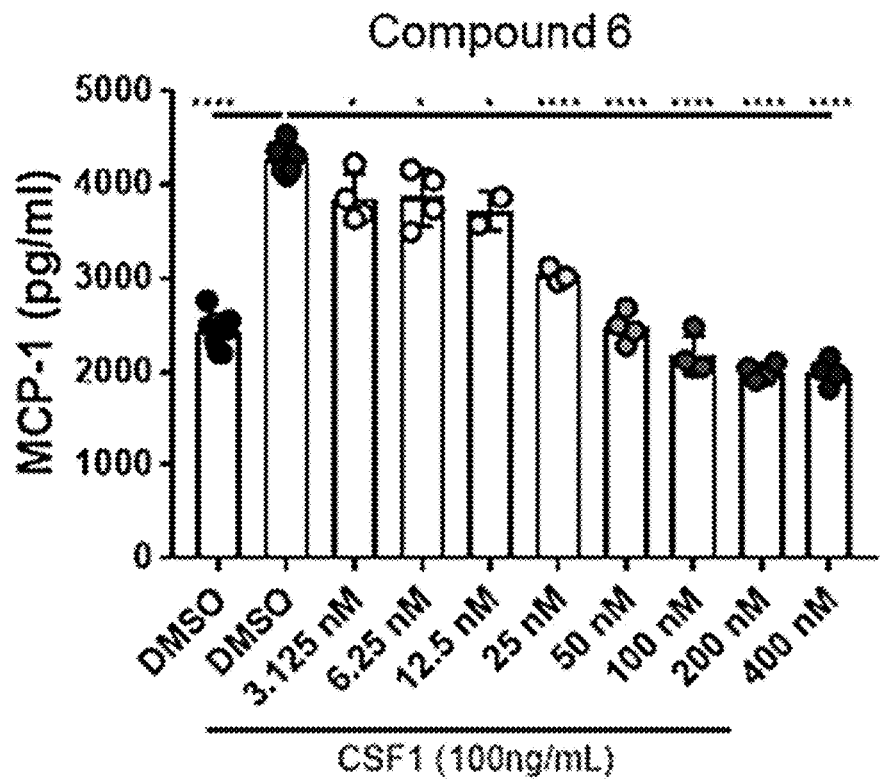
FIGS. 2A and 2B show the impact of an exemplary deuterated CSF-1R inhibitory compound (Compound 6) on MCP-1 chemokine production following CSF-1. The mean (FIG. 2A) and standard deviation (FIG. 2B) are shown.
Figure 2B:
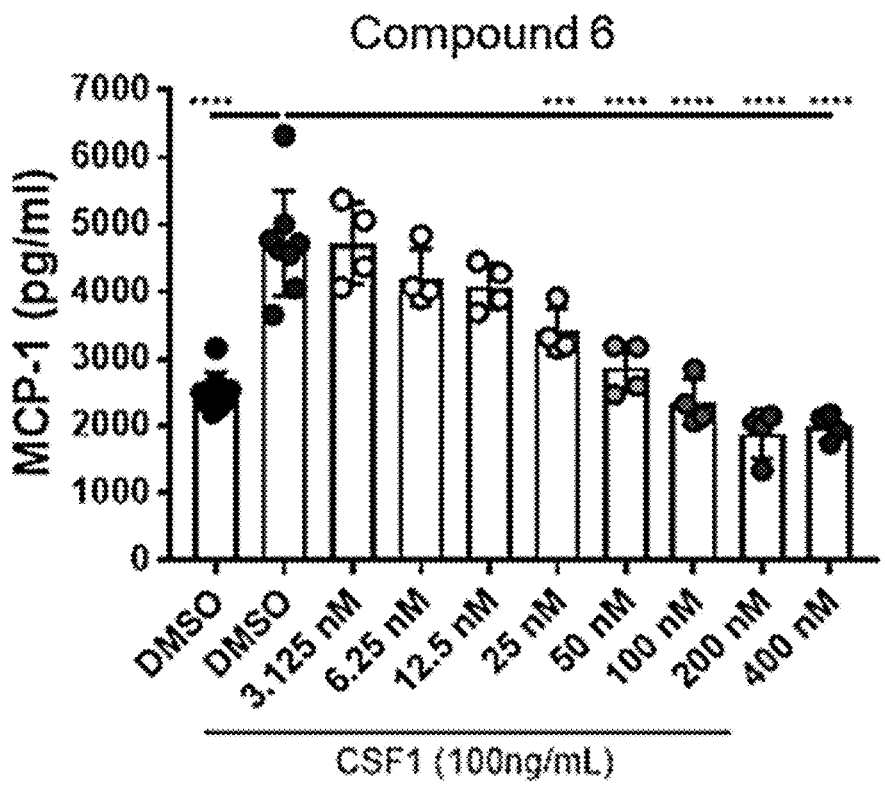
Figure 3A:
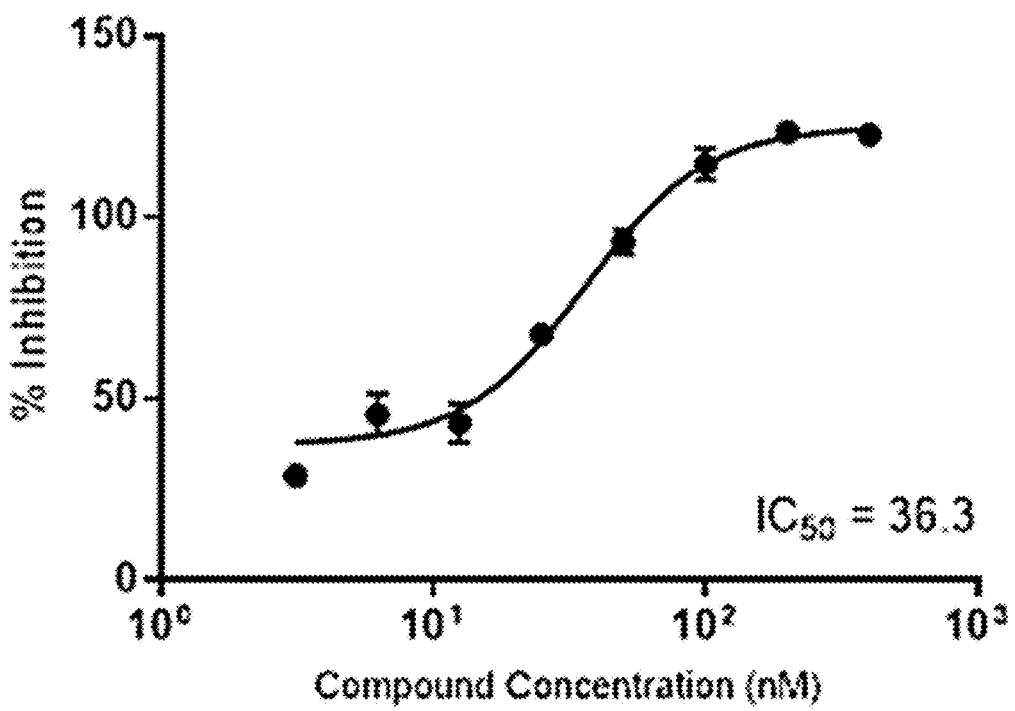
FIGS. 3A and 3B show $IC_{50}$ curves for the experiment of FIG. 1.
Figure 3B:
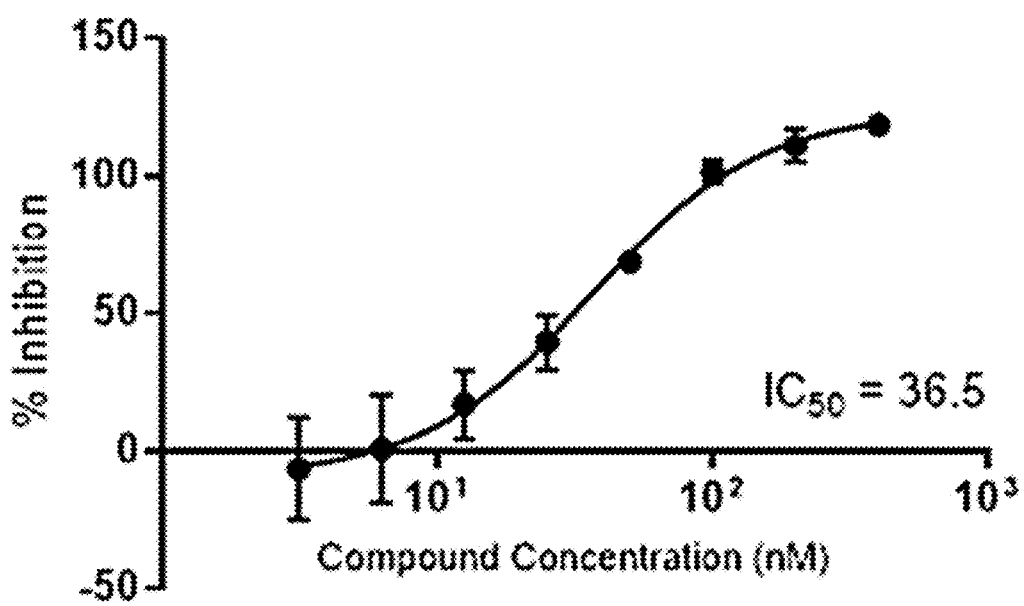
Figure 4A:
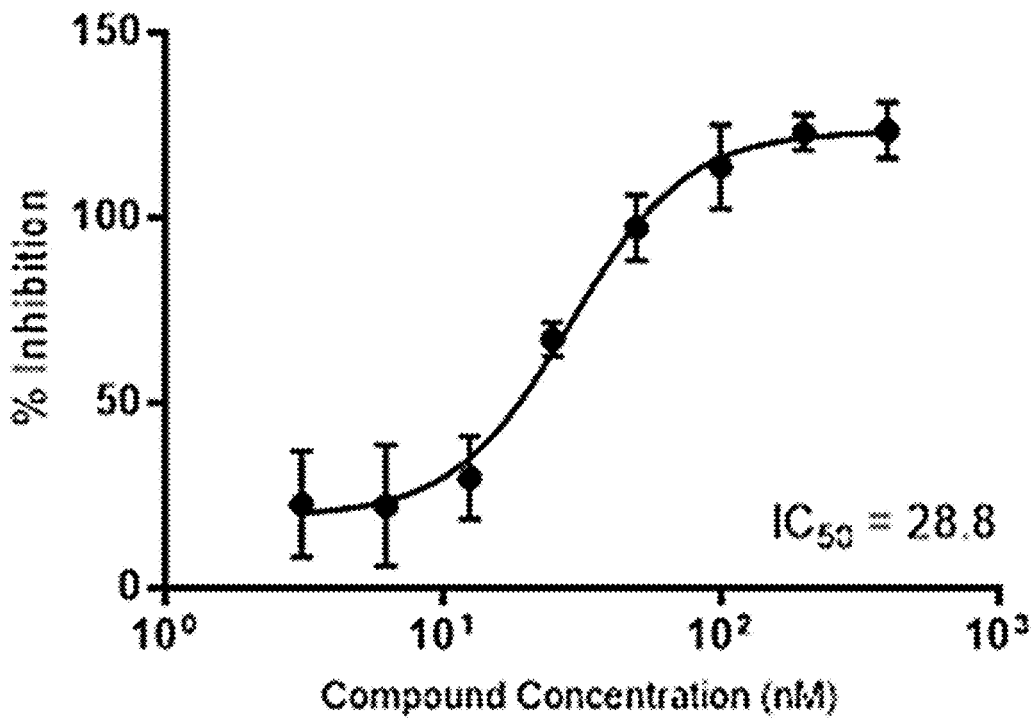
FIGS. 4A and 4B show $IC_{50}$ curves for the experiment of FIG. 2.
Figure 4B:
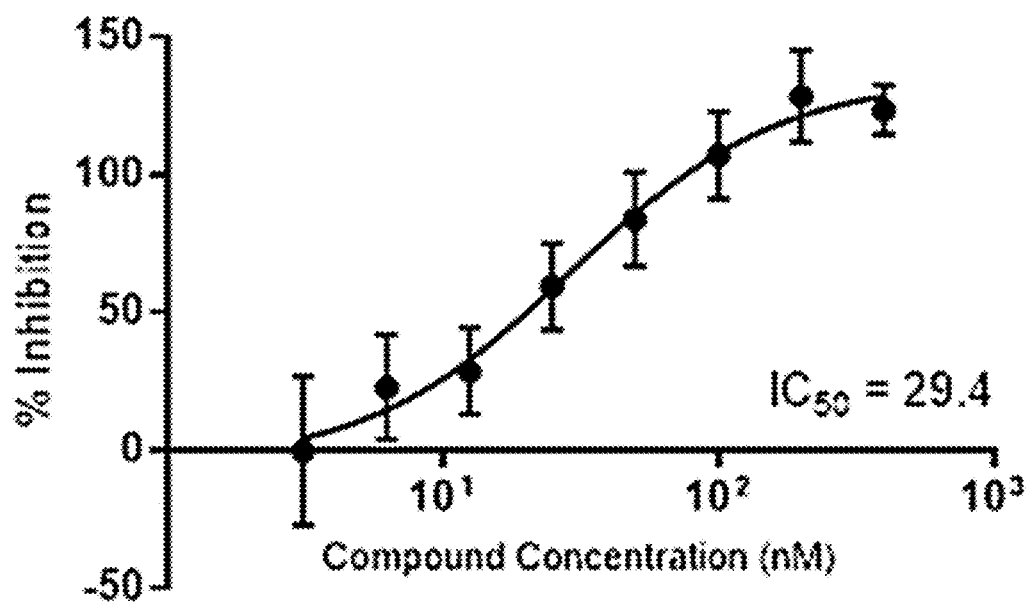

This disclosure relates to colony stimulating factor-1 receptor inhibitors ("CSF-1R inhibitors") that are small molecules capable of penetrating the blood-brain barrier to reach the central nervous system (CNS). This disclosure also relates to pharmaceutical formulations comprising CSF-1R inhibitors and to the use of CSF-1R inhibitors and pharmaceutical compositions comprising CSF-1R inhibitors to treat disease. Such diseases include immune-mediated diseases, including multiple sclerosis, lupus nephritis, rheumatoid arthritis, and neurological diseases, including amyotrophic lateral sclerosis (ALS) and Huntington's disease.

Multiple sclerosis is a chronic, inflammatory, demyelinating disease of the CNS that causes intermittent relapses and progressive neurological deterioration. Activated microglial cells and macrophages contribute to CNS damage and play a significant role in disease progression and neurodegeneration in multiple sclerosis. These activated innate immune cells can participate in antigen presentation and produce inflammatory and neurotoxic mediators that are destructive to neurons and oligodendrocytes. CSF-1R is a receptor-tyrosine kinase expressed on macrophages, monocytes, and microglial cells and represents a potential target for therapeutic modulation of effector function.

The CSF-1R inhibitors described herein are particularly useful in the treatment of multiple sclerosis, and have demonstrated the following in preclinical in vitro and in vivo studies: a reduction of inflammatory cytokines/chemokines, inhibition of the expansion and activation of macrophages/microglial cells while not negatively affecting their phagocytic activity, an inhibition of CNS infiltration in multiple in vivo disease models, and a therapeutic benefit in mouse disease models. These data suggest that inhibition of CNS macrophage/microglia effector functions through CSF-1R antagonism provide neuroprotection in multiple sclerosis by reducing inflammation, demyelination, and axonal loss. CSF-1R signaling has also been found to be upregulated in ALS and it may be as well in, e.g., PSP and MSA, and it has been noted in the literature that CSF-1R inhibition appears to be efficacious in preclinical models of ALS, MSA and PSP. See, e.g., Gowing, G. et al., Macrophage colony stimulating factor (M-CSF) exacerbates ALS disease in a mouse model through altered responses of microglia expressing mutant superoxide dismutase, *Exp Neurol.* 2009 December; 220(2):267-75; Martinez-Muriana, A. et al., $CSF_1R$ blockade slows the progression of amyotrophic lateral sclerosis by reducing microgliosis and invasion of macrophages into peripheral nerves, *Sci Rep.* 2016 May 13; 6:25663; Neal, M. L. et al., Pharmacological inhibition of $CSF_1R$ by GW2580 reduces microglial proliferation and is protective against neuroinflammation and dopaminergic neurodegeneration. *FASEB J.* 2020 January; 34(1):1679-1694; Oh, S. J. et al., Evaluation of the Neuroprotective Effect of Microglial Depletion by CSF-1R Inhibition in a Parkinson's Animal Model. Mol Imaging Biol. 2020 August; 22(4):1031-1042; Mancuso, R. et al., $CSF_1R$ inhibitor JNJ-40346527 attenuates microglial proliferation and neurodegeneration in P301S mice. Brain. 2019 Oct. 1; 142(10):3243-3264; Lodder, C. et al., $CSF_1R$ inhibition rescues tau pathology and neurodegeneration in an A/T/N model with combined AD pathologies, while preserving plaque associated microglia. Acta Neuropathol Commun. 2021 Jun. 8; 9(1):108.

In one embodiment, the disclosure relates to compounds of Formula (I):

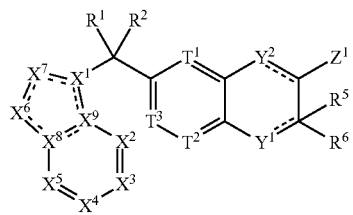

(I)

and/or stereoisomers, optical isomers, racemic and diastereomeric mixtures, and/or pharmaceutically acceptable salts thereof, wherein:

the dashed lines represent optional double bonds;

$X^1$, is C, N, or $CR^7$;

$X^2$, $X^3$, $X^4$, $X^5$, $X^6$, $X^7$, are each independently selected from N, $NR^7$, or $CR^7$;

$X^8$, and $X^9$ are each independently selected from N or C wherein each $R^7$ is independently selected from H, D, $(C_1-C_{10})$alkyl, $(C_3-C_{10})$cycloalkyl, $(C_2-C_9)$heterocycloalkyl, $(C_2-C_9)$heteroaryl, $(C_2-C_{10})$alkynylamine, $(C_1-C_{10})$alkyl-C(O)O—, $(C_1-C_{10})$alkoxy-, $R^8$-$(C_2-C_9)$heterocycloalkyl, $R^8$-$(C_2-C_9)$heteroaryl, $R^8$-$(C_2-C_{10})$alkylnyl, $R^8$-$(C_2-C_{10})$alkynylamine, $R^8$-$(C_1-C_{10})$alkoxy-, $R^8$-$(C_2-C_9)$heterocycloalkyl-O—, halo, cyano, $H_2N$—, $(CH_3)HN$—, $(CH_3)_2N$—, $R^8C(O)$—, $F_3C$—, $F_2HC$—, $CH_3F_2C$—, $FH_2C$—, $CH_3FHC$—, and $(CH_3)_2FC$;

wherein $R^8$ is each independently selected from of H, $(C_1-C_{10})$alkyl, $(C_2-C_9)$heterocycloalkyl, $(C_1-C_{10})$alkylamine, $(C_1-C_{10})$alkyl-C(O)O—, $(C_1-C_{10})$alkoxy-, HO—, halo, $(CH_3)_2N$—, and $H_2N$—;

wherein each $(C_1-C_{10})$alkyl, $(C_2-C_9)$heteroaryl, or $(C_2-C_9)$heterocycloalkyl are further optionally substituted by one to four groups selected from deuterium, $(C_1-C_{10})$alkyl, or $(C_1-C_{10})$alkylamine;

$T^1$, $T^2$, and $T^3$ are each independently selected from N or $CR^{10}$, wherein each $R^{110}$ is independently selected from H, D, $(C_1-C_{10})$alkyl, $(C_3-C_{10})$cycloalkyl, $(C_1-C_{10})$alkylamine, $((C_1-C_{10})$alkyl$)_2$amine, $(C_2-C_{10})$alkynylamine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{10A}$—$(C_1-C_{10})$alkyl-, $R^{10A}$—$(C_1-C_{10})$alkylamine, $R^{10A}$—$((C_1-C_{10})$alkyl$)_2$amine, $R^{10A}$—$(C_2-C_{10})$alkynylamine, $R^{10A}$—C(O)—, $R^{10A}$—$(C_1-C_{10})$alkyl-C(O)O—, $R^{10A}$—$(C_1-C_{10})$alkoxy-, HO—, and halo, cyano, $H_2N$—, $(CH_3)HN$—, $(CH_3)_2N$—, $R^{10A}R^{11}N$—, $R^{10A}R^{11}N(O)C$—, $R^{10A}(R^{11}C(O))N$—, $R^{10A}R^{11}NC(O)O$—, $R^{10A}C(O)$—, $R^{10A}R^{11}NC(O)R^{10A}N$—, $(C_1-C_{10})$alkyl-OC(O)$R^{10A}N$—, $F_3C$—, $F_2HC$—, $CH_3F_2C$—, $FH_2C$—, $CH_3FHC$—, $(CH_3)_2FC$—;

wherein $R^{10A}$ and $R^{11}$ are each independently selected from H, D, $(C_1-C_{10})$alkyl, $(C_1-C_{10})$alkylamine, $((C_1-C_{10})$alkyl$)_2$amine, $(C_1-C_3)$alkynylamine, $(C_1-C_{10})$alkyl-C(O)O—, COOH—$(C_1-C_{10})$alkyl, $(C_1-C_{10})$alkoxy-, $(C_1-C_{10})$alkoxy-$(C_1-C_{10})$alkyl-, HO—, halo, $(CH_3)_2N$—, and $H_2N$—;

wherein each $(C_1-C_{10})$alkyl are further optionally substituted by one to four groups selected from D, $(C_1-C_{10})$alkyl, $(C_1-C_{10})$alkylamine, $((C_1-C_{10})$alkyl$)_2$amine, $(C_1-C_{10})$alkoxy-, $(C_1-C_{10})$alkoxy-$(C_1-C_{10})$alkyl-, HO—, halo, or $H_2N$—

$Y^1$ is O, $NR^{12}$, or $CR^{12}R^{13}$;

wherein $R^{12}$ is absent or $R^{12}$ and $R^{13}$ are each independently selected from H, D, $(C_1-C_{10})$alkyl, $(C_1-C_{10})$alkylamine, $((C_1-C_{10})$alkyl$)_2$amine, $(C_1-C_3)$alkynylamine, $(C_1-C_{10})$alkoxy-, $(C_1-C_{10})$alkoxy-$(C_1-C_{10})$alkyl-, HO—, halo, and $H_2N$—;

$R^1$ and $R^2$ are each independently selected from H, D, $(C_1-C_{10})$alkyl, HO—, halo, and $H_2N$;

$R^5$ is absent or selected from H, D, $(C_1-C_{10})$alkyl, HO—, halo, and $H_2N$—; and $R^6$ is selected from D, $(C_1-C_{10})$alkyl, $(C_3-C_{10})$cycloalkyl, $(C_2-C_9)$heteroaryl, $(C_1-C_{10})$alkylamine, $((C_1-C_{10})$alkyl)$_2$amine, R$^{14}$-(C$_3$-C$_{10}$)cycloalkyl, R$^{14}$—(C$_6$-C$_{14}$)aryl, R$^{14}$—(C$_2$-C$_9$)heteroaryl, and R$^{14}$—(C$_1$-C$_{10}$)alkylamine;

wherein R$^{14}$ is each independently selected from the group consisting of H, D, (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, (C$_1$-C$_{10}$)alkylamine, ((C$_1$-C$_{10}$)alkyl)$_2$amine, (C$_1$-C$_{10}$)alkoxy-, HO—, F$_2$HC—O—, halo, (CH$_3$)$_2$N—, F$_3$C—C(O)—, F$_3$C—, and F$_2$HC—;

wherein each (C$_1$-C$_{10}$)alkyl, (C$_6$-C$_{14}$)aryl, (C$_2$-C$_9$)heteroaryl, (C$_3$-C$_{10}$)cycloalkyl, or (C$_2$-C$_9$)heterocycloalkyl are further optionally substituted by one to four groups selected from (C$_1$-C$_{10}$)alkyl, (C$_3$-C$_{10}$)cycloalkyl, (C$_2$-C$_9$)heterocycloalkyl, (C$_6$-C$_{14}$)aryl, (C$_2$-C$_9$)heteroaryl, HO—, halo, and H$_2$N—; and Z$^1$ is selected from H, halo, and (C$_1$-C$_{10}$)alkyl;

Y$^2$ is O, NR$^{17}$, or CR$^{17}$R$^{18}$;

wherein R$^{17}$ is absent or R$^{17}$ and R$^{18}$ are each independently selected from H, (C$_1$-C$_{10}$)alkyl, HO—, halo, or H$_2$N—;

wherein at least one of R$^7$, R$^1$, or R$^2$ is D.

In at least one embodiment of the disclosure, the compounds according to Formula (I) are such that X$^1$ is N. In at least one embodiment of the disclosure, the compounds according to Formula (I) are such that X$^2$ is N. In at least one embodiment of the disclosure, the compounds according to Formula (I) are such that X$^3$ is CR$^7$. In at least one embodiment of the disclosure, the compounds according to Formula (I) are such that X$^4$ is CR$^7$. In at least one embodiment of the disclosure, the compounds according to Formula (I) are such that X$^5$ is CR$^7$. In at least one embodiment of the disclosure, the compounds according to Formula (I) are such that X$^6$ is N. In at least one embodiment of the disclosure, the compounds according to Formula (I) are such that X$^7$ is CR$^7$. In at least one embodiment of the disclosure, the compounds according to Formula (I) are such that X$^8$ is C. In at least one embodiment of the disclosure, the compounds according to Formula (I) are such that X$^9$ is C. In at least one embodiment of the disclosure, the compounds according to Formula (I) are such that X$^1$ is N; X$^2$ is N; X$^3$ is CR$^7$; X$^4$ is CR$^7$; X$^5$ is CR$^7$; X$^6$ is N; X$^7$ is CR$^7$; X$^8$ is C; and X$^9$ is C.

In at least one embodiment of the disclosure, the compounds according to Formula (I) are such that T$^1$ is CR$^{10}$. In at least one embodiment of the disclosure, the compounds according to Formula (I) are such that T$^2$ is CR$^{10}$. In at least one embodiment of the disclosure, the compounds according to Formula (I) are such that T$^3$ is CR$^{10}$. In at least one embodiment of the disclosure, the compounds according to Formula (I) are such that at least two of T$^1$, T$^2$, and T$^3$ are each independently CR$^{10}$. In at least one embodiment of the disclosure, the compounds according to Formula (I) are such that T$^1$, T$^2$, and T$^3$ are each independently CR$^{10}$.

In at least one embodiment of the disclosure, the compounds according to Formula (I) are such that each R$^{10}$ is independently selected from H, (C$_1$-C$_{10}$)alkyl, (C$_3$-C$_{10}$)cycloalkyl, (C$_1$-C$_{10}$)alkoxy, and halo. In at least one embodiment of the disclosure, the compounds according to Formula (I) are such that each R$^{10}$ is independently selected from H, (C$_1$-C$_{10}$)alkyl, and halo. In at least one embodiment of the disclosure, the compounds according to Formula (I) are such that each R$^{10}$ is independently selected from H, (C$_1$-C$_{10}$)alkyl, (C$_1$-C$_{10}$)alkoxy, and halo. In at least one embodiment of the disclosure, the compounds according to Formula (I) are such that each R$^{10}$ is independently selected from H, (C$_1$-C$_{10}$)alkyl, (C$_{3-10}$)cycloalkyl, and halo. In at least one embodiment of the disclosure, the compounds according to Formula (I) are such that each R$^{10}$ is independently selected from H and halo.

In at least one embodiment of the disclosure, the compounds according to Formula (I) are such that Y$^1$ is O. In at least one embodiment of the disclosure, the compounds according to Formula (I) are such that Y$^2$ is O. In at least one embodiment of the disclosure, the compounds according to Formula (I) are such that Y1 and Y2 are each O.

In at least one embodiment of the disclosure, the compounds according to Formula (I) are such that Z$^1$ is selected from H, halo, and (C$_1$-C$_{10}$)alkyl. In at least one embodiment of the disclosure, the compounds according to Formula (I) are such that Z$^1$ is (C$_1$-C$_{10}$)alkyl. In at least one embodiment of the disclosure, the compounds according to Formula (I) are such that Z$^1$ is halo. In at least one embodiment of the disclosure, the compounds according to Formula (I) are such that Z$^1$ is H.

In at least one embodiment of the disclosure, the compounds according to Formula (I) are such that R$^1$ and R$^2$ are each independently selected from H and D. In at least one embodiment of the disclosure, the compounds according to Formula (I) are such that R$^1$ and R$^2$ are both H. In at least one embodiment of the disclosure, the compounds according to Formula (I) are such that R$^1$ and R$^2$ are both D. In at least one embodiment of the disclosure, the compounds according to Formula (I) are such that one of R$^{14}$ and R$^2$ is H and the other is D.

In at least one embodiment of the disclosure, the compounds according to Formula (I) are such that R$^6$ is selected from (C$_3$-C$_{10}$)cycloalkyl, (C$_2$-C$_9$)heteroaryl, R$^{14}$—(C$_6$-C$_{14}$)aryl, R$^{14}$—(C$_2$-C$_9$)heteroaryl, and R$^{14}$—(C$_1$-C$_{10}$)alkylamine; wherein R$^{14}$ is each independently selected from H, (C$_1$-C$_{10}$)alkyl, (C$_1$-C$_{10}$)alkylamine, (C$_1$-C$_{10}$)alkoxy-, HO—, F$_2$HC—O—, F$_3$C—C(O)—, F$_3$C—, and F$_2$HC—; and wherein each (C$_3$-C$_{10}$)cycloalkyl, or (C$_2$-C$_9$)heterocycloalkyl are further optionally substituted by one to four groups selected from (C$_1$-C$_{10}$)alkyl, HO—, halo, or H$_2$N—. In at least one embodiment of the disclosure, the compounds according to Formula (I) are such that R$^6$ is selected from (C$_3$-C$_{10}$)cycloalkyl, and (C$_2$-C$_9$)heteroaryl; and wherein each (C$_3$-C$_{10}$)cycloalkyl, or (C$_2$-C$_9$)heterocycloalkyl are further optionally substituted by one to two groups selected from (C$_1$-C$_{10}$)alkyl, HO—, halo, or H$_2$N—.

In another aspect the disclosure relates to compounds of Formula (I'):

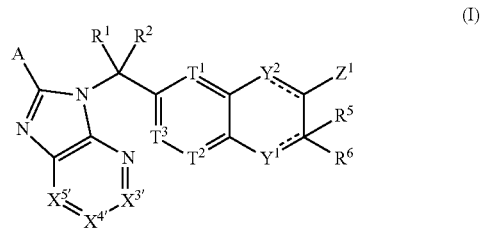

(I)

and/or stereoisomers, optical isomers, racemic and diastereomeric mixtures, and/or pharmaceutically acceptable salts thereof, wherein:
the dashed lines represent optional double bonds;
A is selected from H and D;
X$^{3'}$ is CR$^{3'}$ wherein R$^{3'}$ is selected from H and D;
X$^{4'}$ is CR$^{4'}$ wherein R$^{4'}$ is selected from H, D, and R$^7$; and
X$^{5'}$ is CR$^{5'}$ wherein R$^{5'}$ is selected from H and D, wherein at least one of A, $R^{3'}$, $R^{4'}$, and $R^{5'}$ is D.

In at least one embodiment of the disclosure, the compounds according to Formula (I') are such that $R^1$ and $R^2$ are each independently selected from H and D. In at least one embodiment of the disclosure, the compounds according to Formula (I') are such that $R^6$ is selected from $(C_3\text{-}C_{10})$ cycloalkyl, $(C_2\text{-}C_9)$heteroaryl, $R^{14}$—$(C_6\text{-}C_{14})$aryl, $R^{14}$—$(C_2\text{-}C_9)$heteroaryl, and $R^{14}$—$(C_1\text{-}C_{10})$alkylamine; wherein $R^{14}$ is each independently selected from H, $(C_1\text{-}C_{10})$alkyl, $(C_1\text{-}C_{10})$alkylamine, $(C_1\text{-}C_{10})$alkoxy-, HO—, $F_2HC$—O—, $F_3C$—C(O)—, $F_3C$—, and $F_2HC$—; and wherein each $(C_1$-$C_{10})$alkyl, $(C_6\text{-}C_{14})$aryl, $(C_2\text{-}C_9)$heteroaryl, $(C_3\text{-}C_{10})$cycloalkyl, or $(C_2\text{-}C_9)$heterocycloalkyl are further optionally substituted by one to four groups selected from $(C_1\text{-}C_{10})$alkyl, HO—, halo, or $H_2N$—.

In another aspect, the disclosure related to the compounds of Table A, and/or stereoisomers, optical isomers, racemic and diastereomeric mixtures, and/or pharmaceutically acceptable salts thereof:

TABLE A

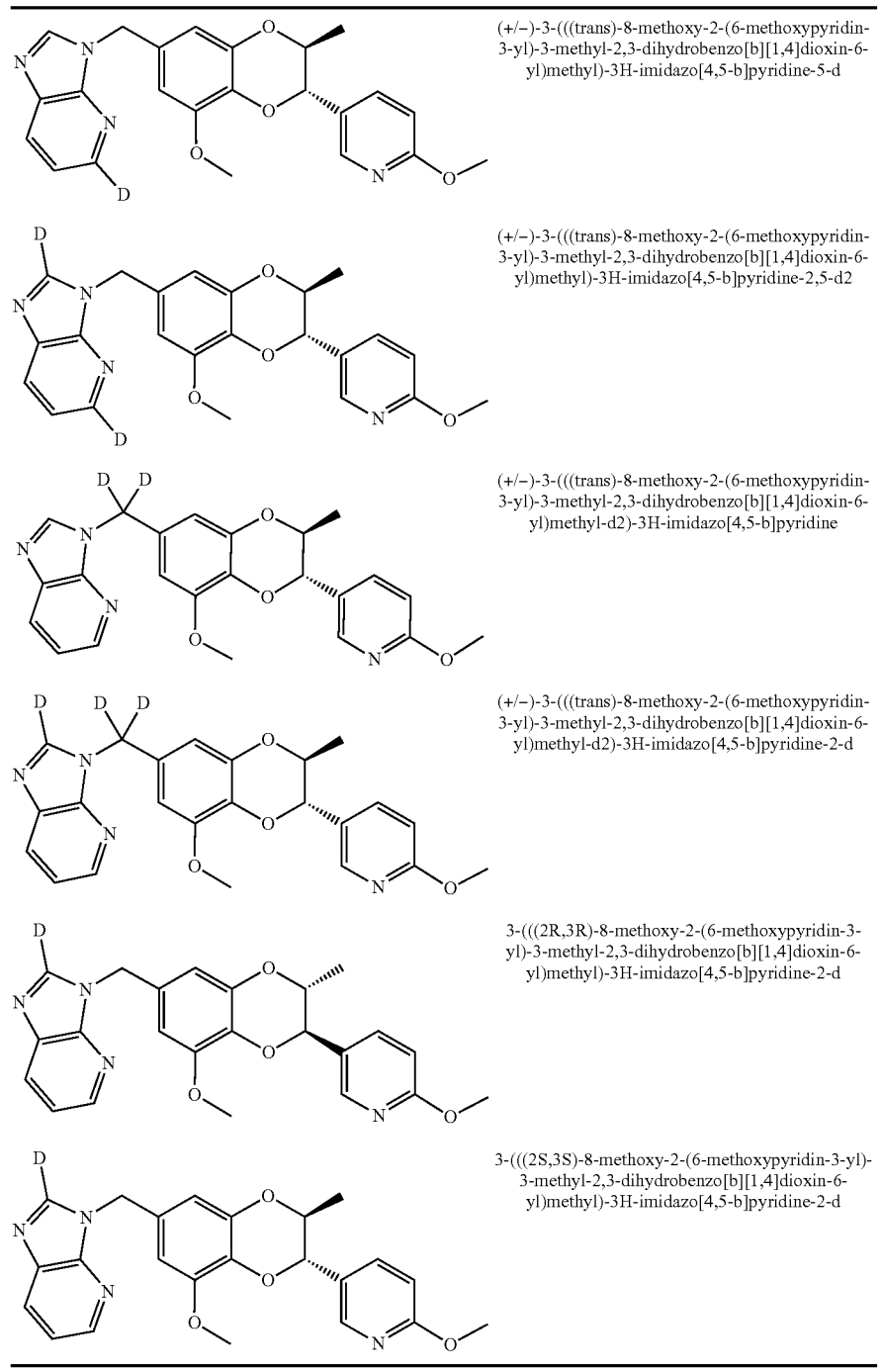

(+/−)-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-5-d (+/−)-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-2,5-d2

(+/−)-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine (+/−)-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine-2-d 3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d In at least one embodiment of the disclosure, the compound is selected from 3-(((2S,3S)-8-methoxy-2-(6- methoxypyridin-3-yl)-3-methyl-2,3-dihydrobenzo[b][1,4] dioxin-6-yl)methyl)-3H-imidazo[4,5-b]pyridine-2-d and/or stereoisomers, optical isomers, racemic and diastereomeric mixtures, and/or pharmaceutically acceptable salts thereof. In at least one embodiment of the disclosure, the compound is 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d.

Another aspect of the disclosure is a pharmaceutical composition comprising a pharmaceutically acceptable excipient and a compound of Formula (I), and/or stereoisomers, optical isomers, racemic and diastereomeric mixtures, and/or pharmaceutically acceptable salts thereof. In at least one embodiment, the pharmaceutical composition comprises a compound of Formula (I) and/or a pharmaceutically acceptable salt thereof.

Another aspect of the disclosure is a pharmaceutical composition comprising a pharmaceutically acceptable excipient and at least one compound of Formula (I'), and/or stereoisomers, optical isomers, racemic and diastereomeric mixtures, and/or pharmaceutically acceptable salts thereof. In at least one embodiment, the pharmaceutical composition comprises a compound of Formula (I') and/or a pharmaceutically acceptable salt thereof.

Another aspect of the disclosure is a pharmaceutical composition comprising a pharmaceutically acceptable excipient and a compound of Table A, and/or stereoisomers, optical isomers, racemic and diastereomeric mixtures, and/or pharmaceutically acceptable salts thereof. In at least one embodiment, the pharmaceutical composition comprises a compound of Table A and/or a pharmaceutically acceptable salt thereof. In an aspect of the disclosure, the pharmaceutical composition comprises 3-(((2S,3S)-8-methoxy-2-(6-methoxypyridin-3-yl)-3-methyl-2,3-dihydrobenzo[b][1,4] dioxin-6-yl)methyl)-3H-imidazo[4,5-b]pyridine-2-d and/or stereoisomers, optical isomers, racemic and diastereomeric mixtures, and/or pharmaceutically acceptable salts thereof. In an aspect of the disclosure, the pharmaceutical composition comprises 3-(((2S,3S)-8-methoxy-2-(6-methoxypyridin-3-yl)-3-methyl-2,3-dihydrobenzo[b][1,4]dioxin-6-yl) methyl)-3H-imidazo[4,5-b]pyridine-2-d Form A.

Another aspect of the disclosure is a method of treating a disease or disorder, such as neurological and immune mediated diseases, in a subject in need thereof comprising administering a therapeutically effective amount of a compound of Formula (I), and/or stereoisomers, optical isomers, racemic and diastereomeric mixtures, and/or pharmaceutically acceptable salts thereof as described herein. In at least one embodiment, the method comprises administering a therapeutically effective amount of a compound of Formula (I'), and/or stereoisomers, optical isomers, racemic and diastereomeric mixtures, and/or pharmaceutically acceptable salts thereof as described herein. In at least one embodiment, the method comprises administering a therapeutically effective amount of a compound of Table A, and/or stereoisomers, optical isomers, racemic and diastereomeric mixtures, and/or pharmaceutically acceptable salts thereof as described herein. In an aspect of the disclosure, the pharmaceutical composition comprises 3-(((2S,3S)-8-methoxy-2-(6-methoxypyridin-3-yl)-3-methyl-2,3-dihydrobenzo[b] [1,4]dioxin-6-yl)methyl)-3H-imidazo[4,5-b]pyridine-2-d and/or stereoisomers, optical isomers, racemic and diastereomeric mixtures, and/or pharmaceutically acceptable salts thereof. In an aspect of the disclosure, the pharmaceutical composition comprises 3-(((2S,3S)-8-methoxy-2-(6-methoxypyridin-3-yl)-3-methyl-2,3-dihydrobenzo[b][1,4] dioxin-6-yl)methyl)-3H-imidazo[4,5-b]pyridine-2-d Form A.

Another aspect of the disclosure is a method of treating a disease or disorder, such as neurological and immune mediated diseases, in a subject in need thereof comprising administering a pharmaceutical composition comprising a therapeutically effective amount of a compound of Formula (I), and/or stereoisomers, optical isomers, racemic and diastereomeric mixtures, and/or pharmaceutically acceptable salts thereof as described herein. In at least one embodiment, the method comprises administering a pharmaceutical composition comprising a therapeutically effective amount of a compound of Formula (I'), and/or stereoisomers, optical isomers, racemic and diastereomeric mixtures, and/or pharmaceutically acceptable salts thereof as described herein. In at least one embodiment, the method comprises administering a therapeutically effective amount of a pharmaceutical composition comprising a compound of Table A, and/or stereoisomers, optical isomers, racemic and diastereomeric mixtures, and/or pharmaceutically acceptable salts thereof as described herein. In an aspect of the disclosure, the method comprises administering a therapeutically effective amount of a pharmaceutical composition comprising 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d and/or stereoisomers, optical isomers, racemic and diastereomeric mixtures, and/or pharmaceutically acceptable salts thereof and/or pharmaceutically acceptable salts thereof as described herein. In an aspect of the disclosure, the method comprises administering a therapeutically effective amount of a pharmaceutical composition comprising 3-(((2S,3S)-8-methoxy-2-(6-methoxypyridin-3-yl)-3-methyl-2,3-dihydrobenzo[b][1,4] dioxin-6-yl)methyl)-3H-imidazo[4,5-b]pyridine-2-d Form A and/or pharmaceutically acceptable salts thereof as described herein.

In another aspect, the present disclosure provides a compound of Formula (I), and/or stereoisomers, optical isomers, racemic and diastereomeric mixtures, and/or pharmaceutically acceptable salts thereof as described herein for use as a medicament. In at least one embodiment, the compound of Formula (I), and/or stereoisomers, optical isomers, racemic and diastereomeric mixtures, and/or pharmaceutically acceptable salts thereof as described herein for use as a medicament is a compound of Formula (I'), and/or stereoisomers, optical isomers, racemic and diastereomeric mixtures, and/or pharmaceutically acceptable salts thereof as described herein. In at least one embodiment, the compound of Formula (I), and/or stereoisomers, optical isomers, racemic and diastereomeric mixtures, and/or pharmaceutically acceptable salts thereof as described herein for use as a medicament is a compound of Table A, and/or stereoisomers, optical isomers, racemic and diastereomeric mixtures, and/or pharmaceutically acceptable salts thereof as described herein. In at least one embodiment, the compound of Formula (I), and/or stereoisomers, optical isomers, racemic and diastereomeric mixtures, and/or pharmaceutically acceptable salts thereof as described herein for use as a medicament is a compound selected from 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b] pyridine-2-d and/or stereoisomers, optical isomers, racemic and diastereomeric mixtures, and/or pharmaceutically acceptable salts thereof. In an aspect of the disclosure, the compound comprises 3-(((2S,3S)-8-methoxy-2-(6-methoxypyridin-3-yl)-3-methyl-2,3-dihydrobenzo[b][1,4]

dioxin-6-yl)methyl)-3H-imidazo[4,5-b]pyridine-2-d and/or stereoisomers, optical isomers, racemic and diastereomeric mixtures, and/or pharmaceutically acceptable salts thereof and/or pharmaceutically acceptable salts thereof as described herein. In an aspect of the disclosure, the compound comprises 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d Form A and/or pharmaceutically acceptable salts thereof as described herein.

In another aspect, the present disclosure provides a compound of Formula (I), and/or stereoisomers, optical isomers, racemic and diastereomeric mixtures, and/or pharmaceutically acceptable salts thereof as described herein for use in the treatment of a disease or disorder, such as neurological and immune mediated diseases, in a subject in need thereof. In at least one embodiment, the compound of Formula (I), and/or stereoisomers, optical isomers, racemic and diastereomeric mixtures, and/or pharmaceutically acceptable salts thereof as described herein for use in the treatment of a disease or disorder, such as neurological and immune mediated diseases, in a subject in need thereof, is a compound of Formula (I'), and/or stereoisomers, optical isomers, racemic and diastereomeric mixtures, and/or pharmaceutically acceptable salts thereof as described herein. In at least one embodiment, the compound of Formula (I), and/or stereoisomers, optical isomers, racemic and diastereomeric mixtures, and/or pharmaceutically acceptable salts thereof as described herein for use in the treatment of a disease or disorder, such as neurological and immune mediated diseases, in a subject in need thereof, is a compound of Table A, and/or stereoisomers, optical isomers, racemic and diastereomeric mixtures, and/or pharmaceutically acceptable salts thereof as described herein. In at least one embodiment, the compound of Formula (I), and/or stereoisomers, optical isomers, racemic and diastereomeric mixtures, and/or pharmaceutically acceptable salts thereof as described herein for use in the treatment of a disease or disorder, such as neurological and immune mediated diseases, in a subject in need thereof, is a compound selected from 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d and/or stereoisomers, optical isomers, racemic and diastereomeric mixtures, and/or pharmaceutically acceptable salts thereof. In an aspect of the disclosure, the compound comprises 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d and/or stereoisomers, optical isomers, racemic and diastereomeric mixtures, and/or pharmaceutically acceptable salts thereof and/or pharmaceutically acceptable salts thereof as described herein. In an aspect of the disclosure, the compound comprises 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d Form A and/or pharmaceutically acceptable salts thereof as described herein.

In some aspects of the disclosure, the neurological and immune mediated diseases include multiple sclerosis, ALS, MSA, PSP, Huntington's disease, lupus, lupus nephritis, and rheumatoid arthritis.

In vitro and in vivo effects of the deuterated CSF-1R inhibitors, their ability to withstand metabolic degradation, and methods of preparing select deuterated CSF-1R inhibitors of the disclosure are described in the Examples.

Although specific embodiments of this disclosure will now be described with reference to the preparations and schemes, it should be understood that such embodiments are by way of example only and merely illustrative of but a small number of the many possible specific embodiments which can represent applications of the principles of this disclosure. Various changes and modifications will be obvious to those of skill in the art given the benefit of this disclosure and are deemed to be within the spirit and scope of this disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

As used herein, the term "amino" means a functional group having a nitrogen atom and 1 to 2 hydrogen atoms. "Amino" generally may be used herein to describe a primary, secondary, or tertiary amine, and those of skill in the art will readily be able to ascertain the identification of which in view of the context in which this term is used in this disclosure. The term "amine" or "amine group" or "ammonia group" means a functional group containing a nitrogen atom derived from ammonia ($NH_3$). The amine groups are preferably primary amines, meaning the nitrogen is bonded to two hydrogen atoms and one substituent group comprising a substituted or unsubstituted alkyl or aryl group or an aliphatic or aromatic group. The amine groups may be secondary amines meaning, the nitrogen is bonded to one hydrogen atom and two substituent groups comprising a substituted or unsubstituted alkyl or aryl groups or an aliphatic or aromatic group, as defined below. The amine groups may be tertiary amines meaning the nitrogen is bonded to three substituent groups comprising a substituted or unsubstituted alkyl or aryl groups or an aliphatic or aromatic group. The amine groups may also be quaternary amines meaning the designated amine group is bonded to a fourth group, resulting in a positively charged ammonium group.

It is understood that any or all of the amines in this disclosure may be in the free amine form (that is, as $-NH_2$ for a primary amine) or in a protonated form with a pharmaceutically acceptable anion (that is, as $-NH_3^+$ $Y^-$ for a primary amine, where $Y^-$ is the pharmaceutically acceptable anion).

As used herein, the term "amide group" means a functional group comprising a carbonyl group linked to a nitrogen.

As used herein "carbonyl group" means a functional group comprising a carbon atom double bonded to an oxygen atom, represented by (C=O).

As used herein, the term "alkane" means a saturated hydrocarbon, bonded by single bonds. Alkanes can be linear or branched. "Cycloalkanes" are saturated hydrocarbons rings bonded by single bonds.

As used herein, the term "$(C_1-C_{10})$alkyl" means a saturated straight chained or branched or cyclic hydrocarbon consisting essentially of 1 to 10 carbon atoms and a corresponding number of hydrogen atoms. Typically, straight chain or branched groups have from one to ten carbons, or more typically one to five carbons. Exemplary $(C_1-C_{10})$alkyl groups include methyl (represented by $-CH_3$), ethyl (represented by $-CH_2-CH_3$), n-propyl, isopropyl, n-butyl, isobutyl, etc. Other $(C_1-C_{10})$alkyl groups will be readily apparent to those of skill in the art given the benefit of this disclosure.

As used herein, the term "$(C_2$-$C_9)$heteroalkyl" means a saturated straight chained or branched or cyclic hydrocarbon consisting essentially of 2 to 10 atoms, wherein 2 to 9 of the atoms are carbon and the remaining atom(s) is selected from the group consisting of nitrogen, sulfur, and oxygen. Exemplary $(C_2$-$C_9)$heteroalkyl groups will be readily apparent to those of skill in the art given the benefit of this disclosure.

As used herein, the term "$(C_3$-$C_{10})$cycloalkyl" means a nonaromatic saturated hydrocarbon group, forming at least one ring consisting essential of 3 to 10 carbon atoms and a corresponding number of hydrogen atoms. $(C_3$-$C_{10})$cycloalkyl groups can be monocyclic or multicyclic. Individual rings of multicyclic cycloalkyl groups can have different connectivities, for example, fused, bridged, spiro, etc., in addition to covalent bond substitution. Exemplary $(C_3$-$C_{10})$ cycloalkyl groups include cyclopropyl, cyclobutyl, cyclopentyl, cyclohexyl, norbornanyl, bicyclo-octanyl, octahydro-pentalenyl, spiro-decanyl, cyclopropyl substituted with cyclobutyl, cyclobutyl substituted with cyclopentyl, cyclohexyl substituted with cyclopropyl, etc. Other $(C_3$-$C_{10})$ cycloalkyl groups will be readily apparent to those of skill in the art given the benefit of this disclosure.

As used herein, the term "$(C_2$-$C_9)$heterocycloalkyl" means a nonaromatic group having 3 to 10 atoms that form at least one ring, wherein 2 to 9 of the ring atoms are carbon and the remaining ring atom(s) is selected from the group consisting of nitrogen, sulfur, and oxygen. $(C_2$-$C_9)$heterocycloalkyl groups can be monocyclic or multicyclic. Individual rings of such multicyclic heterocycloalkyl groups can have different connectivities, for example, fused, bridged, spiro, etc., in addition to covalent bond substitution. Exemplary $(C_2$-$C_9)$heterocycloalkyl groups include pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo [4.1.0]heptanyl, 3-azabicyclo[3.1.0]hexanyl, 2-azaspiro [4.4]nonanyl, 7-oxa-1-aza-spiro[4.4]nonanyl, 7-azabicyclo [2.2.2]heptanyl, octahydro-1H-indolyl, etc. The $(C_2$-$C_9)$ heterocycloalkyl group is typically attached to the main structure via a carbon atom or a nitrogen atom. Other $(C_2$-$C_9)$heterocycloalkyl groups will be readily apparent to those of skill in the art given the benefit of this disclosure.

The term "aliphatic group" or "aliphatic" means a non-aromatic group consisting of carbon and hydrogen, and may optionally include one or more double and/or triple bonds. In other words, an aliphatic group is any group consisting of carbon and hydrogen which contains no aromatic functionality. An aliphatic group may be straight chained, branched or cyclic and typically contains between about one and about 24 carbon atoms.

The term "aryl group" may be used interchangeably with "aryl," "aryl ring," "aromatic," "aromatic group," and "aromatic ring." Aryl groups include carbocyclic aromatic groups, typically with six to fourteen ring carbon atoms. Aryl groups also include heteroaryl groups, which typically have five to fourteen ring atoms with one or more heteroatoms selected from nitrogen, oxygen and sulfur.

As used herein, the term "$(C_6$-$C_{14})$aryl" means an aromatic functional group having 6 to 14 carbon atoms that form at least one ring.

As used herein, the term "$(C_2$-$C_9)$heteroaryl" means an aromatic functional group having 5 to 10 atoms that form at least one ring, wherein 2 to 9 of the ring atoms are carbon and the remaining ring atom(s) is selected from the group consisting of nitrogen, sulfur, and oxygen. $(C_2$-$C_9)$heteroaryl groups can be monocyclic or multicyclic. Individual rings of such multicyclic heteroaryl groups can have different connectivities, for example, fused, etc., in addition to covalent bond substitution. Exemplary $(C_2$-$C_9)$heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2, 4-triazinyl, 1,2,3-triazinyl, 1,3,5-triazinyl, pyrazolo[3,4-b] pyridinyl, cinnolinyl, pteridinyl, purinyl, 6,7-dihydro-5H-[1]pyrindinyl, benzo[b]thiophenyl, 5,6,7,8-tetrahydroquinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. The $(C_2$-$C_9)$heteroaryl group is typically attached to the main structure via a carbon atom, however, those of skill in the art will realize when certain other atoms, for example, hetero ring atoms, can be attached to the main structure. Other $(C_2$-$C_9)$heteroaryl groups will be readily apparent to those of skill in the art given the benefit of this disclosure.

The term "alkynyl" means a functional group containing triple bonded carbons, represented by $(C_2$-$C_{10})$alkynyl-.

As used herein, the term "alkylamine" means an $(C_1$-$C_{10})$ alkyl containing a primary, secondary, or tertiary amine group in place of one hydrogen atom, represented by $(C_1$-$C_{10})$alkyl amine and $((C_1$-$C_{10})$alkyl)2 amine.

The term "alkynylamine" means a $(C_2$-$C_{10})$ group containing triple bonded carbons and an amine group, represented by $(C_2$-$C_{10})$alkynylamine.

The term "alkoxy" means a $(C_1$-$C_{10})$alkyl bound to an oxygen, represented by $(C_1$-$C_{10})$alkyl-O— or $(C_1$-$C_{10})$ alkoxy-. The term "alkoxyalkyl" means a $(C_1$-$C_{10})$alkyl bound to an oxygen bound to another $(C_1$-$C_{10})$alkyl, represented by $(C_1$-$C_{10})$alkyl-O—$(C_1$-$C_{10})$alkyl- or $(C_1$-$C_{10})$ alkoxy-$(C_1$-$C_{10})$alkyl-.

The term "alkyl ester" means a $(C_1$-$C_{10})$alkyl containing an ester group in place of one hydrogen atom, represented by —O(O)C—$(C_1$-$C_{10})$alkyl.

The term "alkyl acid" means an $(C_1$-$C_{10})$alkyl containing a carboxylic acid group in place of one hydrogen atom, represented by $(C_1$-$C_{10})$alkyl-COOH.

The term "aliphatic acid" means an acid of nonaromatic hydrocarbons, represented by $(C_1$-$C_{10})$alkyl-COOH and $(C_3$-$C_{10})$cycloalkyl-COOH.

As used herein, "D" and "d" both refer to deuterium.

The term "dicarbonyl" refers to an organic molecule containing two or more adjacent carbonyl groups. Carbonyl groups, represented by C=O, can be, for example, aldehydes, ketones, and other groups with an oxygen atom doubly bonded to a carbon atom. Examples include glyoxal, methylglyoxal, dimethyl glyoxal, and 3-deoxyglucosone.

The term "halo" or "Hal" means a fluorine (F), chlorine (Cl), bromine (Br), iodine (I), or astatine (At) ion.

As used herein, "i-" refers to iso.

The term "methoxy" means a $(C_1)$alkyl containing an oxygen in place of one hydrogen atom, represented by —(O)CH$_3$.

As used herein, "n-" refers to normal.

The term "polyol" means an alcohol containing multiple hydroxyl (—OH) groups.

As used herein, "Sec" or "s-" each refer to secondary.

As used herein, the term "Stereoisomer" refers to both enantiomers and diastereomers.

"Substituted" means the substitution of a carbon in alkyl, heterocyclic or aryl groups with one or more non-carbon substituents. Non-carbon substituents are selected from nitrogen, oxygen and sulfur.

As used herein, "Tert" and "t-" each refer to tertiary.

"Unsubstituted" means the group is comprised of only hydrogen and carbon.

A 3 to 10-member ring means a closed ring; the 3 to 10-member ring may be acyclic, aromatic or heterocyclic.

The term "pharmaceutically acceptable anion" means an anion that is suitable for pharmaceutical use. Pharmaceutically acceptable anions include halides, carbonate, bicarbonate, sulfate, bisulfate, hydroxide, nitrate, persulfate, phosphate, sulfite, acetate, ascorbate, benzoate, citrate, dihydrogen citrate, hydrogen citrate, oxalate, succinate, tartrate, taurocholate, glycocholate, and cholate.

"Substituted with deuterium" refers to the replacement of one or more hydrogen atoms with a corresponding number of deuterium atoms.

All pharmaceutically acceptable salts, prodrugs, tautomers, hydrates and solvates of the compounds presently disclosed are also within the scope of this disclosure.

Presently disclosed compounds that are basic in nature are generally capable of forming a wide variety of different salts with various inorganic and/or organic acids. Although such salts are generally pharmaceutically acceptable for administration to animals and humans, it is often desirable in practice to initially isolate a compound from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds can be readily prepared using conventional techniques, e.g., by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained.

Acids which can be used to prepare the pharmaceutically acceptable acid addition salts of the base compounds are those which can form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Presently disclosed compounds that are acidic in nature, e.g., contain a COOH or tetrazole moiety, are generally capable of forming a wide variety of different salts with various inorganic and/or organic bases. Although such salts are generally pharmaceutically acceptable for administration to animals and humans, it is often desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations, and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before. In either case, stoichiometric quantities of reagents are preferably employed to ensure completeness of reaction and maximum product yields of the desired solid salt.

Bases which can be used to prepare the pharmaceutically acceptable base addition salts of the base compounds are those which can form non-toxic base addition salts, i.e., salts containing pharmacologically acceptable cations, such as, alkali metal cations (e.g., potassium and sodium), alkaline earth metal cations (e.g., calcium and magnesium), ammonium or other water-soluble amine addition salts such as N-methylglucamine-(meglumine), lower alkanolammonium and other such bases of organic amines.

Stereoisomers (e.g., cis- and trans-isomers) and all optical isomers of a presently disclosed compound (e.g., R and S enantiomers), as well as racemic, diastereomeric and other mixtures of such isomers are within the scope of this disclosure.

The compounds, salts, prodrugs, hydrates, and solvates presently disclosed can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, all tautomers are within the scope of this disclosure.

Atropisomers are also within the scope of this disclosure. Atropisomers refer to compounds that can be separated into rotationally restricted isomers.

This disclosure also provides pharmaceutical compositions comprising at least one presently disclosed compound and at least one pharmaceutically acceptable carrier. The pharmaceutically acceptable carrier can be any such carrier known in the art including those described in, for example, Remington's Pharmaceutical Sciences, Mack Publishing Co., (A. R. Gennaro, ed. 1985.) Pharmaceutical compositions of the compounds presently disclosed may be prepared by conventional means known in the art including, for example, mixing at least one presently disclosed compound with a pharmaceutically acceptable carrier.

Presently disclosed pharmaceutical compositions can be used in an animal or human. Thus, a presently disclosed compound can be formulated as a pharmaceutical composition for oral, buccal, parenteral (e.g., intravenous, intramuscular or subcutaneous), topical, rectal or intranasal administration or in a form suitable for administration by inhalation or insufflation.

The compounds presently disclosed may also be formulated for sustained delivery according to methods well known to those of ordinary skill in the art. Examples of such formulations can be found in U.S. Pat. Nos. 3,119,742; 3,492,397; 3,538,214; 4,060,598; and 4,173,626.

For oral administration, the pharmaceutical composition may take the form of, for example, a tablet or capsule prepared by conventional means with a pharmaceutically acceptable excipient(s) such as a binding agent (e.g., pregelatinized maize starch, polyvinylpyrrolidone or hydroxypropyl methylcellulose); filler (e.g., lactose, microcrystalline cellulose or calcium phosphate); lubricant (e.g., magnesium stearate, talc or silica); disintegrant (e.g., potato starch or sodium starch glycolate); and/or wetting agent (e.g., sodium lauryl sulphate). The tablets may be coated by methods well known in the art. Liquid preparations for oral administration may take the form of a, for example, solution, syrup or suspension, or they may be presented as a dry product for constitution with water or other suitable vehicle before use. Such liquid preparations may be prepared by conventional means with a pharmaceutically acceptable additive(s) such as a suspending agent (e.g., sorbitol syrup, methyl cellulose or hydrogenated edible fats); emulsifying agent (e.g., lecithin or acacia); non-aqueous vehicle (e.g., almond oil, oily esters or ethyl alcohol); and/or preservative (e.g., methyl or propyl p-hydroxybenzoates or sorbic acid.)

A proposed dose of a presently disclosed compound for oral, parenteral or buccal administration to the average adult human for the treatment or prevention of a CSF-1R-related disease state is about 0.1 mg to about 2000 mg. In certain embodiments, the proposed dose is from about 0.1 mg to about 200 mg of the active ingredient per unit dose. Irrespective of the amount of the proposed dose, administration of the compound can occur, for example, 1 to 4 times per day.

Pharmaceutical compositions and methods of treatment or prevention comprising administering prodrugs of at least one presently disclosed compound are also within the scope of this disclosure.

Non-limiting examples of suitable CSF-1R inhibitors according to Formula (I) and Formula (I') are presented in the Examples below. It is understood that any or all of the amines of the structures presented in inhibitors according to Formula (I) and Formula (I') are presented in the Examples below may be in the free amine form or in a protonated form with a pharmaceutically acceptable anion. Preferred pharmaceutically acceptable anions include halides, carbonate, bicarbonate, sulfate, bisulfate, hydroxide, nitrate, persulfate, phosphate, sulfite, acetate, ascorbate, benzoate, citrate, dihydrogen citrate, hydrogen citrate, oxalate, succinate, tartrate, taurocholate, glycocholate, and cholate. Most preferred pharmaceutically acceptable anions include chloride, carbonate, and bicarbonate. It is also understood that any or all of the CSF-1R inhibitors according to Formula (I) and Formula (I') may be the racemate or an enantiomer of the racemate.

EXAMPLES

Example 1

Methods of Synthesis

The synthesis of compounds of Formula I may be readily achieved by synthetic chemists of skill in the art by reference to the preparations, schemes, and Examples referenced and disclosed herein. Relevant preparations, schemes, and procedures analogous to those of use for the preparation of compounds of Formula I and intermediates thereof are disclosed in the general schemes and synthetic Examples of WO2017/015267. The specific embodiments of this disclosure are described with reference to the synthetic preparations and schemes presented below; it should be understood that such embodiments are by way of example only and merely illustrative of but a small number of the many possible specific embodiments which can represent applications of the principles of this disclosure. Various changes and modifications to the preparations, schemes and examples will be obvious to those of skill in the art given the benefit of this disclosure.

Synthetic Examples (Examples 1-9)

Example 1

Synthesis of (+/−)-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-5-d (Compound 1)

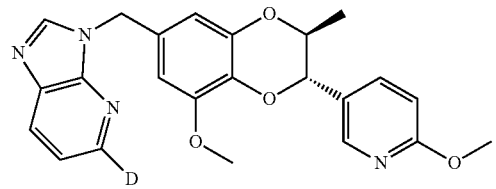 [SMILES: [2H]c1ccc2ncn(Cc3cc(OC)c4c(c3)O[C@@H](C)[C@H](c3ccc(OC)nc3)O4)c2n1]

Example 1-1

Preparation of (+/−)-methyl (trans)-8-methoxy-2-(6-methoxypyridin-3-yl)-3-methyl-2,3-dihydrobenzo[b][1,4]dioxine-6-carboxylate

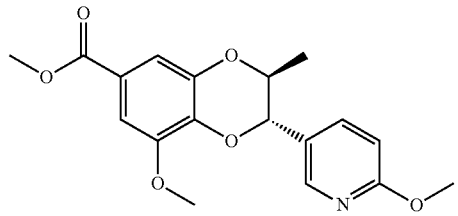

To a stirred solution of methyl 4-hydroxy-3-((1-hydroxy-1-(6-methoxypyridin-3-yl)propan-2-yl)oxy)-5-methoxybenzoate (1.41 g, 3.88 mmol, see WO2017015267 for preparation), triphenylphosphine (1.23 g, 4.66 mmol), and N,N-diisopropylethylamine (1.0 mL, 5.82 mmol) in acetonitrile (30 mL) was added carbon tetrachloride (1.9 mL, 19.40 mmol). The resulting colorless solution was heated to reflux and was stirred under an inert atmosphere. After 45 min, LC/MS analysis revealed that the reaction was complete. The mixture was cooled to room temperature and was concentrated to provide a tan solid. Chromatographic purification (CombiFlash, 80 g $SiO_2$ gold column, 10-30% ethyl acetate/heptane elute) afforded (+/−)-methyl (trans)-8-methoxy-2-(6-methoxypyridin-3-yl)-3-methyl-2,3-dihydrobenzo[b][1,4]dioxine-6-carboxylate (0.75 g, 2.18 mmol, 56% yield) as a white solid: $^1$H NMR (400 MHz, $CDCl_3$) δ 8.19 (d, J=2.4 Hz, 1H), 7.59 (dd, J=8.6, 2.4 Hz, 1H), 7.34 (d, J=1.9 Hz, 1H), 7.23 (d, J=1.9 Hz, 1H), 6.80 (d, J=8.6 Hz, 1H), 4.70 (d, J=7.8 Hz, 1H), 4.15 (dq, J=7.8, 6.4 Hz, 1H), 3.96 (s, 3H), 3.90 (s, 6H), 1.22 (d, J=6.4 Hz, 3H) ppm; (M+1)=346.

Example 1-2

Preparation of (+/−)-((trans)-8-methoxy-2-(6-methoxypyridin-3-yl)-3-methyl-2,3-dihydrobenzo[b][1,4]dioxin-6-yl)methanol

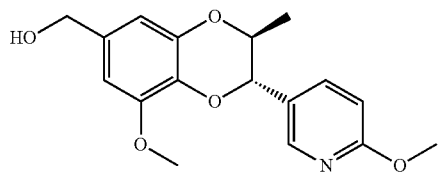 [SMILES: COc1ccc([C@@H]2Oc3c(OC)cc(CO)cc3O[C@H]2C)cn1]

To a stirred 0° C. solution of (+/−)-methyl trans-8-methoxy-2-(6-methoxypyridin-3-yl)-3-methyl-2,3-dihydrobenzo [b][1,4]dioxine-6-carboxylate (0.75 g, 2.18 mmol) in tetrahydrofuran (30 ml) was added lithium aluminum hydride (0.12 g, 3.27 mmol) in one portion (minor evolution of gas noted). The resulting gray mixture was stirred at 0° C. under an inert atmosphere. After 10 min, LC/MS analysis revealed that the reaction was complete. The mixture was quenched by the addition of water (0.12 mL), 1N sodium hydroxide solution (0.12 mL), and water (0.38 mL). The resulting mixture was stirred at 0° C. for 10 minutes, and then magnesium sulfate (ca. 5 g) was added. The mixture was filtered through Celite, and the filter cake was washed with ethyl acetate (50 mL). The filtrate was concentrated to provide (+/−)-((trans)-8-methoxy-2-(6-methoxypyridin-3-yl)-3-methyl-2,3-dihydrobenzo[b][1,4]dioxin-6-yl)methanol (0.69 g, 2.18 mmol, 100% yield) as a sticky white foam: $^1$H NMR (400 MHz, DMSO-d6) δ 8.26 (d, J=2.3 Hz, 1H), 7.77 (dd, J=8.5, 2.3 Hz, 1H), 6.89 (d, J=8.5 Hz, 1H), 6.55 (d, J=1.9 Hz, 1H), 6.49 (d, J=1.9 Hz, 1H), 5.09 (br s, 1H), 4.74 (d, J=7.7 Hz, 1H), 4.38 (s, 2H), 4.31 (dq, J=7.7, 6.3 Hz, 1H), 3.88 (s, 3H), 3.72 (s, 3H), 1.09 (d, J=6.3 Hz, 3H); (M+1)=318.

Example 1-3

Preparation of (+/−)-5-bromo-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine

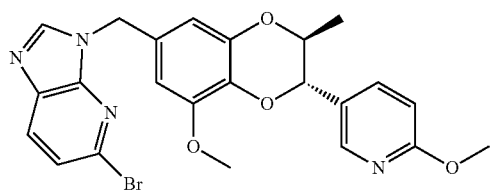 [SMILES: COc1ccc([C@@H]2Oc3c(OC)cc(Cn4cnc5ccc(Br)nc54)cc3O[C@H]2C)cn1]

To a stirred solution of 5-bromo-1H-imidazo[4,5-b]pyridine (0.21 g, 0.99 mmol) and (+/−)-((trans)-8-methoxy-2-(6-methoxypyridin-3-yl)-3-methyl-2,3-dihydrobenzo[b][1,4]dioxin-6-yl)methanol (0.35 g, 1.10 mmol) in toluene (10 ml) was added (tributylphosphoranylidene)acetonitrile (0.43 g, 1.74 mmol). The resulting mixture was heated to 75° C. in a sealed vessel and was allowed to stir. After 18 h, LC/MS analysis revealed that the reaction was complete. The mixture was cooled to room temperature and was concentrated to provide a brown oil. Chromatographic purification (CombiFlash, 40 g SiO$_2$ gold column, 20-60% 3:1 ethyl acetate:ethanol/heptane elute) afforded (+/−)-5-bromo-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine (0.33 g, 0.67 mmol, 67% yield) as a tan solid: $^1$H NMR (400 MHz, DMSO-d6) δ 8.61 (s, 1H), 8.23 (d, J=2.3 Hz, 1H), 8.08 (d, J=8.3 Hz, 1H), 7.73 (dd, J=8.6, 2.3 Hz, 1H), 7.49 (d, J=8.3 Hz, 1H), 6.88 (d, J=8.6 Hz, 1H), 6.79 (d, J=1.9 Hz, 1H), 6.46 (d, J=1.9 Hz, 1H), 5.36 (s, 2H), 4.73 (d, J=7.8 Hz, 1H), 4.29 (dq, J=7.8, 6.3 Hz, 1H), 3.87 (s, 3H), 3.73 (s, 3H), 1.05 (d, J=6.3 Hz, 3H) ppm; (M+1)=497. Confirmation of regiochemistry: $^1$H-$^{13}$C HSQC NMR data identified the imidazole C-2 proton and carbon at 8.61 and 145.8 ppm respectively. Next, $^1$H-$^{13}$C HMBC NMR data showed multiple-bond correlations between this proton at 8.61 ppm and the quaternary ring carbons 134.1 and 146.4 ppm with the carbon at 146.4 ppm being adjacent to the pyridine nitrogen. Lastly, connection was confirmed by a $^1$H-$^{13}$C multiple bond correlation between the adjacent methylene protons at 5.36 ppm and the quaternary carbons at 145.8 ppm and 146.4 ppm evident in the HMBC NMR data.

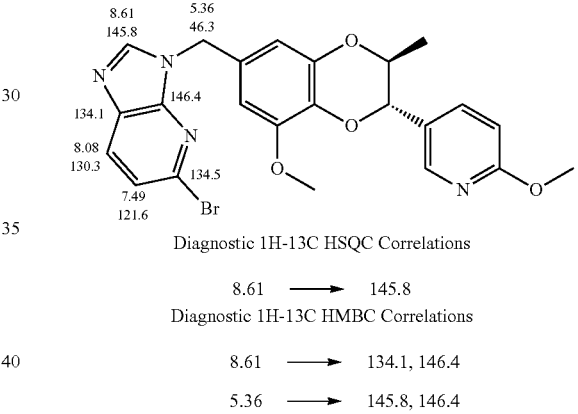

Diagnostic 1H-13C HSQC Correlations 8.61 ⟶ 145.8

Diagnostic 1H-13C HMBC Correlations 8.61 ⟶ 134.1, 146.4

5.36 ⟶ 145.8, 146.4

Example 1-4

Preparation of (+/−)-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-5-d To an stirred solution (note: conducted in a 20 mL oven-dried microwave reaction vessel) of (+/−)-5-bromo-trans-3-((-8-methoxy-2-(6-methoxypyridin-3-yl)-3-methyl-2,3-dihydrobenzo[b][1,4]dioxin-6-yl)methyl)-3H-imidazo[4,5-b]pyridine (0.53 mg, 1.06 mmol) in 2-propanol-d8 (5 mL) was added tris(dibenzylideneacetone)dipalladium(0) (0.19 g, 0.21 mmol), 2-dicyclohexylphosphino-2',6'-dimethoxybiphenyl (0.27 g, 0.63 mmol), and potassium carbonate (0.29 g, 2.12 mmol). The vessel was sealed, and the contents were degassed under vacuum/backfilled with N$_2$ (×3). The mixture was heated to 100° C. and was allowed to stir. After 2 h, LC/MS analysis revealed that the reaction was complete. The mixture was cooled to room temperature and was concentrated to provide a brown oil. Chromatographic purification (CombiFlash, 40 g SiO$_2$ gold column, 20-70% 3:1 ethyl acetate:ethanol/heptane elute) afforded (+/−)-3-

(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-5-d (0.30 g, 0.72 mmol, 68% yield) as a tan solid: $^1$H NMR (400 MHz, DMSO-d6) δ 8.60 (s, 1H), 8.22 (d, J=2.3 Hz, 1H), 8.10 (d, J=8.1 Hz, 1H), 7.73 (dd, J=8.6, 2.3 Hz, 1H), 7.30 (d, J=8.1 Hz, 1H), 6.88 (d, J=8.6 Hz, 1H), 6.76 (d, J=1.9 Hz, 1H), 6.49 (d, J=1.9 Hz, 1H), 5.39 (s, 2H), 4.72 (d, J=7.8 Hz, 1H), 4.27 (dq, J=7.8, 6.4 Hz, 1H), 3.86 (s, 3H), 3.70 (s, 3H), 1.04 (d, J=6.4 Hz, 3H) ppm; (M+1)=420.

Example 2

Synthesis of (+/−)-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-2,5-d2 (Compound 2)

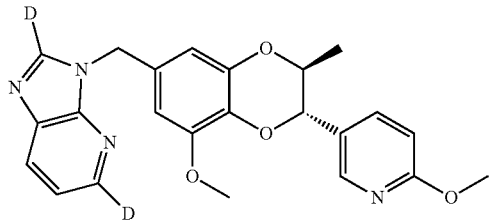 [SMILES: [2H]c1ccc2nc([2H])n(Cc3cc(OC)c4c(c3)O[C@@H](C)[C@H](c3ccc(OC)nc3)O4)c2n1]

Example 2-1

Preparation of 2-bromo-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-5-d

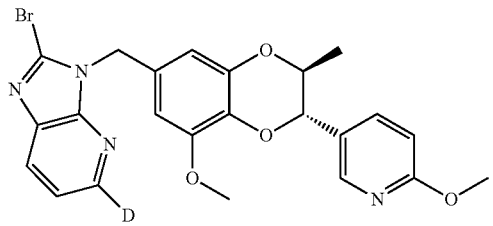 [SMILES: [2H]c1ccc2nc(Br)n(Cc3cc(OC)c4c(c3)O[C@@H](C)[C@H](c3ccc(OC)nc3)O4)c2n1]

To a stirred solution of 2-bromo-3-(((trans)-8-methoxy-2-(6-methoxypyridin-3-yl)-3-methyl-2,3-dihydrobenzo [b][1,4]dioxin-6-yl)methyl)-3H-imidazo[4,5-b]pyridine-5-d (0.25 g, 0.59 mmol) in N,N-dimethylformamide (3 ml) was added carbon tetrabromide (0.32 g, 0.96 mmol) and sodium tert-butoxide (0.23 g, 2.35 mmol). The resulting dark brown mixture was stirred at room temperature. After 30 min, LC/MS analysis revealed that a new product had formed and that starting material remained. Additional portions of carbon tetrabromide (0.32 g, 0.96 mmol) and sodium tert-butoxide (0.23 g, 2.35 mmol) were added to the mixture. After 1 h, LC/MS analysis revealed that the reaction was still not complete. The mixture was quenched into saturated ammonium chloride solution (50 mL). The mixture was extracted with ethyl acetate (40 mL). The organic phase was washed with brine (30 mL), dried over magnesium sulfate, filtered, and concentrated to provide a brown oil. Chromatographic purification (CombiFlash, 40 g SiO$_2$ gold column, 10-50% 3:1 ethyl acetate:ethanol/heptane elute) afforded (+/−)-2-bromo-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-5-d (0.089 g, 0.18 mmol, 31% yield) as an off-white solid: $^1$H NMR (400 MHz, DMSO-d6) δ 8.22 (d, J=2.3 Hz, 1H), 8.11 (d, J=8.0 Hz, 1H), 7.73 (dd, J=8.6, 2.3 Hz, 1H), 7.35 (d, J=8.0 Hz, 1H), 6.88 (d, J=8.6 Hz, 1H), 6.69 (d, J=1.9 Hz, 1H), 6.27 (d, J=1.9 Hz, 1H), 5.41 (s, 2H), 4.72 (d, J=7.8 Hz, 1H), 4.28 (dq, J=7.8, 6.3 Hz, 1H), 3.87 (s, 3H), 3.69 (s, 3H), 1.02 (d, J=6.3 Hz, 3H) ppm; (M+1)=498.

Example 2-2

Preparation of (+/−)-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-2,5-d2

To an stirred solution (note: reaction conducted in a 20 mL oven-dried microwave reaction vessel) of (+/−)-2-bromo-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-5-d (0.085 mg, 0.17 mmol) in 2-propanol-d8 (3 mL) was added tris(dibenzylideneacetone)dipalladium(0) (0.031 g, 0.034 mmol), 2-dicyclohexylphosphino-2',6'-dimethoxybiphenyl (0.043 g, 0.10 mmol), and potassium carbonate (0.047 g, 0.34 mmol). The vessel was sealed, and the contents were degassed under vacuum/backfilled with N$_2$ (×3). The mixture was heated to 100° C. and was stirred. After 2 h, LC/MS analysis revealed that the reaction was complete. The mixture was cooled to room temperature and was concentrated to provide a brown oil. Chromatographic purification (CombiFlash, 24 g SiO$_2$ gold column, 20-70% 3:1 ethyl acetate:ethanol/heptane elute) afforded (+/−)-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-2,5-d2 (0.047 g, 0.11 mmol, 66% yield) as a light yellow solid: $^1$H NMR (400 MHz, DMSO-d6) δ 8.22 (d, J=2.3 Hz, 1H), 8.10 (d, J=8.0 Hz, 1H), 7.73 (dd, J=8.7, 2.3 Hz, 1H), 7.30 (d, J=8.0 Hz, 1H), 6.88 (d, J=8.7 Hz, 1H), 6.76 (d, J=2.0 Hz, 1H), 6.49 (d, J=2.0 Hz, 1H), 5.39 (s, 2H), 4.72 (d, J=7.8 Hz, 1H), 4.27 (dq, J=7.8, 6.3 Hz, 1H), 3.86 (s, 3H), 3.70 (s, 3H), 1.04 (d, J=6.3 Hz, 3H) ppm; (M+1)=421.

Example 3

Synthesis of (+/−)-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine (Compound 3)

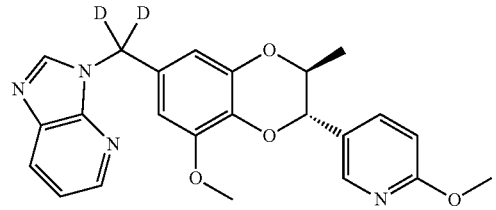 [SMILES: [2H]C([2H])(c1cc(OC)c2c(c1)O[C@@H](C)[C@H](c1ccc(OC)nc1)O2)n1cnc2cccnc21]

Example 3-1

Preparation of (+/−)-((trans)-8-methoxy-2-(6-methoxypyridin-3-yl)-3-methyl-2,3-dihydrobenzo[b][1,4]dioxin-6-yl)methan-d2-ol

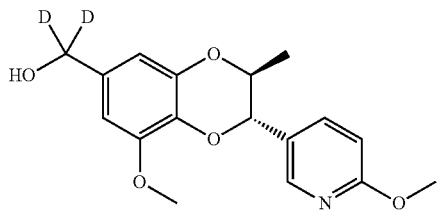 [SMILES: [2H]C([2H])(O)c1cc(OC)c2c(c1)O[C@@H](C)[C@H](c1ccc(OC)nc1)O2]

To a 0° C. stirred solution of (+/−)-methyl (trans)-8-methoxy-2-(6-methoxypyridin-3-yl)-3-methyl-2,3-dihydrobenzo[b][1,4]dioxine-6-carboxylate (2.08 g, 6.02 mmol) in tetrahydrofuran (60 mL) was added lithium aluminum deuteride (0.34 g, 8.13 mmol) in one portion (minor evolution of gas noted). The resulting gray mixture was stirred at 0° C. After 15 min, LC/MS analysis revealed that the reaction was complete. The mixture was quenched by the addition of water (0.50 mL), 1N sodium hydroxide solution (0.50 mL), and water (1.5 mL). The resulting mixture was stirred at 0° C. for 15 min, and then magnesium sulfate (ca. 10 g) was added. The mixture was filtered through Celite, and the filter cake was washed with ethyl acetate (100 mL). The filtrate was concentrated to provide (+/−)-((trans)-8-methoxy-2-(6-methoxypyridin-3-yl)-3-methyl-2,3-dihydrobenzo[b][1,4]dioxin-6-yl)methan-d2-ol (1.92 g, 6.01 mmol, 100% yield) as a sticky white foam: $^1$H NMR (400 MHz, CDCl$_3$) δ 8.15 (d, J=2.5 Hz, 1H), 7.59 (dd, J=8.6, 2.5 Hz, 1H), 6.79 (d, J=8.6 Hz, 1H), 6.59 (d, J=1.9 Hz, 1H), 6.57 (d, J=1.9 Hz, 1H), 4.63 (d, J=7.8 Hz, 1H), 4.14 (dq, J=7.8, 6.4 Hz, 1H), 3.95 (s, 3H), 3.86 (s, 3H), 1.19 (d, J=6.4 Hz, 3H); (M+1)=320.

Example 3-2

Preparation of (+/−)-5-((trans)-6-(azidomethyl-d2)-8-methoxy-3-methyl-2,3-dihydrobenzo[b][1,4]dioxin-2-yl)-2-methoxypyridine

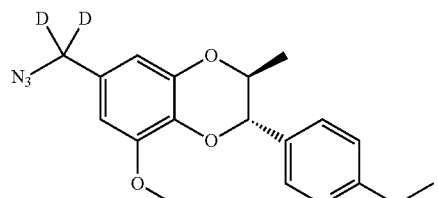

To a stirred solution of (+/−)-((trans)-8-methoxy-2-(6-methoxypyridin-3-yl)-3-methyl-2,3-dihydrobenzo [b][1,4] dioxin-6-yl)methan-d2-ol (1.92 g, 6.01 mmol) and diphenylphosphoryl azide (2.07 mL, 9.62 mmol) in tetrahydrofuran (50 mL) was added 1,8-diazabicyclo[5.4.0]undec-7-ene (1.4 mL, 9.62 mmol). The resulting mixture was heated to reflux and stirred under an inert atmosphere. After 1 h, LC/MS analysis revealed that the reaction was complete. The colorless solution was cooled to room temperature and was concentrated to provide a yellow oil. Chromatographic purification (CombiFlash, 40 g SiO$_2$ gold column, 10-30% ethyl acetate/heptane elute) afforded (+/−)-5-((trans)-6-(azidomethyl-d2)-8-methoxy-3-methyl-2,3-dihydrobenzo[b][1,4]dioxin-2-yl)-2-methoxypyridine (1.78 g, 5.17 mmol, 86% yield) as a white solid: $^1$H NMR (400 MHz, CDCl$_3$) δ 8.19 (d, J=2.4 Hz, 1H), 7.60 (dd, J=8.7, 2.4 Hz, 1H), 6.80 (d, J=8.7 Hz, 1H), 6.57 (d, J=2.0 Hz, 1H), 6.47 (d, J=2.0 Hz, 1H), 4.65 (d, J=7.9 Hz, 1H), 4.15 (dq, J=7.9, 6.4 Hz, 1H), 3.96 (s, 3H), 3.86 (s, 3H), 1.20 (d, J=6.4 Hz, 3H) ppm; (M+1)=345.

Example 3-3

Preparation of (+/−)-((trans)-8-methoxy-2-(6-methoxypyridin-3-yl)-3-methyl-2,3-dihydrobenzo[b][1,4]dioxin-6-yl)methan-d2-amine

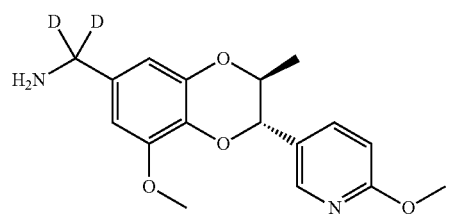 [SMILES: [2H]C([2H])(N)c1cc(OC)c2c(c1)O[C@@H](C)[C@H](c1ccc(OC)nc1)O2]

To a stirred solution of (+/−)-5-((trans)-6-(azidomethyl-d2)-8-methoxy-3-methyl-2,3-dihydrobenzo [b][1,4]dioxin-2-yl)-2-methoxypyridine (1.78 g, 5.17 mmol) in tetrahydrofuran (50 mL) and water (5 mL) was added polymer-bound triphenylphosphine (3.50 g, ca. 10.50 mmol). The orange suspension was heated to reflux and was stirred under an inert atmosphere. After 2 h, LC/MS analysis revealed that the reaction was complete. The mixture was cooled to room temperature and was filtered through Celite with the aid of ethyl acetate (50 mL). The filtrate was dried over magnesium sulfate, filtered, and concentrated to provide (+/−)-((trans)-8-methoxy-2-(6-methoxypyridin-3-yl)-3-methyl-2,3-dihydrobenzo[b][1,4]dioxin-6-yl)methan-d2-amine (1.61 g, 5.06 mmol, 98% yield) as a colorless oil: $^1$H NMR (400 MHz, CDCl$_3$) δ 8.17 (d, J=2.4 Hz, 1H), 7.59 (dd, J=8.6, 2.4 Hz, 1H), 6.78 (d, J=8.6 Hz, 1H), 6.54 (d, J=1.9 Hz, 1H), 6.50 (d, J=1.9 Hz, 1H), 4.63 (d, J=7.8 Hz, 1H), 4.13 (dq, J=7.8, 6.4 Hz, 1H), 3.95 (s, 3H), 3.85 (s, 3H), 2.04 (s, 2H), 1.19 (d, J=6.4 Hz, 3H) ppm; (M−16)=302.

Example 3-4

Preparation of (+/−)-N-(((trans)-8-methoxy-2-(6-methoxypyridin-3-yl)-3-methyl-2,3-dihydrobenzo[b][1,4]dioxin-6-yl)methyl-d2)-3-nitropyridin-2-amine

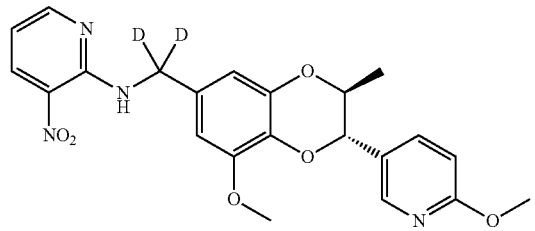 [SMILES: [2H]C([2H])(Nc1ncccc1[N+](=O)[O-])c1cc(OC)c2c(c1)O[C@@H](C)[C@H](c1ccc(OC)nc1)O2]

To a stirred solution of (+/−)-((trans)-8-methoxy-2-(6-methoxypyridin-3-yl)-3-methyl-2,3-dihydrobenzo[b][1,4]dioxin-6-yl)methan-d2-amine (1.61 g, 5.06 mmol) and N,N-diisopropylethylamine (1.3 mL, 7.59 mmol) in acetonitrile (30 mL) was added 2-chloro-3-nitropyridine (0.84 g, 5.31 mmol). The resulting mixture was heated to reflux and was stirred under an inert atmosphere. After 16 h, LC/MS analysis of the yellow mixture revealed that the reaction was complete. The mixture was cooled to room temperature and was diluted with water (50 mL). The resulting mixture was extracted with ethyl acetate (2×50 mL). The combined organic phases were dried over magnesium sulfate, filtered, and concentrated to provide (+/−)-N-(((trans)-8-methoxy-2-(6-methoxypyridin-3-yl)-3-methyl-2,3-dihydrobenzo[b][1,4]dioxin-6-yl)methyl-d2)-3-nitropyridin-2-amine (2.05 g, 4.65 mmol, 92% yield) as a yellow solid: $^1$H NMR (400 MHz, CDCl$_3$) δ 8.51-8.40 (m, 3H), 8.17 (d, J=2.4 Hz, 1H), 7.58 (dd, J=8.6, 2.4 Hz, 1H), 6.79 (d, J=8.6 Hz, 1H), 6.70-6.66 (m, 1H), 6.61 (d, J=1.9 Hz, 1H), 6.55 (d, J=1.9 Hz, 1H), 4.63 (d, J=7.8 Hz, 1H), 4.18-4.09 (m, 1H), 3.95 (s, 3H), 3.84 (s, 3H), 1.19 (d, J=6.4 Hz, 3H) ppm; (M+1)=441.

Example 3-5

Preparation of (+/−)-N$^2$-(((trans)-8-methoxy-2-(6-methoxypyridin-3-yl)-3-methyl-2,3-dihydrobenzo[b][1,4]dioxin-6-yl)methyl-d2)pyridine-2,3-diamine

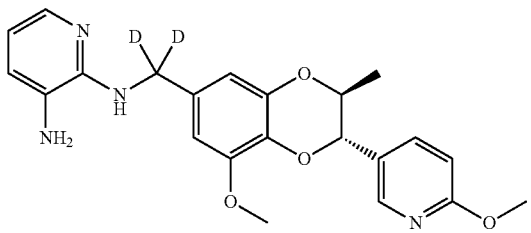 [SMILES: [2H]C([2H])(Nc1ncccc1N)c1cc(OC)c2c(c1)O[C@@H](C)[C@H](c1ccc(OC)nc1)O2]

To a stirred solution of (+/−)-N-(((trans)-8-methoxy-2-(6-methoxypyridin-3-yl)-3-methyl-2,3-dihydrobenzo[b][1,4]dioxin-6-yl)methyl-d2)-3-nitropyridin-2-amine (2.05 g, 4.65 mmol) and ammonium chloride (1.99 g, 37.23 mmol) in a mixture of tetrahydrofuran (50 mL)/methanol (20 mL)/water (10 mL) was added zinc powder (2.43 g, 37.23 mmol). The resulting mixture was stirred at room temperature. After 45 min, LC/MS analysis revealed that the reaction was complete. The gray suspension was filtered through Celite, and the filter cake was washed with ethyl acetate (75 mL). The filtrate was washed with 5N ammonium hydroxide solution (50 mL). The organic phase was dried over magnesium sulfate, filtered, and concentrated to provide (+/−)-N$^2$-(((trans)-8-methoxy-2-(6-methoxypyridin-3-yl)-3-methyl-2,3-dihydrobenzo[b][1,4]dioxin-6-yl)methyl-d2)pyridine-2,3-diamine (1.72 g, 4.19 mmol, 90% yield) as a dark brown solid: $^1$H NMR (400 MHz, CDCl$_3$) δ 8.17 (d, J=2.4 Hz, 1H), 7.78 (dd, J=5.1, 1.5 Hz, 1H), 7.58 (dd, J=8.6, 2.4 Hz, 1H), 6.88 (dd, J=7.4, 1.5 Hz, 1H), 6.78 (d, J=8.6 Hz, 1H), 6.65 (d, J=1.9 Hz, 1H), 6.59 (d, J=1.9 Hz, 1H), 6.56 (dd, J=7.4, 5.1 Hz, 1H), 4.63 (d, J=7.7 Hz, 1H), 4.40 (br s, 1H), 4.18-4.09 (m, 1H), 3.95 (s, 3H), 3.83 (s, 3H), 3.22 (br s, 2H), 1.19 (d, J=6.3 Hz, 3H) ppm; (M+1)=411.

Example 3-6

Preparation of (+/−)-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine To a stirred suspension of (+/−)-N$^2$-(((trans)-8-methoxy-2-(6-methoxypyridin-3-yl)-3-methyl-2,3-dihydrobenzo[b][1,4]dioxin-6-yl)methyl-d2)pyridine-2,3-diamine (1.72 g, 4.19 mmol) and triethyl orthoformate (2.0 mL, 11.78 mmol) in ethanol (75 mL) was added p-toluenesulfonic acid monohydrate (ca. 0.050 g). The resulting mixture was heated to reflux and was stirred under an inert atmosphere. After 16 h, LC/MS analysis revealed that the reaction was complete. The mixture was cooled to room temperature and was concentrated to provide a brown oil. Chromatographic purification (CombiFlash, 120 g SiO$_2$ gold column, 20-50% 3:1 ethyl acetate:ethanol/heptane elute) provided a light brown solid. The solid was suspended in a mixture of methyl tert-butyl ether (12 mL)/ethyl acetate (0.50 mL). The mixture was heated to 55° C. After 3 h, the warm mixture was filtered, and the filter cake was washed with methyl tert-butyl ether (10 mL) and dried to afford (+/−)-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine (0.99 g, 2.37 mmol, 57% yield) as a tan solid: $^1$H NMR (400 MHz, CDCl$_3$) δ 8.45 (dd, J=4.8, 1.4 Hz, 1H), 8.16 (d, J=2.4 Hz, 1H), 8.10 (dd, J=8.0, 1.4 Hz, 1H), 8.06 (s, 1H), 7.56 (dd, J=8.6, 2.4 Hz, 1H), 7.27 (dd, J=8.0, 4.8 Hz, 1H), 6.78 (d, J=8.6 Hz, 1H), 6.54 (s, 2H), 4.62 (d, J=7.8 Hz, 1H), 4.12 (dq, J=7.8, 6.3 Hz, 1H), 3.94 (s, 3H), 3.79 (s, 3H), 1.17 (d, J=6.3 Hz, 3H) ppm; (M+1)=421.

Example 4

Synthesis of (+/−)-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine-2-d (Compound 4)

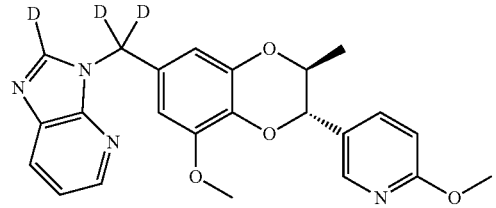 [SMILES: [2H]c1nc2cccnc2n1C([2H])([2H])c1cc(OC)c2c(c1)O[C@@H](C)[C@H](c1ccc(OC)nc1)O2]

Example 4-1

Preparation of (+/−)-2-bromo-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine To a stirred solution of (+/−)3-(((trans)-8-methoxy-2-(6-methoxypyridin-3-yl)-3-methyl-2,3-dihydrobenzo [b][1,4]dioxin-6-yl)methyl-d2)-3H-imidazo[4,5-b]pyridine (0.45 g, 1.08 mmol) in N,N-dimethylformamide (5 ml) was added carbon tetrabromide (0.54 g, 1.62 mmol) and sodium tert-butoxide (0.41 g, 4.31 mmol), resulting in the formation of a dark brown mixture. The mixture was stirred at room temperature. After 20 min, LC/MS analysis revealed that a new product had formed and that starting material remained (~1:1). Additional portions of carbon tetrabromide (0.54 g, 1.62 mmol) and sodium tert-butoxide (0.41 g, 4.31 mmol) were added to the mixture (repeated at t=40 min, t=60 min, and t=80 min). After a total of 100 min, LC/MS analysis revealed that the reaction was nearly complete. The mixture was quenched into saturated ammonium chloride solution (50 mL). The mixture was extracted with ethyl acetate (40 mL). The organic phase was washed with brine (30 mL), dried over magnesium sulfate, filtered, and concentrated to provide a brown oil. Chromatographic purification (Combi-Flash, 40 g SiO$_2$ gold column, 10-50% 3:1 ethyl acetate:ethanol/heptane elute) afforded (+/−)-2-bromo-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine (0.39 g, 0.79 mmol, 73% yield) as an off-white solid: $^1$H NMR (400 MHz, DMSO-d6) δ 8.42 (dd, J=4.9, 1.5 Hz, 1H), 8.22 (d, J=2.3 Hz, 1H), 8.10 (dd, J=8.1, 1.5 Hz, 1H), 7.73 (dd, J=8.6, 2.3 Hz, 1H), 7.35 (dd, J=8.1, 4.9 Hz, 1H), 6.88 (d, J=8.6 Hz, 1H), 6.70 (d, J=1.9 Hz, 1H), 6.28 (d, J=1.9 Hz, 1H), 4.72 (d, J=7.9 Hz, 1H), 4.28 (dq, J=7.9, 6.3 Hz, 1H), 3.86 (s, 3H), 3.69 (s, 3H), 1.03 (d, J=6.3 Hz, 3H) ppm; (M+1)=499.

Example 4-2

Preparation of (+/−)-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine-2-d To a stirred solution (note: reaction conducted in a 20 mL oven-dried microwave reaction vessel) of (+/−)-2-bromo-3-(((trans)-8-methoxy-2-(6-methoxypyridin-3-yl)-3-methyl-2,3-dihydrobenzo [b][1,4]dioxin-6-yl)methyl-d2)-3H-imidazo[4,5-b]pyridine (0.32 g, 0.65 mmol) in propanol-d8 (3 mL) was added tris(dibenzylidene)dipalladium(0) (0.12 g, 0.13 mmol), 2-dicyclohexylphosphino-2',6'-dimethoxybiphenyl (0.16 g, 039 mmol), and potassium carbonate (0.18 g, 1.29 mmol). The vessel was sealed, and the contents were degassed under vacuum/backfilled with N$_2$ (×3). The mixture was heated to 100° C. in a heating block. After 2 h, LC/MS analysis revealed that the reaction was complete. The mixture was cooled to room temperature and was concentrated to provide a brown oil. Chromatographic purification (CombiFlash, 80 g SiO$_2$ gold column, 20-70% 3:1 ethyl acetate:ethanol/heptane elute) afforded an impure brown oil. Preparative HPLC purification (Interchim Column: F$_{0040}$-51 g-51.0 g (20 bar)) column, 20% acetonitrile/water/0.1% formic acid to 100% acetonitrile/0.1% formic acid elute) provided two pure fractions. The fractions were combined and diluted with saturated sodium bicarbonate solution (30 mL). The mixture was extracted with ethyl acetate (30 mL). The organic phase was dried over magnesium sulfate, filtered, and concentrated to provide (+/−)-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine-2-d (0.16 g, 0.37 mmol, 57% yield) as a white solid: $^1$H NMR (400 MHz, DMSO-d6) δ 8.40 (dd, J=4.8, 1.5 Hz, 1H), 8.22 (d, J=2.5 Hz, 1H), 8.10 (dd, J=8.0, 1.5 Hz, 1H), 7.73 (dd, J=8.6, 2.5 Hz, 1H), 7.30 (dd, J=8.0, 4.8 Hz, 1H), 6.88 (d, J=8.6 Hz, 1H), 6.76 (d, J=2.0 Hz, 1H), 6.50 (d, J=2.0 Hz, 1H), 4.72 (d, J=7.8 Hz, 1H), 4.27 (dq, J=7.8, 6.3 Hz, 1H), 3.86 (s, 3H), 3.70 (s, 3H), 1.04 (d, J=6.3 Hz, 3H) ppm; (M+1)=421.

Example 5

Synthesis of 3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d (Compound 5)

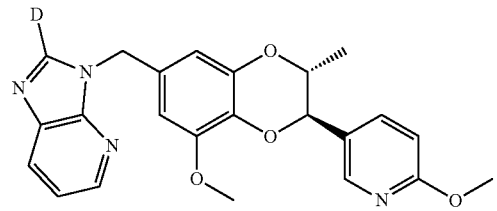 [SMILES: [2H]c1nc2cccnc2n1Cc1cc(OC)c2c(c1)O[C@H](C)[C@@H](c1ccc(OC)nc1)O2]

Example 5-1

Preparation and separation of 3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine and 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine

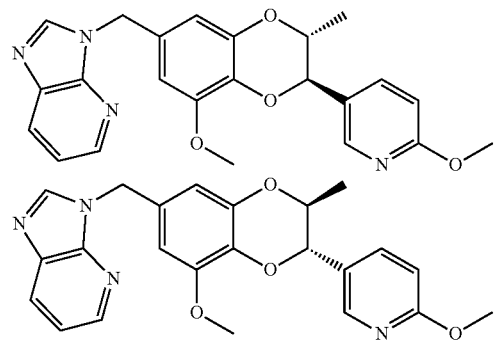

The preparation of (+/−)-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine was accomplished in five steps from (+/−)-((trans)-8-methoxy-2-(6-methoxypyridin-3-yl)-3-methyl-2,3-dihydrobenzo[b][1,4]dioxin-6-yl)methanol (Example 1-2) according to the procedures described in Example 3-2 through Example 3-6. The racemic product (~95:5 trans:cis) was subjected to chiral SFC separation (Whelk-01 21×250 mm column, flow rate 70 mL/min, 50% ethanol in CO$_2$/0.1% diethylamine elute, compound (2.24 g) dissolved in 60 mL methanol/15 mL dichloromethane, 1.8 mL of solution per injection) to provide three fractions. The first fraction contained a small amount of one of the cis-enantiomers. The second fraction contained 3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine (contaminated with a small amount of one of the cis-enantiomers), and the third fraction contained 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine: $^1$H NMR (400 MHz, CDCl$_3$) δ

8.45 (dd, J=4.8, 1.5 Hz, 1H), 8.16 (d, J=2.5 Hz, 1H), 8.09 (dd, J=8.0, 1.5 Hz, 1H), 8.04 (s, 1H), 7.56 (dd, J=8.6, 2.5 Hz, 1H), 7.29-7.26 (m, 1H), 6.78 (d, J=8.6 Hz, 1H), 6.54-6.52 (m, 2H), 5.38 (s, 2H), 4.62 (d, J=7.8 Hz, 1H), 4.11 (dq, J=7.8, 6.3 Hz, 1H), 3.94 (s, 3H), 3.79 (s, 3H), 1.17 (d, J=6.3 Hz, 3H) ppm.

Example 5-2

Preparation of 2-bromo-3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine

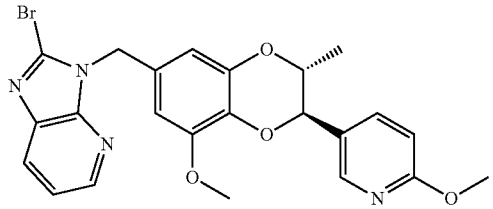 [SMILES: COc1ccc([C@H]2Oc3c(OC)cc(Cn4c(Br)nc5cccnc54)cc3O[C@@H]2C)cn1]

To a stirred solution of 3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine (0.44 g, 1.05 mmol) in N,N-dimethylformamide (5 ml) was added carbon tetrabromide (0.38 g, 1.16 mmol) and sodium tert-butoxide (0.40 g, 4.21 mmol). The resulting dark brown mixture was stirred at room temperature. After 30 min, LC/MS analysis revealed that a new product had formed and that starting material remained (~1:1). The mixture was quenched into saturated ammonium chloride solution (50 mL). The mixture was extracted with ethyl acetate (40 mL). The organic phase was washed with brine (30 mL), dried over magnesium sulfate, filtered, and concentrated to provide a brown oil. Chromatographic purification (CombiFlash, 24 g SiO$_2$ gold column, 10-50% 3:1 ethyl acetate:ethanol/heptane elute) afforded 2-bromo-3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine (0.18 g, 0.37 mmol, 35% yield) as a tan solid: $^1$H NMR (400 MHz, DMSO-d6) δ 8.42 (dd, J=4.9, 1.5 Hz, 1H), 8.22 (d, J=2.4 Hz, 1H), 8.11 (dd, J=8.1, 1.5 Hz, 1H), 7.73 (dd, J=8.6, 2.4 Hz, 1H), 7.36 (dd, J=8.1, 4.9 Hz, 1H), 6.88 (d, J=8.6 Hz, 1H), 6.69 (d, J=1.9 Hz, 1H), 6.27 (d, J=1.9 Hz, 1H), 5.41 (s, 2H), 4.72 (d, J=7.8 Hz, 1H), 4.28 (dq, J=7.8, 6.3 Hz, 1H), 3.86 (s, 3H), 3.69 (s, 3H), 1.02 (d, J=6.3 Hz, 3H) ppm; (M+1)=497.

Example 5-3

Preparation of 3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d To a stirred solution (note: reaction conducted in a 20 mL oven-dried microwave reaction vessel) of 2-bromo-3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine (0.16 g, 0.32 mmol) in 2-propanol-d8 (5 mL) was added tris(dibenzylidene)dipalladium(0) (0.059 g, 0.064 mmol), 2-dicyclohexylphosphino-2',6'-dimethoxybiphenyl (0.080 g, 0.19 mmol), and potassium carbonate (0.089 g, 0.64 mmol). The vessel was sealed, and the contents were degassed under vacuum/backfilled with N$_2$ (×3). The mixture was heated to 100° C. in a heating block. After 2 h, LC/MS analysis revealed that the reaction was complete. The mixture was cooled to room temperature and was concentrated to provide a brown oil. Chromatographic purification (CombiFlash, 40 g SiO$_2$ gold column, 20-70% 3:1 ethyl acetate:ethanol/heptane elute) afforded 3-(((2R,3R)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d (0.075 g, 0.18 mmol, 56% yield) as a yellow solid: $^1$H NMR (400 MHz, DMSO-d6) δ 8.40 (dd, J=4.7, 1.5 Hz, 1H), 8.22 (d, J=2.4 Hz, 1H), 8.10 (dd, J=8.0, 1.5 Hz, 1H), 7.73 (dd, J=8.6, 2.4 Hz, 1H), 7.30 (dd, J=8.0, 4.7 Hz, 1H), 6.88 (d, J=8.6 Hz, 1H), 6.76 (d, J=1.9 Hz, 1H), 6.49 (d, J=1.9 Hz, 1H), 5.39 (s, 2H), 4.72 (d, J=7.8 Hz, 1H), 4.28 (dq, J=7.8, 6.3 Hz, 1H), 3.86 (s, 3H), 3.70 (s, 3H), 1.04 (d, J=6.3 Hz, 3H) ppm; (M+1)=420.

Example 6

Synthesis of 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d (Compound 6)

Method A:

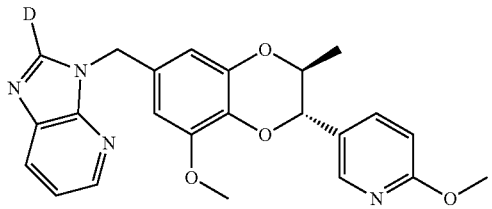 [SMILES: [2H]c1nc2cccnc2n1Cc1cc(OC)c2c(c1)O[C@@H](C)[C@H](c1ccc(OC)nc1)O2]

Example 6-1

Preparation of 2-bromo-3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine

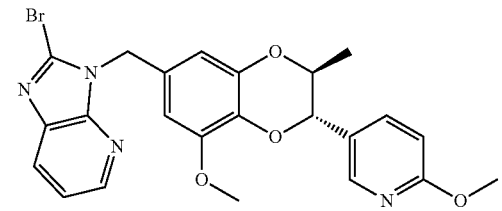 [SMILES: COc1ccc([C@@H]2Oc3c(OC)cc(Cn4c(Br)nc5cccnc54)cc3O[C@H]2C)cn1]

To a stirred solution of 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine (0.51 g, 1.22 mmol) in N,N-dimethylformamide (5 ml) was added carbon tetrabromide (0.53 g, 1.58 mmol) and sodium tert-butoxide (0.50 g, 5.22 mmol). The resulting dark brown mixture was stirred at room temperature. After 1 h, LC/MS analysis revealed that a new product had formed and that starting material remained (~1:1). The mixture was quenched into saturated ammonium chloride solution (50 mL). The mixture was extracted with ethyl acetate (40 mL). The organic phase was washed with brine (30 mL), dried over magnesium sulfate, filtered, and concentrated to provide a brown oil. Chromatographic purification (CombiFlash, 40 g SiO$_2$ gold column, 10-60% 3:1 ethyl acetate: ethanol/heptane elute) afforded 2-bromo-3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine (0.20 mg, 0.39 mmol, 32% yield) as an off-white solid: $^1$H NMR (400 MHz, DMSO-d6) δ 8.42 (dd, J=4.8, 1.5 Hz, 1H), 8.22 (d, J=2.4 Hz, 1H), 8.11 (dd, J=8.1, 1.5 Hz, 1H), 7.73 (dd, J=8.6, 2.4 Hz, 1H), 7.36 (dd, J=8.1, 4.8 Hz, 1H), 6.88 (d, J=8.6 Hz, 1H), 6.69 (d, J=2.0 Hz, 1H), 6.27 (d, J=2.0 Hz, 1H), 5.41 (s, 2H), 4.72 (d, J=7.9 Hz, 1H), 4.28 (dq, J=7.9, 6.3 Hz, 1H), 3.86 (s, 3H), 3.69 (s, 3H), 1.02 (d, J=6.3 Hz, 3H) ppm; (M+1)=497.

Example 6-2

Preparation of 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d To a stirred solution (note: reaction conducted in a 20 mL oven-dried microwave reaction vessel) of 2-bromo-3-(((2S,3 S)-8-methoxy-2-(6-methoxypyridin-3-yl)-3-methyl-2,3-dihydrobenzo [b][1,4]dioxin-6-yl)methyl)-3H-imidazo [4,5-b]pyridine (0.15 mg, 0.30 mmol) in 2-propanol-d8 (5 mL) was added tris(dibenzylidene)dipalladium(0) (0.054 g, 0.059 mmol), 2-dicyclohexylphosphino-2',6'-dimethoxybiphenyl (0.074 g, 0.18 mmol), and potassium carbonate (82.52 mg, 591.13 mol). The vessel was sealed, and the contents were degassed under vacuum/backfilled with N$_2$ (×3). The mixture was heated to 100° C. in a heating block. After 1 h, LC/MS analysis revealed that the reaction was complete. The mixture was cooled to room temperature and was concentrated to provide a brown oil. Chromatographic purification (CombiFlash, 40 g SiO$_2$ gold column, 20-70% 3:1 ethyl acetate:ethanol/heptane elute) afforded 3-(((2S, 3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d (0.088 g, 0.21 mmol, 71% yield) as a yellow solid: $^1$H NMR (400 MHz, DMSO-d6) δ 8.40 (dd, J=4.8, 1.5 Hz, 1H), 8.22 (d, J=2.4 Hz, 1H), 8.10 (dd, J=8.0, 1.5 Hz, 1H), 7.73 (dd, J=8.7, 2.4 Hz, 1H), 7.30 (dd, J=8.0, 4.8 Hz, 1H), 6.88 (d, J=8.7 Hz, 1H), 6.76 (d, J=1.9 Hz, 1H), 6.49 (d, J=1.9 Hz, 1H), 5.39 (s, 2H), 4.72 (d, J=7.8 Hz, 1H), 4.28 (dq, J=7.8, 6.3 Hz, 1H), 3.86 (s, 3H), 3.70 (s, 3H), 1.04 (d, J=6.3 Hz, 3H) ppm; (M+1)=420.

Example 7

Synthesis of 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d (Compound 6)

Method B:
3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine (8.00 g, 19.12 mmol) was dissolved in 2-methyltetrahydrofuran (220 mL) with heating. The solution was distilled to remove 20 mL of solvent to dry the mixture. After cooling to room temperature, the mixture was treated with potassium tert-butoxide (3.2 g, 28.7 mmol) and methanol-di (24.00 ml, 646 mmol). The solution was heated to 58-61° C. After 4 h, the solution was cooled to room temperature and washed with 10% w/w aqueous ammonium chloride solution (150 mL). The organic layer was washed twice with brine, dried over magnesium sulfate, filtered and concentrated to provide 7.60 g of a solid. This material was dissolved in 2-methyltetrahydrofuran (76 mL) by heating to 60° C. The solution was seeded and stirred at 45° C. for 1 h. The mixture was stirred at room temperature for 1 h, and then at 0-5° C. for 1 h. The resulting solid was filtered, washed with a small amount of 2-methyltetrahydrofuran, and dried under vacuum to afford 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d as an off-white crystalline solid (6.3 g, 79% yield, LCMS: 94.5% D, 1H NMR: 94% D).

Example 8

Large-Scale Synthesis of 3-(((2S,3S)-8-methoxy-2-(6-methoxypyridin-3-yl)-3-methyl-2,3-dihydrobenzo [b][1,4]dioxin-6-yl)methyl)-3H-imidazo[4,5-b]pyridine-2-d (Compound 6)

50 g of 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine was charged to 500 mL of toluene. The resulting slurry was heated to 120-130° C. and refluxed for 2-3 h with Dean stark water removal. After removing most of the solvent, the mixture was chased with heptane (2×250 mL) at below 60° C. to 3.0 to 4.0 volumes. The resulting slurry was solvent exchanged with 2-methyl THF (2×250 mL) at below 60° C. to 3.0 to 4.0 volumes. After charging 800 mL(16 vol) of 2-methyl THF, the mixture was warmed to 60 to 65° C. and charged with 50 mL of MeOD and 67 mL (1.0 eq) of a 20% potassium tertiary butoxide solution in THF at 60-65° C. The reaction mixture was maintained for 3h at 60-65° C. The reaction was cooled to 20-30° C., and quenched with 1000 mL (20 vol.) of an aqueous 10% ammonium chloride solution. The organic layer was diluted with ethyl acetate and washed with water (3×250 mL) and 25% brine solution (250 mL). The organic layer was distilled to 3.0 to 4.0 volumes at 60° C. under vacuum. The mixture was chased with toluene (2×250 mL) below 60° C. to 3.0 to 4.0 volumes, chased with heptane (2×250 mL) at below 60° C. to 3.0 to 4.0 volumes. The resulting slurry was solvent exchanged with 2-methyl THF (2×250 mL) at below 60° C. to 3.0 to 4.0 volumes. The mixture was charged with 1050 mL (21 vol) of 2-methyl THF and reaction mass warm up to 60-65° C. to get a clear solution. The pale-yellow clear solution that was obtained contained 80-85% D Compound 6 by 1H NMR. The solution was charged with 100 mL of MeOD and 13.4 mL (0.2 eq) of 20% potassium tertiary butoxide solution in THF at 60-65° C. The reaction was maintained for 3 h at 60-65° C. The reaction was cooled to 20-30° C., and quenched with 500 mL (10 vol.) of 10% ammonium chloride solution. The organic layer was further washed with water (3×250 mL). The organic layer was distilled to 7.5 to 8.0 volumes at 60° C. under vacuum. The resulting slurry was refluxed at 65-70° C. to get a clear solution. The mixture was cooled to 60-65° C. over a period of 20 min and seeded 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d (0.025 g). The mixture was slowly cooled to 25 to 30° C. over a period of 2-3h and further cooled to 0-5° C. over a period of 2-3 h and stirred for 1-2 h. The solids were filtered and washed with 50 mL (1.0 vol) of per-chilled 2-methyl THF. The wet material (39.5 g) were placed under high vacuum for 16 h at 45-50° C. to obtain 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d (39.2g; 78% yield; 95% D by LCMS).

Example 9

Additional Large-Scale Synthesis Advantageously Stereoselective for Compound 6

Example 9-1

Preparation of 2-(5-((3H-imidazo[4,5-b]pyridin-3-yl)methyl)-2-(benzyloxy)-3-methoxyphenoxy)-1-(6-methoxypyridin-3-yl)propan-1-one

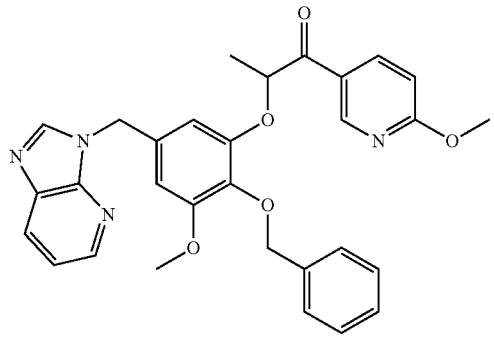 [SMILES: COc1ccc(C(=O)C(C)Oc2cc(Cn3cnc4cccnc43)cc(OC)c2OCc2ccccc2)cn1]

A mixture of 2-bromo-1-(6-methoxypyridin-3-yl)propan-1-one (21.2 g, 87 mmol, 1 eq, CAS 1391089-35-2), 5-((3H-imidazo[4,5-b]pyridin-3-yl)methyl)-2-(benzyloxy)-3-methoxyphenol (32.9 g. 91.3 mmol, 1.05 eq) (WO2017015267 Example 1-193) and potassium carbonate (30 g, 218 mmol, 2.5 eq) in acetonitrile (330 mL) was stirred at room temperature for 4 h. HPLC analysis showed complete consumption of 2-bromo-1-(6-methoxypyridin-3-yl)propan-1-one. Methyl t-butyl ether (330 mL) was added to the slurry and the mixture was filtered and the solids washed with methyl t-butyl ether. The filtrate was washed with dilute sodium hydroxide solution (350 mL) and saturated sodium chloride solution (300 mL). The solvent was swapped with methanol. The methanol solution was stirred at room temperature with seeding (20 mg). After stirring at room temperature for 16 h, the crystallized product was isolated by filtration, washed with methanol and dried to afford 2-(5-((3H-imidazo[4,5-b]pyridin-3-yl)methyl)-2-(benzyloxy)-3-methoxyphenoxy)-1-(6-methoxypyridin-3-yl)propan-1-one (35.9 g of 85% yield) as an off-white, crystalline solid, m.p. 72° C.; $^1$H NMR (400 MHz, CDCl$_3$) δ 8.83 (dd, J=2.4, 0.7 Hz, 1H), 8.39 (dd, J=4.8, 1.4 Hz, 1H), 8.13-8.03 (m, 2H), 7.96 (s, 1H), 7.48-7.41 (m, 2H), 7.36-7.21 (m, 4H), 6.69 (dd, J=8.8, 0.8 Hz, 1H), 6.55 (d, J=1.9 Hz, 1H), 6.44 (d, J=2.0 Hz, 1H), 5.32 (s, 2H), 5.29 (q, J=6.8, 1H), 4.99 (s, 2H), 3.98 (s, 3H), 3.74 (s, 3H), 1.60 (d, J=6.8 Hz, 3H)ppm; (M+1)=525.

Example 9-2

Preparation of 4-((3H-imidazo[4,5-b]pyridin-3-yl)methyl)-2-(41S,2S)-1-hydroxy-1-(6-methoxypyridin-3-yl)propan-2-yl)oxy)-6-methoxyphenol

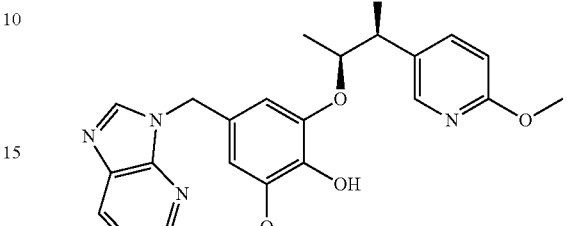

2-(5-((3H-imidazo[4,5-b]pyridin-3-yl)methyl)-2-(benzyloxy)-3-methoxyphenoxy)-1-(6-methoxypyridin-3-yl)propan-1-one (14 g, 25.2 mmol), potassium t-butoxide (1.35 g, 12.01 mmol, 0.48 eq.) and RuCl$_2$[(S)-(DM-BINAP)][(S)-DAIPEN] (CAS 220114-01-2, 0.33 g, 0.27 mmol, 0.01 eq.) were dissolved in isopropyl alcohol (230 mL) and charged into a hydrogenation reactor. The reactor was purged with nitrogen and charged with hydrogen to 70 psi. After stirring at 70 psi hydrogen pressure at 22° C. for 5 h, HPLC analysis showed the complete consumption of the starting material. Hydrogenolysis was carried out by charging Pd/C (4.8 g, 34 wt %, 5% Pd on active carbon, 50% wet) into the reactor. The Parr reactor was purged with nitrogen and charged with hydrogen to 70 psi. After stirring at 70 psi hydrogen pressure at 22° C. for 48 h, HPLC analysis showed the reaction was essentially completed. The reaction mixture was filtered through a celite pad, washed with isopropanol and methanol. The filtrate was concentrated to a clear yellow oil. The oil was dissolved in ethyl acetate (250 mL) and washed with aqueous ammonium chloride (130 mL). The aqueous layer was back extracted with ethyl acetate (30 mL). The combined organic layers was washed with saturated sodium chloride solution, dried with sodium sulfate, filtered and concentrated to obtain 4-((3H-imidazo[4,5-b]pyridin-3-yl)methyl)-2-(((1S,2S)-1-hydroxy-1-(6-methoxypyridin-3-yl)propan-2-yl)oxy)-6-methoxyphenol as a light yellow hard foam (10.1 g, 23.1 mmol, 92% yield.) The product is approximately a 84:16 ratio of the 1S,2S to 1R,2S diastereomers (by $^1$H NMR); >98% ee (by chiral HPLC) $^1$H NMR (400 MHz, CDCl$_3$) δ 8.43 (d, J=4.6 Hz, 1H), 8.13-8.05 (m, 2H), 8.02 (d, J=1.7 Hz, 1H), 7.68 and 7.61 (2 br d, J=8.7 Hz, 1H), 7.31-7.23 (m, 2H), 6.77-6.67 (m, 2H), 6.66 (d, J=2.7 Hz, 1H), 5.36 (s, 2H), 4.82 and 4.71 (br s and d, J=8.3 Hz, 1H), 4.13 (m, 1H), 3.94 (br s, 3H), 3.83 (br s, 3H), 1.18-1.07 (d, J=6.4 Hz, 3H)ppm; (M+1)=437.

Example 9-3

Preparation of 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine

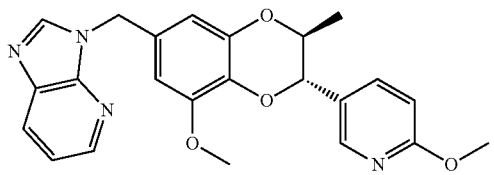 [SMILES: COc1ccc([C@@H]2Oc3c(OC)cc(Cn4cnc5cccnc54)cc3O[C@H]2C)cn1]

A solution of 4-(((3H-imidazo[4,5-b]pyridin-3-yl)methyl)-2-(((1S,2S)-1-hydroxy-1-(6-methoxypyridin-3-yl)propan-2-yl)oxy)-6-methoxyphenol (10.10 g; 23.14 mmol; 84:16 mixture of diastereomers; 1.00 eq.) in ethyl acetate (90 mL), with diisopropylethylamine (16.02 ml; 92.56 mmol; 4.00 eq.) and $CCl_4$ (5.58 ml; 57.85 mmol; 2.50 eq.) was stirred at 45-50° C. Tri n-butyl phosphine (11.99 ml; 48.60 mmol; 2.10 eq.) was added dropwise over 10 min with a slight exotherm. The resulting brown solution was stirred at 45-50° C. for 1.5 h. To the reaction was added sodium hydroxide solution (15 wt %, 40 mL, 6.5 eq.) and the mixture was stirred at 45° C. for 0.5-1 h. The reaction was cooled to room temperature. The layers were separated. The aqueous layer was extracted with ethyl acetate (40 mL). The combined organic layers were washed with saturated sodium chloride solution (50 mL), dried over sodium sulfate, filtered and concentrated to a wet-solid. The solid was stirred in methyl t-butyl ether (60 mL) for 2 h, filtered and dried under vacuum. The off-white solid was dissolved in ethanol (55 mL) at elevated temperature. The solution was stirred at room temperature with seeding and cooling to 0-5° C. The resulting solid was filtered and dried to afford 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine as off-white solid powder (6.16 g, 63.6%) 99 A % (by HPLC), 98% ee, Pd: 1 ppm; Ru: 225 ppm; Form A. m.p.164.9° C. $^1$H NMR (400 MHz, $CDCl_3$) δ 8.45 (dd, J=4.8, 1.5 Hz, 1H), 8.16 (d, J=2.4 Hz, 1H), 8.13-8.03 (m, 2H), 7.56 (dd, J=8.6, 2.5 Hz, 1H), 7.27 (dd, J=8.0, 4.8 Hz, 1H), 6.78 (d, J=8.6 Hz, 1H), 6.53 (br s, 2H), 5.38 (s, 2H), 4.62 (d, J=7.8 Hz, 1H), 4.13 (m, 1H) 3.94 (s, 3H), 3.79 (s, 3H), 1.17 (d, J=6.4 Hz, 3H)ppm. (M+1)=419.

Example 9-4

Preparation of 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d

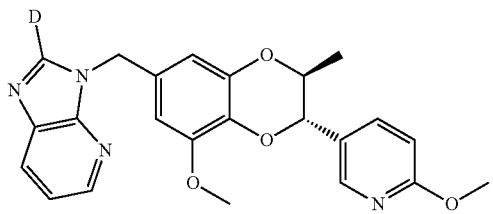 [SMILES: [2H]c1nc2cccnc2n1Cc1cc(OC)c2c(c1)O[C@@H](C)[C@H](c1ccc(OC)nc1)O2]

3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine (20 g; 47.80 mmol) was dissolved in 2-methyl tetrahydrofuran (400 mL) at 60° C. Methanol-d (20 mL; 1 V, 99% D) was added followed by solid potassium t-butoxide (5.36 g; 47.80 mmol; 1 eq). The solution was heated for 2 h. LCMS showed 87% D. The reaction solution was cooled to 22° C. The suspension was washed with aqueous 10% w/w ammonium chloride (400 mL). The organic layer was separated, diluted with ethyl acetate (200 mL) and washed with water (3×100 mL) followed by ½ saturated sodium chloride solution (100 mL). The organic layer was dried (sodium sulfate), filtered and concentrated to a solid. The solid was dried by azeotroping with toluene (2×100 mL). The resulting tan solid was dissolved in 2-methyl tetrahydrofuran (500 mL) at 60° C. and methanol-d (40 mL; 2V) was added followed by solid potassium t-butoxide (1.1 g; 9.80 mmol; 0.2 eq). The solution was heated for 3 h at 60° C. LCMS showed 96-97% D after 3 h. The reaction solution was cooled to room temperature washed with aqueous 10% w/w ammonium chloride solution (200 mL; 10 V). The organic layer was separated and washed 3 times with water (200 mL each). The organic solution was filtered, concentrated and azeotropically dried with toluene. The solid was dissolved in 2-methyl tetrahydrofuran (560 mL) at 80° C. The reaction solution was cooled to 75° C., seeded with Form A (200 mg). The mixture was stirred while the temperature was cooled to 22° C. and kept for 1 h. The mixture was stirred at 0-5° C. for 1 h. The resulting solid was filtered, washed with cold 2-methyl tetrahydrofuran and dried in vacuum oven to obtain 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d Form A as an off white powder, (100 A % (by HPLC), chiral purity: 99.5%; 96.1% D (by LCMS); Pd 1 ppm; Ru 20 ppm, 84% yield) $^1$H NMR (400 MHz, DMSO-d6) δ 8.57 (s, residual un deuterated, 0.02H), 8.40 (dd, J=4.8, 1.5 Hz, 1H), 8.22 (d, J=2.3 Hz, 1H), 8.10 (dd, J=8.0,1.5, 1H), 7.72 (dd, J=8.6, 2.4 Hz, 1H), 7.36 (dd, J=8.0, 4.8, 1H), 6.88 (d, J=8.6 Hz, 1H), 6.76 (d, J=1.9, 1H), 6.50 (d, J=1.9, 1H), 5.40 (s, 2H), 4.72 (d, J=7.8 Hz, 1H), 4.26-4.29 (m, 1H), 3.87 (s, 3H), 3.70 (s, 3H), 1.03 (d, J=6.3 Hz, 3H)ppm. (M+1)=420

3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d Form A was further characterized by XRPD, PLM, DSC, TGA, and HPLC. The results are summarized in Table 2-1, indicating the starting material is a crystalline anhydrate.

Figure 20:
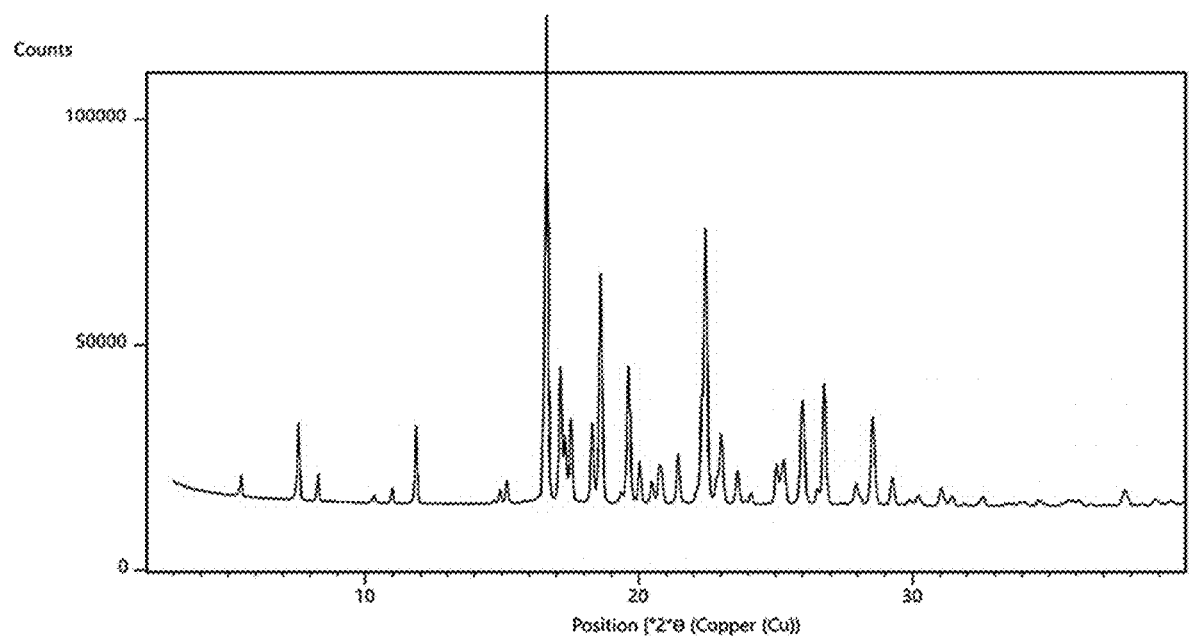
FIG. 20 shows an XRPD pattern of Compound 6 Form A.
Figure 21:
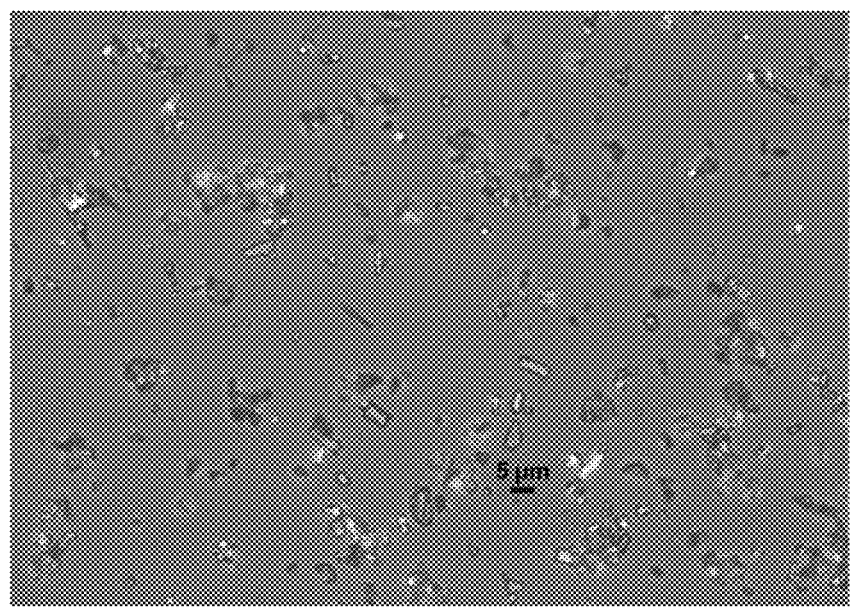
FIG. 21 shows a PLM image of Compound 6 Form A.
Figure 22:
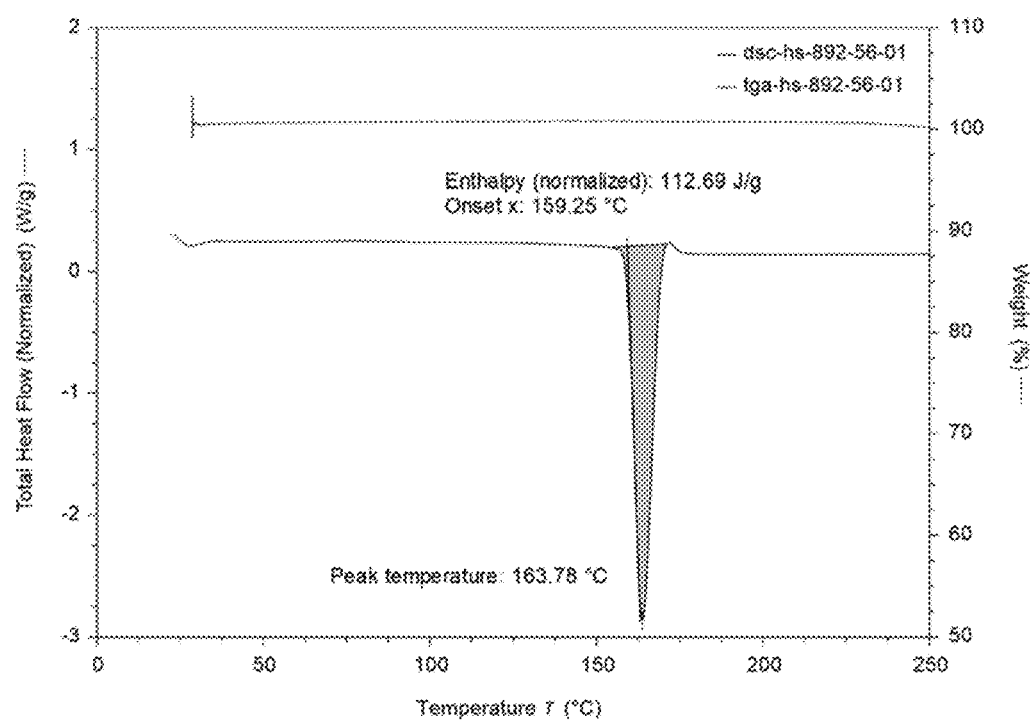
FIG. 22 shows a TGA (top pattern)/DSC (bottom pattern) overlay of Compound 6 Form A.
Figure 23:
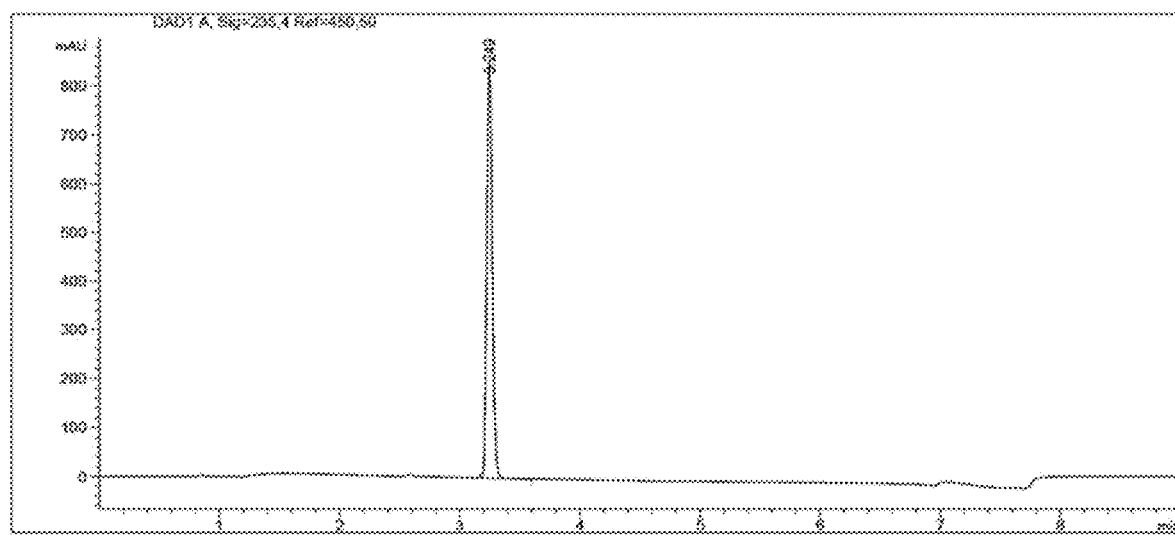
FIG. 23 shows HPLC of Compound 6 Form A.

| Technique | Data | Results |
|---|---|---|
| XRPD | FIG. 20 | Highly crystalline |
| PLM | FIG. 21 | Plate shaped morphology |
| DSC | FIG. 22 | Endotherm at 163.8° C. (peak temp) |
| TGA | FIG. 22 | Negligible weight loss observed before 150° C. |
| HPLC | FIG. 23 | >99.9% |

Analytical Methods:
X-Ray Powder Diffraction (XRPD)
Instrument: Panalytical Empyrean Powder Diffractometer
Parameters: X-Ray tube Cu (Ka); tube voltage 45 kV; tube current 40 mA
Scan from 2 to 40 degrees 2-theta; 0.013 degrees/step; scan rate 6 degrees/min
Thermogravimetric Analysis (TGA)

Instrument: TA Instruments Discovery TGA Q5500
Parameters: Ramp 10° C. per minute, ambient temperature to 250/300 □C, 50 mL/min N$_2$ sweep
Differential Scanning Calorimetry (DSC)
Instrument: TA Instruments Discovery DSC
Parameters: Ramp 10° C. per minute from ambient temperature to 250/300° C. with 50 mL/min N$_2$ sweep
Polarized Light Microscopy (PLM)
Instrument: Nikon Eclipse Ci Pol
Camera: Nikon
Software: NIS-Elements image software
Samples were dispersed on a microscope slide as slurries or if dry, samples were dispersed with silicone oil and examined under transmitted polarized light.

Phospho cFMS Activity

Reagents and consumables were purchased from Sigma Aldrich, Gibco LifeTechnologies, BD Biosciences, Perkin Elmer, R&D Systems, Cell Signaling, Thermo Scientific (Pierce) and Santa Cruz Biotechnology. HEK293 cells overexpressing human cFMS (HEK293/hFMS) were cultured in RPMI media in T225 flasks and split twice a week. For the experiment, the cells were trypsinized, counted and diluted with serum-free Megacell media (Sigma Cat #M3817) to 600,000 cells/ml (30,000 cells/well). A serial dilution of test compounds was prepared by the Echo 555 (LABCYTE) using Echo LDV Plates, Cat #LP-0200; and 500 nl of each compound concentration was added to 96-well BD Biocoat poly-d-lysine plate (BD Cat #356640) in DMSO (0.5% final). 50 µL/well MegaCell serum-free media was then added to cover compounds before adding cells at 50 µL/well cells (30,000/well). The plates were spun down for 1 minute at 1000 rpm and then incubated on benchtop for 15-30 minutes; the plates were moved to a CO$_2$ incubator at 37° C. for overnight incubation. White 96-well Perkin Elmer OptiPlates (Cat #6005509) were pre-coated with 50 ng/well (100 µL/well) anti-cFMS/CSF-1R (C-20) (Santa Cruz Cat #sc-692) in PBS, sealed with a foil seal, spun down at 1000 rpm for one minute and incubated overnight at 4° C.

On the following day, the pre-coated OptiPlates plates were blocked with 200 ul/well 1% BSA in 1× PBST (PBS with 0.1% Triton-X) at room temperature for 2-3 hours. In parallel, 100 µL/well 2× hCSF$_1$ (final 150 ng/ml) (R&D Systems, Cat #216-MC-025/CF) (or media as a negative control) was added to the HEK293/hFMS cells (BD culture plates) incubated overnight with compounds. On every plate 100% response (with CSF$_1$ treatment) and 0% response (without CSF$_1$) control columns were used to calculate percent inhibition of tested compounds and a Z' prime value. Plates were incubated at 37° C. for 10 minutes. Media/hCSF1 was aspirated off and cells were lysed with 100 ul/well pre-chilled lysis buffer made up with lysis buffer (Cell Signaling Cat #9803), protease/phosphatase inhibitors (Pierce Cat #78444), and PMSF (Sigma Cat #93482). Plates were shaken for 60 seconds; then, spun at 3200 rpm for 5 minutes at 4° C. and kept on ice. 90 ul of the lysate was transferred to the pre-coated/blocked OptiPlates. The plates were then spun at 1000 rpm for 60 seconds and incubated overnight at 4° C. sealed.

The next day lysates were removed from the plates; and plates were washed with 300 µL/well of 1× PBS 6 times using the Biotek washer. The remaining PBS on the plates was tapped out. 90 µL/well of 1:10,000 anti-phospho-Eu (Tyr 100) (Perkin Elmer Cat #AD0159) in 1% BSA in PBST was added to the plates; and plates were incubated for one hour at room temperature sealed. After one hour, the antibody was removed and plates were washed 6 times with 300 µL/well of PBST using the Biotek washer. 90 µL/well enhancement solution (Perkin Elmer Cat #4001-0010) was added next and the plates were sealed and shaken for 5 minutes. The signal was read immediately on the Perkin Elmer Envision for time-resolved fluorescence with excitation at 320 nm and emission at 615 nm.

The data were analyzed by Pipeline Pilot to calculate IC$_{50}$ values; IC$_{50}$ values for phosphor c-FMS are provided for selected CSF-1R inhibitors in Table B, below.

TABLE B

| Compound | phosphor c-FMS IC$_{50}$ (µM) |
|---|---|
| 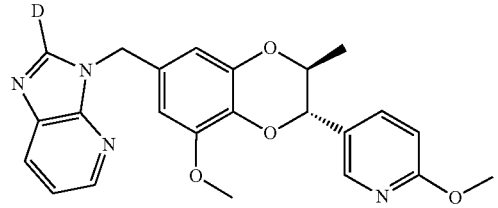 [SMILES: [2H]c1nc2cccnc2n1Cc1cc(OC)c2c(c1)O[C@@H](C)[C@H](c1ccc(OC)nc1)O2] Compound 6 | 0.009 |
| 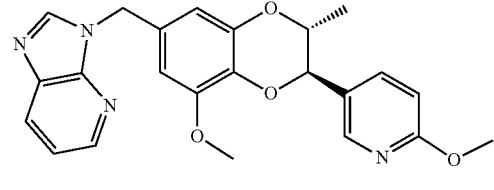 [SMILES: COc1ccc([C@H]2Oc3c(OC)cc(Cn4cnc5cccnc54)cc3O[C@@H]2C)cn1] | 0.633 |
| 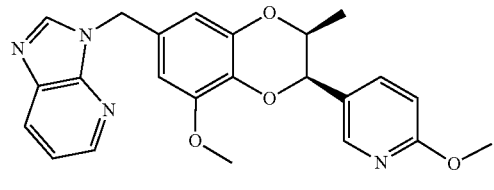 [SMILES: COc1ccc([C@H]2Oc3c(OC)cc(Cn4cnc5cccnc54)cc3O[C@H]2C)cn1] | 1.887 |
| 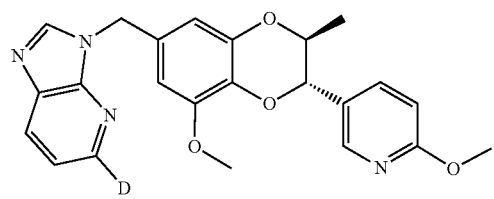 [SMILES: [2H]c1ccc2ncn(Cc3cc(OC)c4c(c3)O[C@@H](C)[C@H](c3ccc(OC)nc3)O4)c2n1] | 0.012 |
| 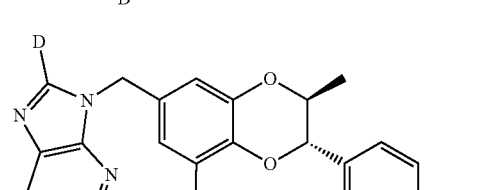 | 0.011 |
| 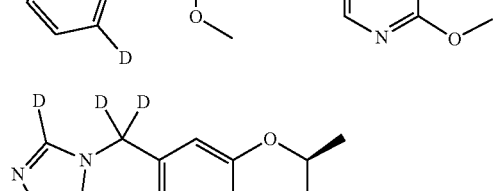 | 0.018 |

TABLE B-continued

| Compound | phosphor c-FMS IC$_{50}$ (μM) |
|---|---|
| (structure shown) | 0.034 |

Biological Examples (Examples 10-17xx): In Vitro Studies

Example 10

To compare the impact of a CSF-1R inhibitory compound and a deuterated CSF-1R inhibitory compound of this disclosure on cytokine/chemokine production following CSF-1 stimulation, the following experiments were conducted in BV2 murine microglial cells.

Two different passages of BV2 mouse microglial cells were plated in different 96-well plates to provide biological quadruplicates.

| Grp # | Simulation Groups | Wells per group | Treatments |
|---|---|---|---|
| 1 | No Stimulation | 4 wells/passage | DMSO |
| 2 | CSF-1 Stimulation | 4 wells/passage | DMSO, Compound 24, or Compound 6 |

Test articles:
DMSO
Compound 24:

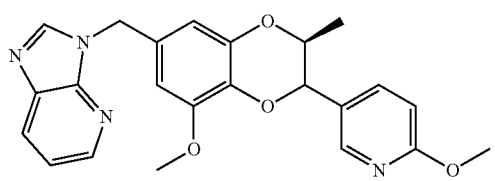 [SMILES: COc1ccc(C2Oc3c(OC)cc(Cn4cnc5cccnc54)cc3O[C@H]2C)cn1]

Compound 6

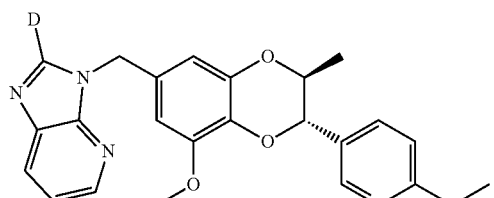

Recombinant mouse M-CSF (R&D Systems, cat #416-ML/CF, lot #ME4518091)—Prepared 100 μg/mL stock solution by dissolving 50 μg in 500 μl PBS and treated with 100 ng/mL.
Compound 24 was prepared in accordance with the procedure outlined in Example 1-92 of WO2017/015267.

Both test compounds were prepared in diluted stock solution (10 mM) with culture media to get a 100 μM working solution and treated at 3.125 nM, 6.25 nM, 12.5 nM, 25 nM, 50 nM, 100 nM, 200 nM or 400 nM.

Methods
Treatment and Stimulation of BV2 Microglial Cells

BV2 mouse microglia were suspended at a concentration of $5 \times 10^5$ cells/mL and 100 μL of this cell suspension was added to each well of a 96-well plate. Microglia cells were allowed to rest overnight at 37° C., 5% $CO_2$. The following day, the media was removed and cells were treated with either dimethyl sulfoxide (DMSO), Compound 24, or Compound 6 for 30 minutes at 37° C., 5% $CO_2$. Cells were then stimulated with 100 ng/mL recombinant mouse M-CSF for 24 hours. After stimulation, the culture supernatant was removed from each well and aliquoted into two different 96-well plates for subsequent ELISA assays.

Mouse MCP-1 ELISA

Culture supernatants were assayed with the Quantikine Mouse MCP-1 ELISA kit from R&D Systems. Samples were diluted 1:10 with Calibrator Diluent. Fifty microliters of Assay Diluent were first added to each well. Fifty μL of Standards, Assay Control and diluted Sample were then added to the wells. The plate was mixed by gently tapping the frame, and sealed with an adhesive strip. The plate was incubated for 2 hours at room temperature. After incubation, the plate was washed with approximately 400 μL of Wash Buffer using a squirt bottle 5 times. After the last wash, the plate was gently tapped on paper towels to remove excess moisture. 100 μL of mouse MCP-1 conjugate was added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the ELISA plate reader at 450 nm.

Results

BV2 murine microglia were plated at 50,000 cells per well and rested overnight. Cells were pre-treated with DMSO, Compound 24, or Compound 6 for 30 minutes, and then subjected to CSF-1 stimulation. Cell culture supernatants from this experiment were processed in an MCP1 ELISA to determine whether stimulation/treatment impacted chemokine production. As seen in FIGS. 1A-1B and FIGS. 2A-2B, CSF-1 stimulation induced a significant increase in the release of MCP-1 (CCL2—chemokine) and both small molecule CSF-1R inhibitors significantly reduced MCP-1 production in a concentration dependent manner. Percent inhibition was calculated based upon unstimulated and stimulated controls and IC$_{50}$ curves were generated. As seen in FIGS. 3A-3B and 4A-4B, both compounds exhibit a similar IC$_{50}$ value for this assay between 28.8 nM-36.5 nM.

Graphical columns represent the mean and standard deviation. Statistical significance was determined with a one-way ANOVA with multiple comparisons and p values are represented by *$p<0.05$, $p<0.01$, *$p<0.001$, and ****$p<0.0001$.

Example 11

To compare the effect of two CSF-1R inhibitory compounds and one deuterated CSF-1R inhibitory compound of this disclosure on microglial cytokine/chemokine production following CSF-1 stimulation, the following experiment was conducted in primary murine microglial cells.

Primary Mouse Microglial Cells

| Grp # | Simulation Groups | Wells per group | Treatments |
| --- | --- | --- | --- |
| 1 | No Stimulation | 6 wells | DMSO |
| 2 | CSF-1 Stimulation | 6 wells | DMSO, Compound 49, PLX3397, Compound 6 |

Test articles:
 DMSO
 Compound 49

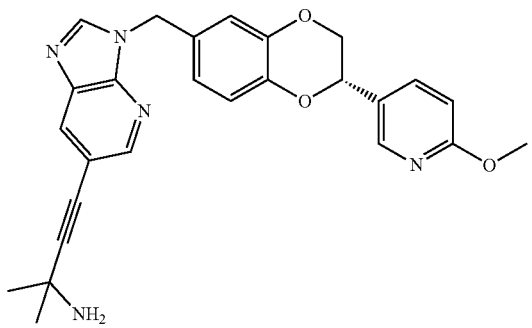 [SMILES: COc1ccc([C@H]2COc3cc(Cn4cnc5cc(C#CC(C)(C)N)cnc54)ccc3O2)cn1]

PLX3397 (pexidartinib)

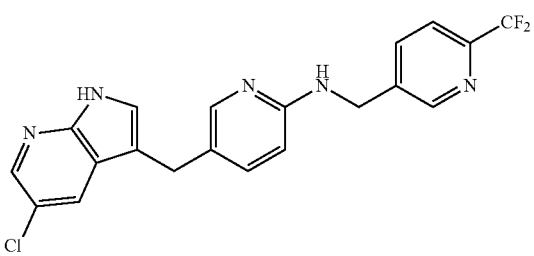

Compound 6

Recombinant mouse CSF-1 (R&D Systems, cat #416-ML/CF, lot #ME4518091)—Prepared 100 μg/mL stock solution by dissolving 50 μg in 500 μL PBS and treated microglia with 100 ng/mL.

Compound 49 was prepared in accordance with the procedure outlined in Example 1-5 of WO2017/015267.

All test compounds were prepared in diluted stock solution (10 mM) with culture media to get a 100 μM working solution and treated at 3.125 nM, 6.25 nM, 12.5 nM, 25 nM, 50 nM, 100 nM, 200 nM or 400 nM.

Methods

Treatment and Stimulation of Primary Microglial Cells

Primary mouse microglia were suspended at a concentration of $5\times10^5$ cells/mL and 100 μL of this cell suspension was added to the inner 60 wells of three 96-well plates. Microglia cells were allowed to rest overnight at 37° C., 5% $CO_2$. The following day, the media was removed, and cells were treated with either dimethyl sulfoxide (DMSO), Compound 49, PLX3397, or Compound 6 for 30 minutes at 37° C., 5% $CO_2$. Cells were then stimulated with 100 ng/mL recombinant mouse CSF-1 for 24 hours. After stimulation, the culture supernatant was removed from each well and aliquoted into two different 96-well plates for subsequent ELISA assays. Plates were fixed with 4% PFA for future immunocytochemistry analysis.

Mouse MCP-1 ELISA

Culture supernatants were assayed with the Quantikine Mouse MCP-1 ELISA kit (R&D Systems, cat #SMJE00B). Samples were diluted 1:10 with Calibrator Diluent. Fifty microliters of Assay Diluent were first added to each well. Fifty microliters of Standards, Assay Control and diluted Sample were then added to the wells. The plate was mixed by gently tapping the frame and sealed with an adhesive strip. The plate incubated for 2 hours at room temperature. After incubation, the plate was washed with approximately 400 μL of Wash Buffer using a squirt bottle 5 times. After the last wash, the plate was gently tapped on paper towels to remove excess moisture. 100 μL of mouse MCP-1 conjugate was added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the FlexStation3 Multi-Mode Microplate Reader (Molecular Devices, cat #Flex3) with SoftMax Pro Software at 450 nm.

Immunostaining of Primary Microglia

Following the stimulation, cells were fixed with 4% PFA for 20 minutes at room temperature. Cells were then rinsed in PBS, washed 3×5 minutes in 0.2% PBT (0.2% Triton X-100 in PBS) and blocked with 10% donkey serum/0.2% PBT for 1 hour at room temperature. Cells were then incubated in primary antibody (rabbit anti-Iba1, 1:500; Wako, cat #019-19741 or rabbit anti-Ki67, 1:500; Abcam, cat #ab15580) diluted in 10% donkey serum/0.2% PBT overnight at 4° C. The next day, cells were washed 3×5 minutes in 0.2% PBT and incubated in secondary antibody (donkey anti-rabbit Alexa Fluoro 488, 1:500; Life Technologies, cat #A21206) diluted in 1% donkey serum/0.2% PBT for 1 hour at room temperature. Cells were then washed 3×5 minutes in 0.2% PBT, incubated in DAPI (1:10,000 in PBS) for 5 minutes at room temperature, and rinsed in PBS.

Microscopy

After staining, plates were imaged on the IN Cell Analyzer 2200 with 9 fields of view acquired per well. The quantification was performed on the IN Cell Developer Analysis software, calculating the sum of the area (in $\mu m^2$) of IBA1 staining or the number of Ki67+ cells for the 9 fields. The average value per field in each well (typically 6-9 fields per well as certain fields excluded due to staining artifact) was calculated for each technical triplicate and normalized to the average of the DMSO control wells. A one-way ANOVA was used to determine the statistical significance of differences between samples. Statistical analysis was performed with Prism 6 (GraphPad Software) and p values are indicated by *≤0.05, ≤0.01, *≤0.001, and ****≤0.0001.

Results

Figure 5A:
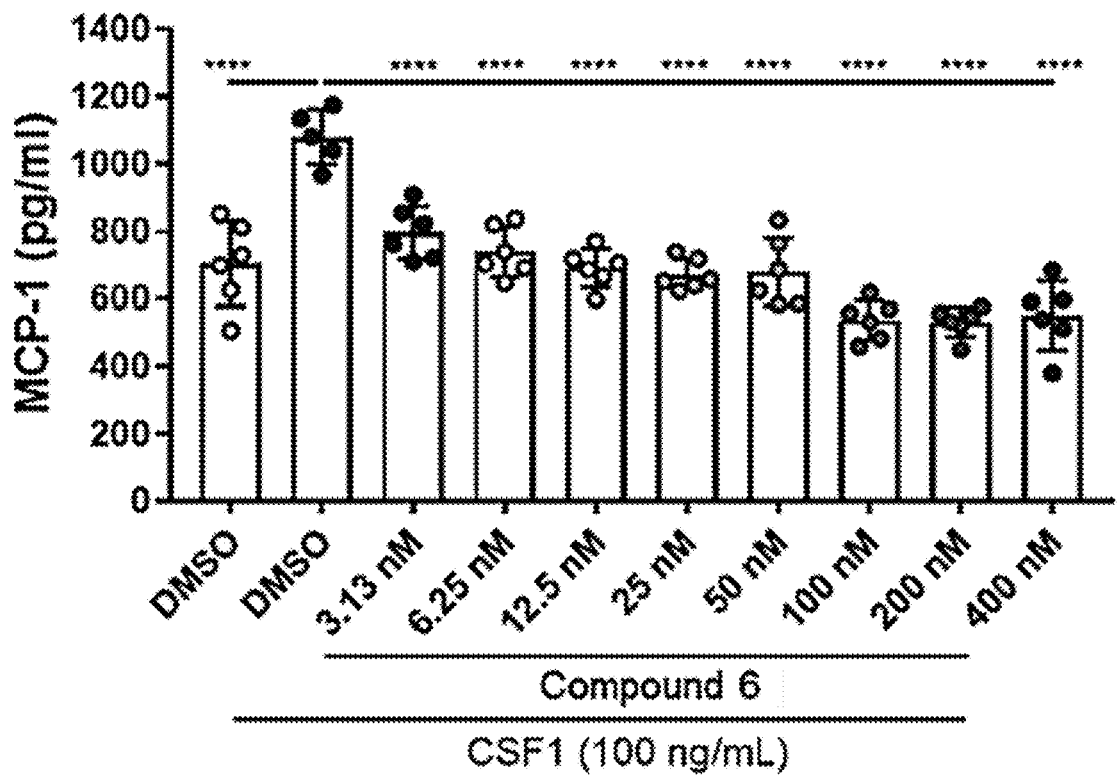
FIGS. 5A-5C show the CSF-1R inhibitors Compound 6 (FIG. 5A) and the PLX3397 control (FIG. 5C) significantly reduced MCP-1 production in a concentration dependent manner. Results for Compound 49 are shown in FIG. 5B.
Figure 5B:
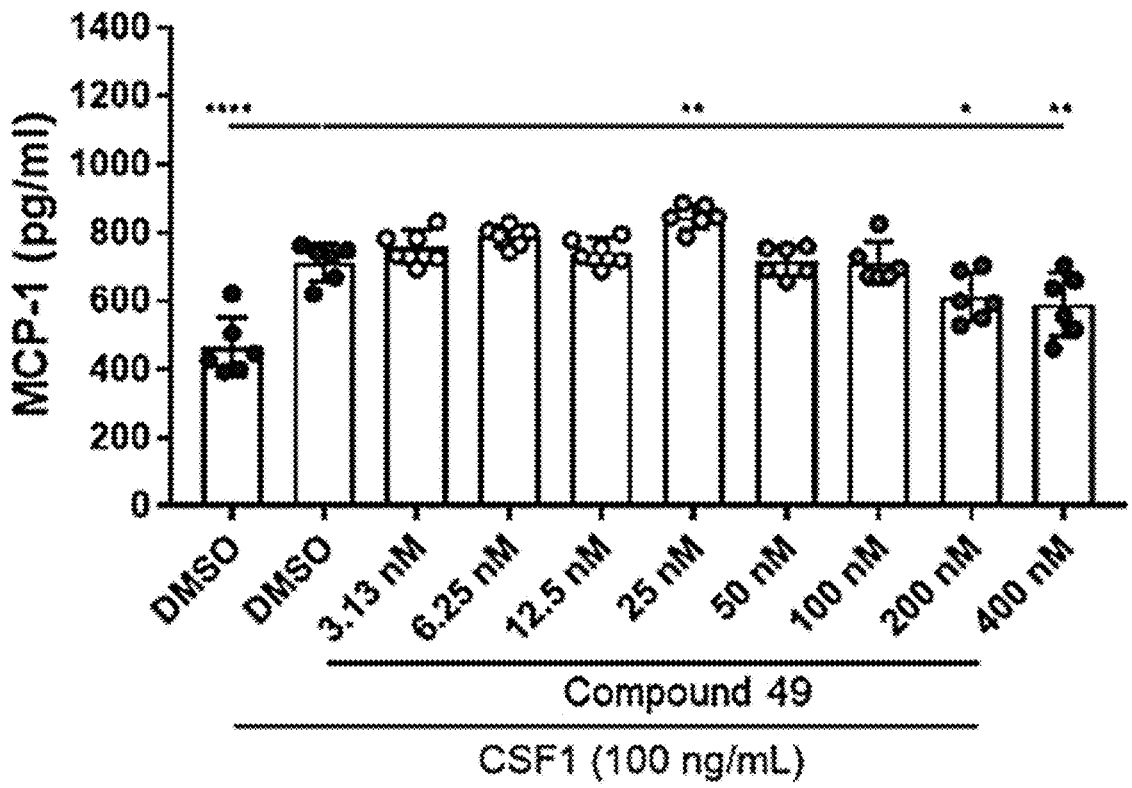
Figure 5C:
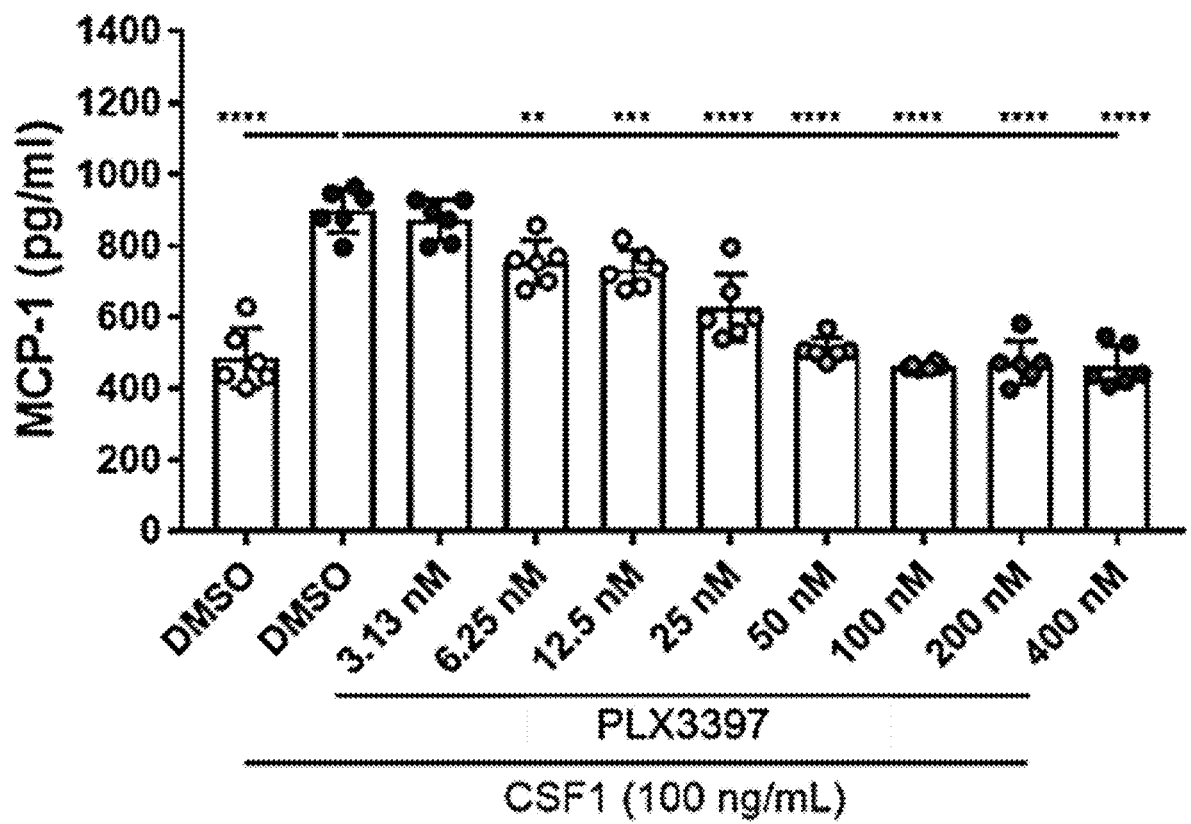

Primary murine microglia were plated at 50,000 cells per well and rested overnight. Cells were pre-treated with DMSO, Compound 49, PLX3397 or Compound 6 for 30 minutes, and then subjected to CSF-1 stimulation. Cell culture supernatants from this experiment were processed in a MCP1 ELISA to determine whether stimulation/treatment impacted chemokine production. As seen in FIGS. 5A-5C, CSF-1 stimulation induced a significant increase in the release of MCP-1 (CCL2—chemokine.) The CSF-1R inhibitors PLX3397 and Compound 6 significantly reduced MCP-1 production in a concentration dependent manner (Ordinary one-way ANOVA, p<0.0001.) $IC_{50}$ values were calculated for both PLX3397 ($IC_{50}$=17.4 nM) and Compound 6 ($IC_{50}$=23.2 nM). CSF-1-induced MCP-1 production was not robust in the plate for treated with Compound 49 (FIG. 5B), so an $IC_{50}$ value for this compound could not be generated. MCP-1 secretion was assessed after 24 hours utilizing R&D MCP-1 Elisa Kit. Each data point represents a single well while graphical columns represent the mean and standard deviation of six wells.

Following a microglial stimulation, immunocytochemistry was completed with Iba1, Ki67, and DAPI to determine microglial morphology, proliferative state, and number. InCell imaging microscope and analysis software was used to quantify Iba1$^+$ area, and the number of DAPI$^+$ nuclei within the cultures. Ki67 could not be quantified because condensation during ICC cross-transferred Ibalantibody into Ki67 wells. The quantitative results (FIGS. 6A-6C and 7A-7C) demonstrate a significant effect of CSF-1 stimulation on Iba1$^+$ area and DAPI$^+$ cell number, respectively. CSF-1R inhibition can be seen to block these CSF-1-induced cell changes in a concentration-dependent manner. $IC_{50}$ values were calculated for both PLX3397 ($IC_{50}$=50.43 nM for Iba1 and 68.2 nM for DAPI) and Compound 6 ($IC_{50}$=84.6 nM for Iba1 and 248 nM for DAPI).

Figure 6A:
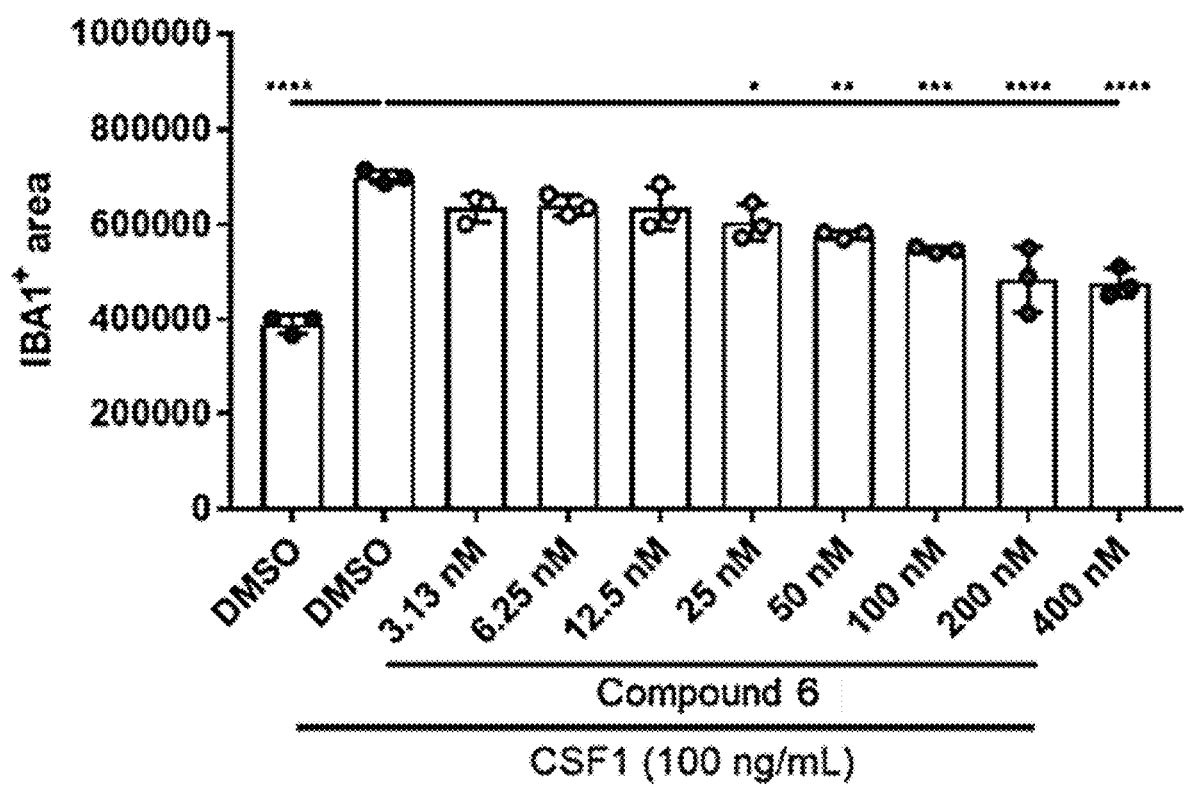
FIGS. 6A-6C show that CSF-1 stimulation significantly increases the Iba1$^+$ area, and treatment with the CSF-1R inhibitors Compound 6 (FIG. 6A) and control PLX3397 (FIG. 6C) significantly abrogated this effect in a concentration dependent manner. Results for Compound 49 are shown in FIG. 6B.
Figure 6B:
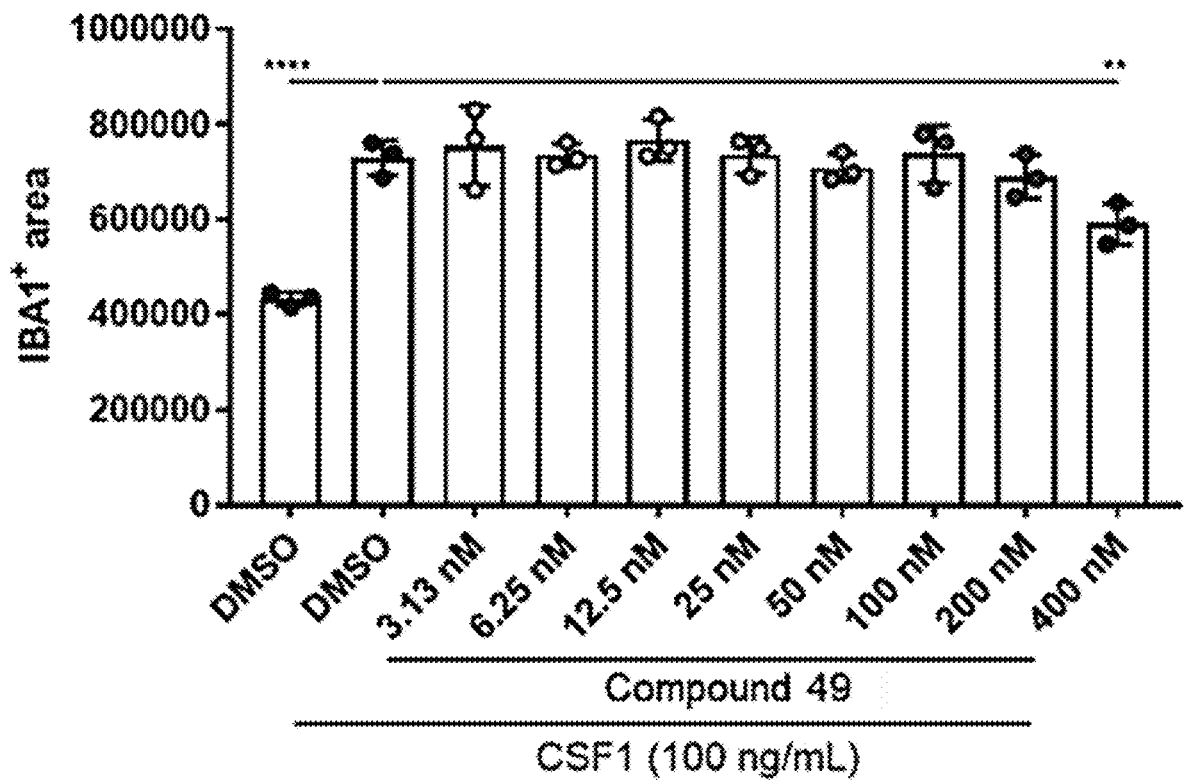
Figure 6C:
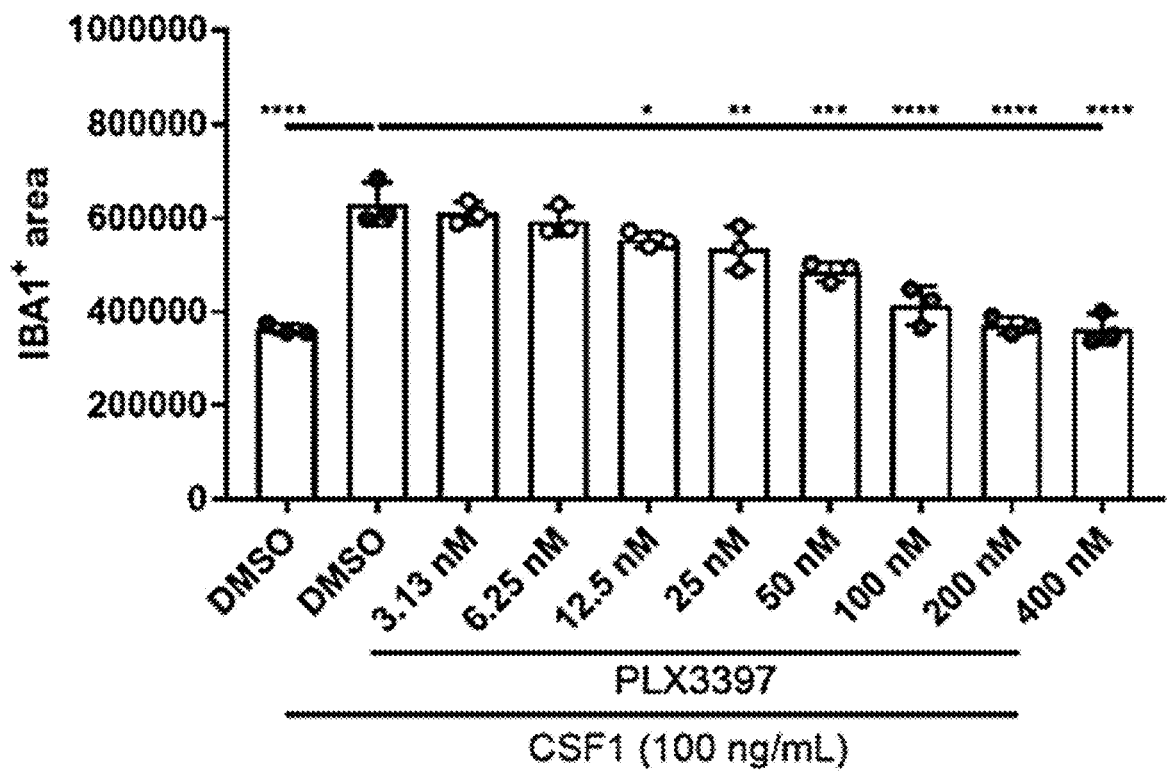

In FIGS. 6A-6C, Iba1$^+$ area was quantified following a microglial stimulation assay. CSF-1 stimulation significantly increases the Iba1$^+$ area and treatment with CSF-1R inhibitors significantly abrogated this effect in a concentration dependent manner. The microglial area was quantified from nine images taken from three different wells for each condition. Data points represent the average Iba1$^+$ area per well and error bars represent the standard deviation (n=3). Statistical significance was determined by a one-way ANOVA and p values are indicated by *$p<0.05$, $p<0.01$, *$p<0.001$, and ****$p<0.0001$.

Figure 7A:
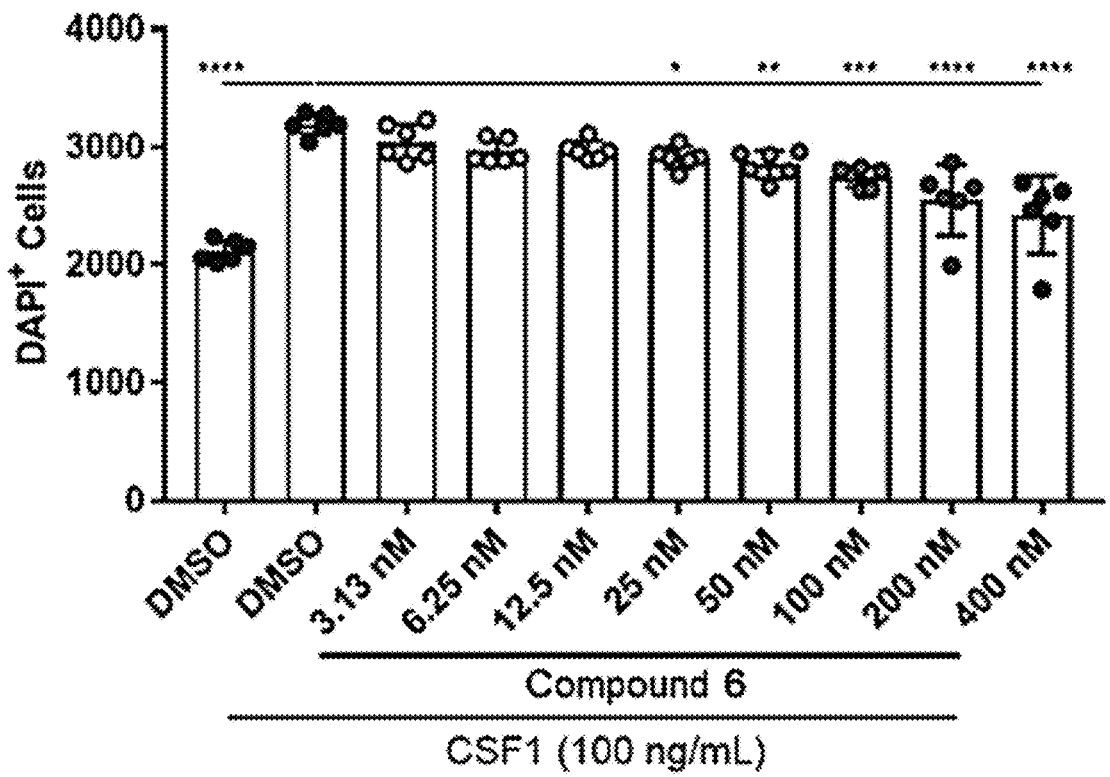
FIGS. 7A-7C show that CSF-1 stimulation increases the number of cells within the culture (as evidence by DAPI$^+$ cells), and that CSF-1R inhibitors Compound 6 (FIG. 7A) and control PLX3397 (FIG. 7C) reduce this number in a concentration dependent manner. Results for Compound 49 are shown in FIG. 7B.
Figure 7B:
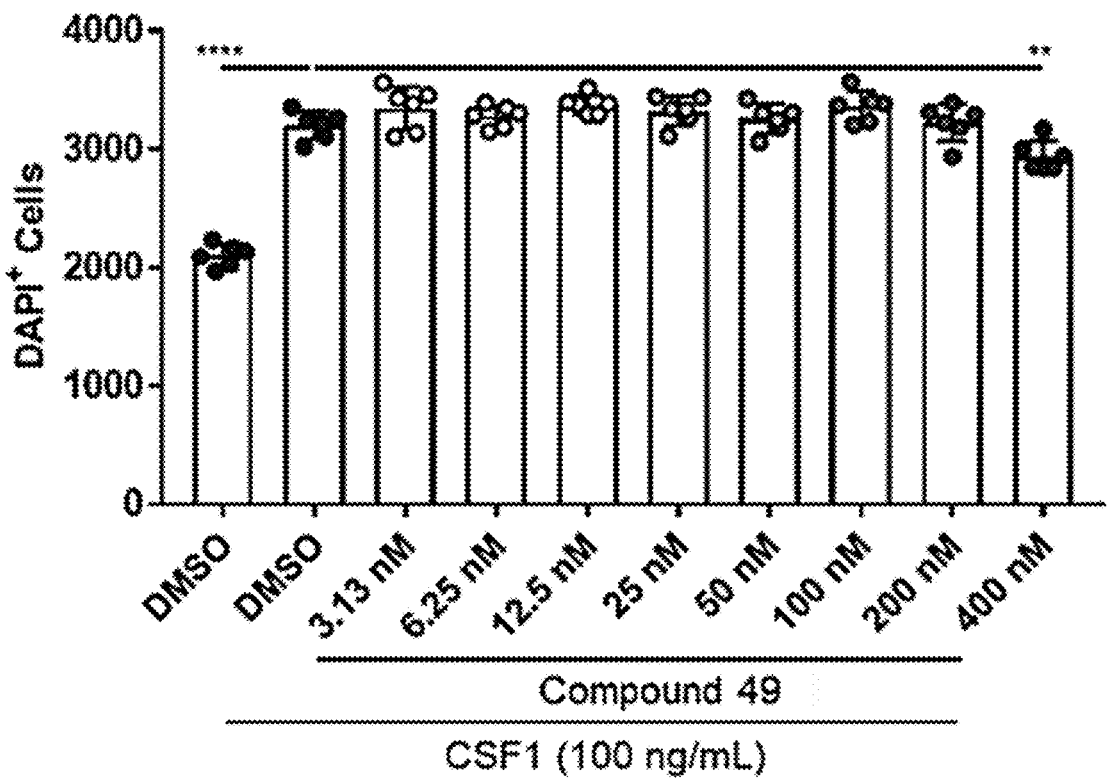
Figure 7C:
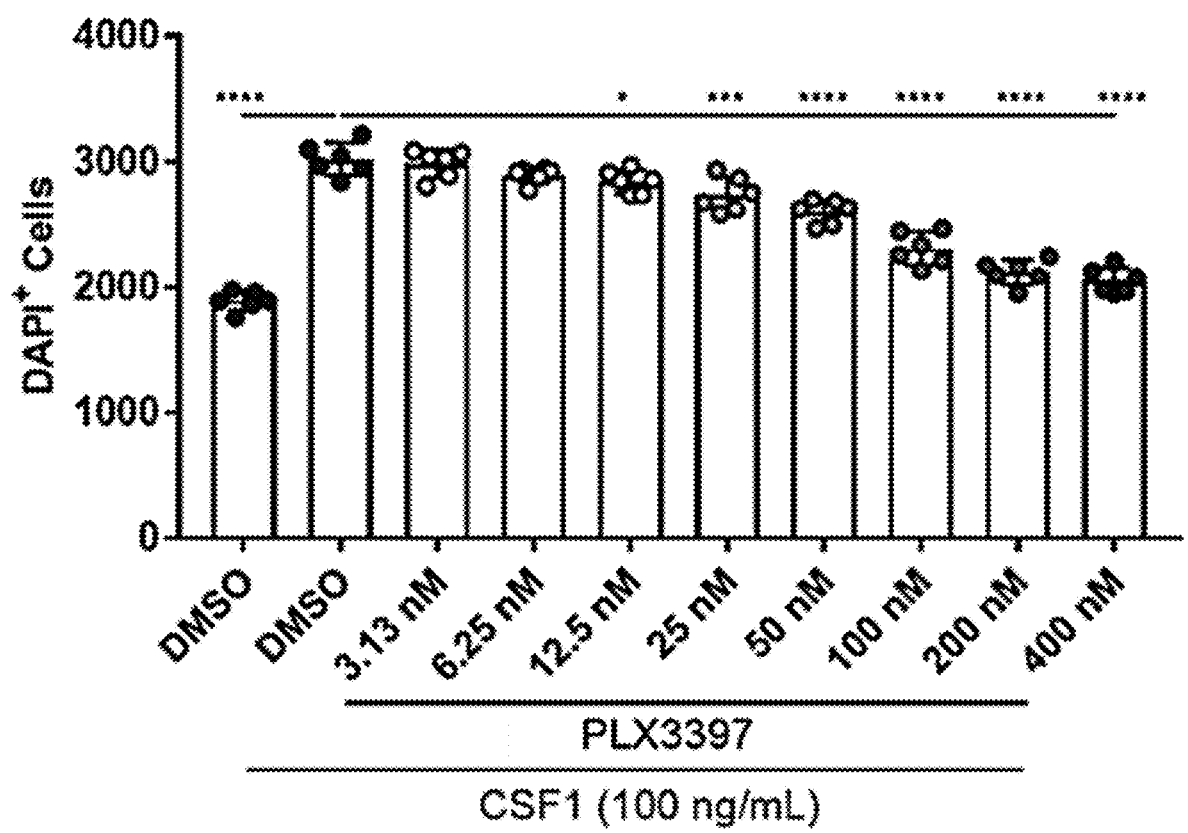

In FIGS. 7A-7C, DAPI$^+$-labeled nuclei were quantified with following a microglial stimulation assay. CSF-1 stimulation increases the number of cells within the culture and CSF-1R inhibitors reducing this number in a concentration dependent manner. The DAPI$^+$ nuclei were quantified from nine images taken from three different wells for each condition. Data points represent the average Iba1$^+$ area per well (from 9 images) and error bars represent the standard deviation (n=3). Statistical significance was determined by a one-way ANOVA and p values are indicated by *$p<0.05$, $p<0.01$, *$p<0.001$, and ****$p<0.0001$.

Example 12

The impact of a deuterated CSF-1R inhibitor of this disclosure on cytokine/chemokine production following CSF-1 or LPS stimulation in wild-type versus SOD1 mutant primary microglial cells was examined in the following experiments.
Primary Mouse Microglial Cells—Isolated in ELN 20200624-062

| Grp # | Simulation Groups | Wells per group | Treatments |
|---|---|---|---|
| 1 | No Stimulation | 6 wells/genotype | DMSO |
| 2 | CSF-1 Stimulation | 6 wells/genotype | DMSO, Compound 6 |
| 3 | LPS Stimulation | 6 wells/genotype | DMSO, Compound 6 |

Test Articles:
DMSO
Compound 6—Diluted stock solution (10 mM) with culture media to get a 100 μM working solution and treated microglia at 50 nM, 100 nM, or 200 nM.
Recombinant mouse M-CSF (R&D Systems, cat #416-ML/CF, lot #ME4518091)—Prepared 100 μg/mL stock solution by dissolving 50 μg in 500 μl PBS and treated microglia with 100 ng/mL.
Lipopolysaccharide, from *Escherichia coli* 055:B5 (Sigma, cat #L6529-1 mg, lot #059M4103V)—Made 0.2 mg LPS/mL PBS stock and treated microglia with 10 ng/mL.
Methods
Treatment and Stimulation of Primary Microglial Cells
Primary mouse microglia were suspended at a concentration of 5×10$^5$ cells/mL and 100 μL of this cell suspension was added to each well of a 96-well plate. Microglia cells were allowed to rest overnight at 37° C., 5% $CO_2$. The following day, the media was removed and cells were treated with either dimethyl sulfoxide (DMSO) or Compound 6 for 30 minutes or 24 hours at 37° C., 5% $CO_2$. Cells were then stimulated with 100 ng/mL recombinant mouse M-CSF for 30 minutes or 10 ng/mL lipopolysaccharide for 24 hours. After stimulation, the culture supernatant was removed from each well and aliquoted into two different 96-well plates for subsequent ELISA assays.
CellTiter Glo 2.0 Viability Assay
Cell viability was determined using Promega's Cell Titer Glo Luminescent Cell Viability Assay. The assay reagent was first allowed to equilibrate to room temperature for 30 minutes. After culture supernatants were removed, 100 μL fresh room temperature media was added to each well. Subsequently, 100 μL of assay reagent was added to each well. The assay plate was then shaken for two minutes and left to rest for 10 minutes. 100 μL was transferred from each well to a white plate and luminescence was read immediately on the FlexStation3 plate reader.
Mouse MCP-1 ELISA
Culture supernatants were assayed with the Quantikine Mouse MCP-1 ELISA kit from R&D Systems (cat #SMJE00B). Samples were diluted 1:10 with Calibrator Diluent. Fifty microliters of Assay Diluent were first added to each well. Fifty microliters of Standards, Assay Control and diluted Sample were then added to the wells. The plate was mixed by gently tapping the frame, then sealed with an adhesive strip. The plate incubated for 2 hours at room temperature. After incubation, the plate was washed with approximately 400 μl of Wash Buffer using a squirt bottle 5 times. After the last wash, the plate was gently tapped on paper towels to remove excess moisture. One hundred microliters of mouse MCP-1 conjugate were added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the ELISA plate reader at 450 nm.
Mouse IL-12p40 ELISA
Cell culture supernatants were assayed with the Quantikine Mouse IL-12p40 ELISA kit from R&D Systems (cat #MP400). Samples were diluted 1:10 with Calibrator Diluent. Fifty microliters of Assay Diluent were first added to each well. Fifty microliters of Standards, Assay Control and diluted Sample were then added in singlicate to the wells. The plate was mixed by gently tapping the frame, then sealed with an adhesive strip. The plate incubated for 2 hours at room temperature. After incubation, the plate was washed with approximately 400 µl of Wash Buffer using a squirt bottle 5 times. After the last wash the plate was gently tapped on paper towels to remove excess moisture. One hundred microliters of mouse IL-12p40 conjugate were added to each well, covered with a new strip of adhesive tape, and incubated at room temperature for 2 hours. After incubation, the plate was washed as described above. Substrate Solution was then added to each well and incubated for 30 minutes at room temperature in the dark. After incubation, the acid stop solution was added to each well, and the plate was read on the ELISA plate reader at 450 nm.

Results

Primary murine microglia were plated at 50,000 cells per well and rested overnight. Cells were pre-treated with DMSO or Compound 6 for 30 minutes or 24 hours, and then subjected to CSF-1 or LPS stimulation respectively. Cell viability was assessed after 24 hours utilizing Promega's Cell Titer Glo Assay Kit. Both CSF-1 and LPS stimulation induced a slight increase in the cell viability readout versus unstimulated cells (FIGS. 8A-8B and FIGS. 9A-9B).

Figure 8A:
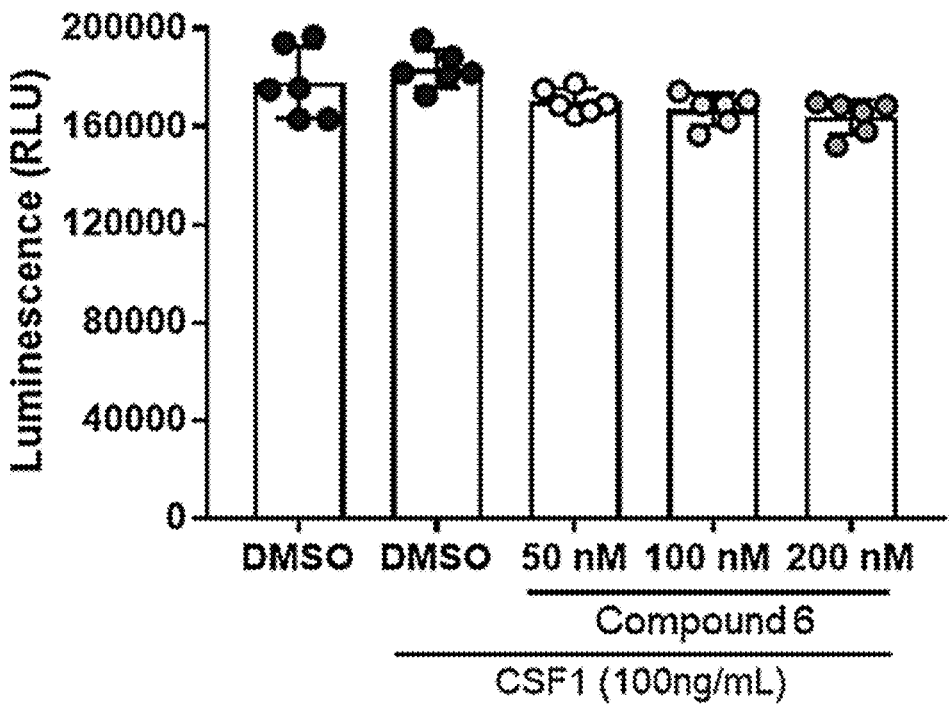
FIGS. 8A-8B show cell viability following pre-treatment with DMSO (control) or Compound 6 and CSF-1 stimulation in wild type (FIG. 8A) or SOD1 (FIG. 8B) cells.
Figure 8B:
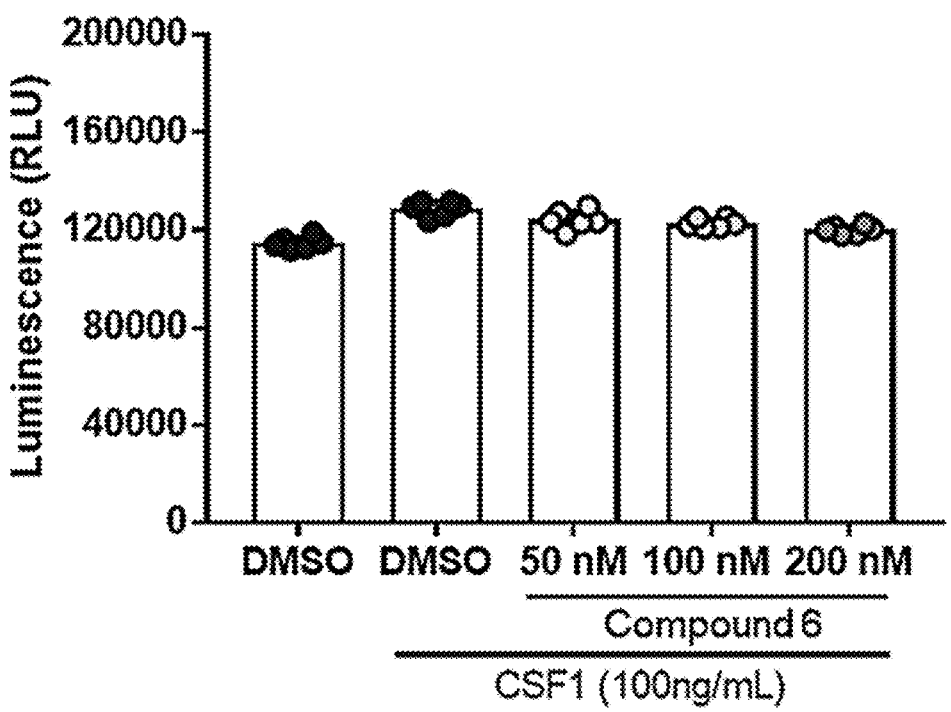
Figure 9A:
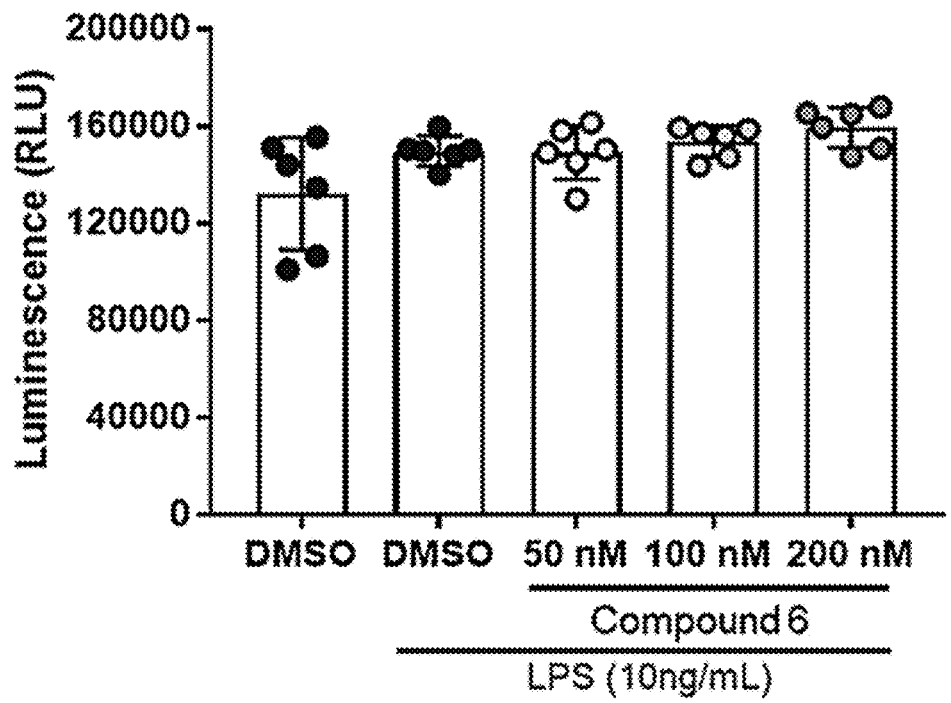
FIGS. 9A-9B show cell viability following treatment with DMSO (control) or Compound 6 and LPS stimulation in wild type (FIG. 9A) or SOD1 (FIG. 9B) cells.
Figure 9B:
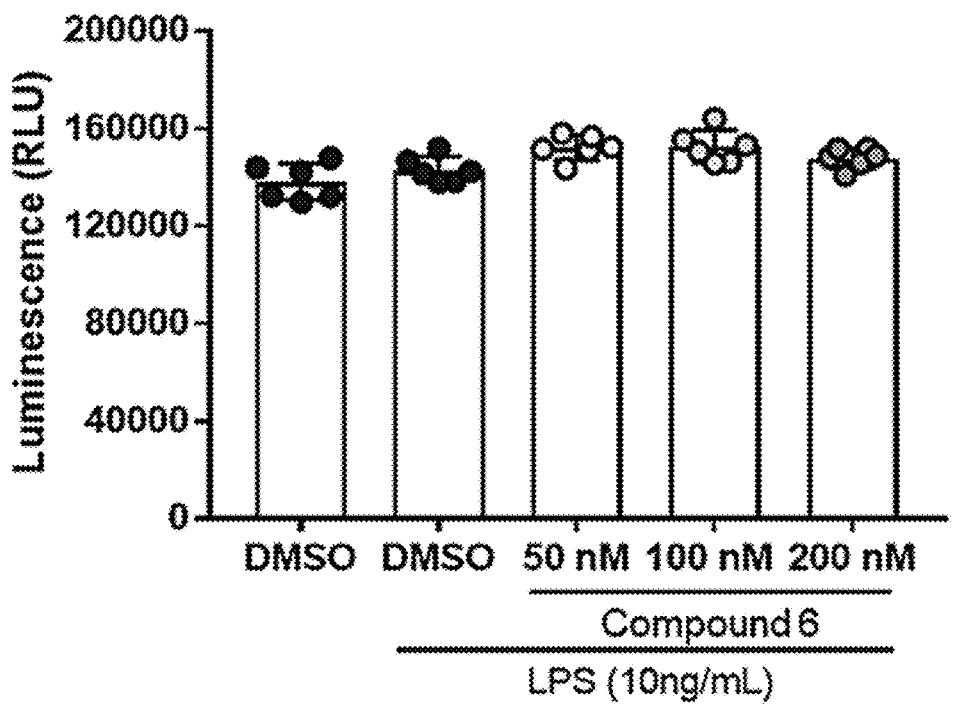

As seen in FIGS. 8A and 8B, CSF-1R inhibitor treatment had no toxic effect on microglia at the concentrations assessed. The deuterated CSF-1R inhibitor, Compound 6, slightly reduced the CSF-1-induced increase in cell viability. Graphical columns represent the mean and standard deviation of six wells. As seen in FIGS. 9A-9B, CSF-1R inhibition had no deleterious effect on cell viability. Graphical columns represent the mean and standard deviation of six wells. No significant differences were observed in wild-type versus SOD1 microglia cell viability in response to CSF-1 or LPS stimulation.

Cell culture supernatants from this experiment were processed in two separate ELISAs (MCP-1 and IL12p40) to determine whether stimulation/treatment impacted chemokine/cytokine production.

Figure 10A:
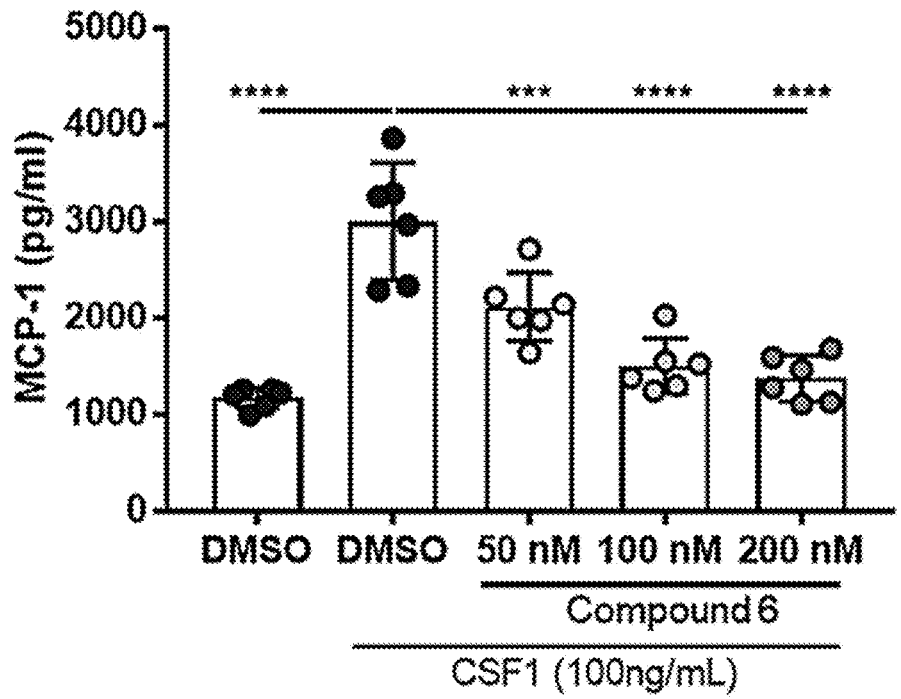
FIGS. 10A-10 show MCP-1 production following treatment with DMSO (control) or Compound 6 and CSF-1 stimulation in wild type (FIG. 10A) or SOD1 (FIG. 10B) cells.
Figure 10B:
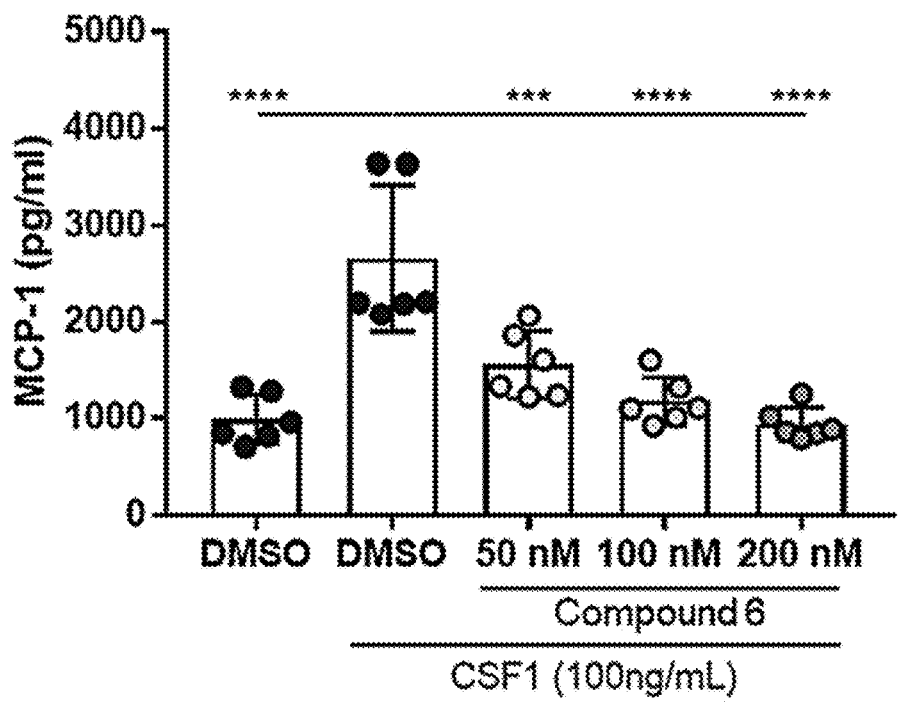

As seen in FIGS. 10A-10B, CSF-1 stimulation induced a significant increase in the release of MCP-1 (CCL2—chemokine) and Compound 6 significantly reduced MCP-1 production in a concentration dependent manner. Graphical columns represent the mean and standard deviation of six wells. An ordinary one-way ANOVA was performed to determine the statistical difference between groups and p values are represented by *$p<0.001$ and **$p<0.0001$.

Figure 11A:
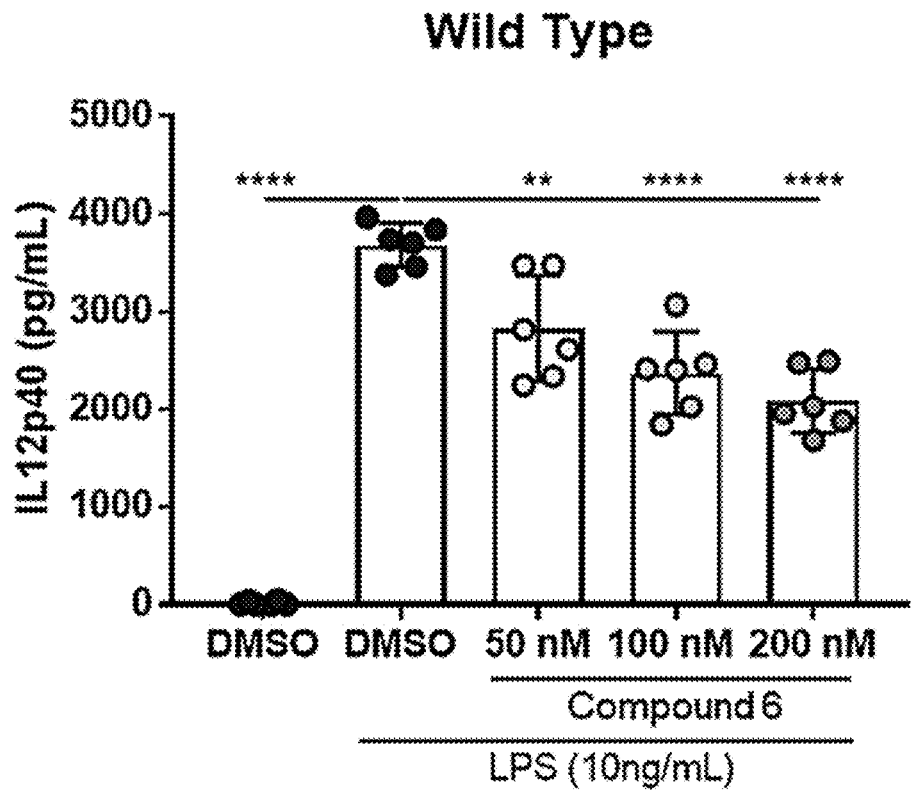
FIGS. 11A-11B show IL-12p40 production following treatment with DMSO (control) or Compound 6 and LPS stimulation in wild type (FIG. 11A) or SOD1 (FIG. 11B) cells.
Figure 11B:
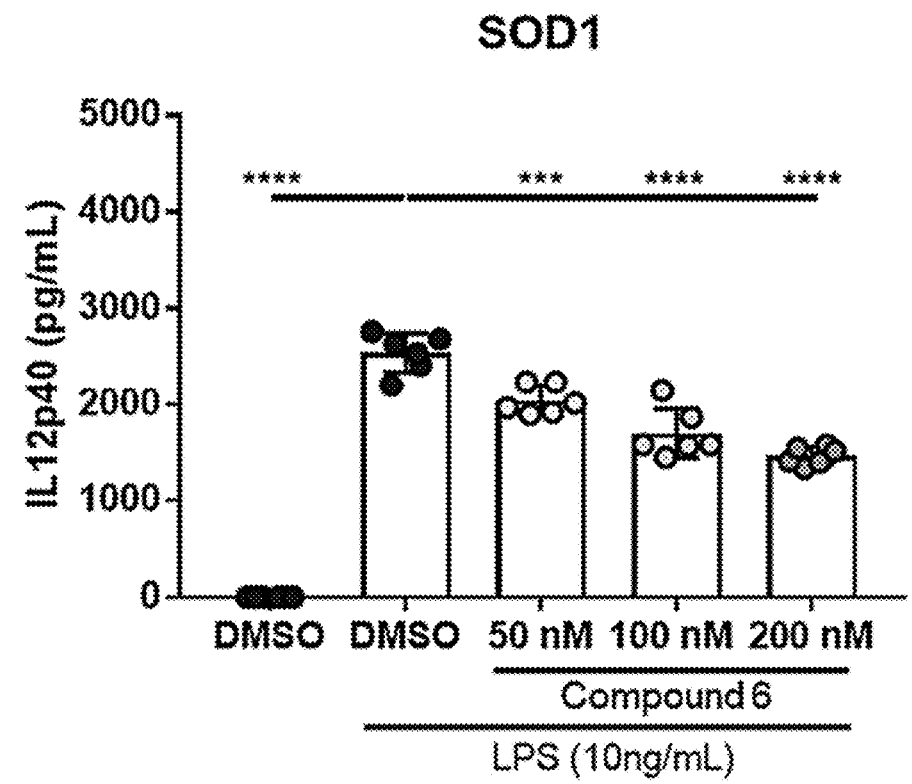

As seen in FIGS. 11A-11B, LPS stimulation induced a significant increase in IL12-p40 production in the murine microglial cultures. CSF-1R inhibition with Compound 6 significantly reduced IL12-p40 production in a concentration dependent manner. Graphical columns represent the mean and standard deviation of six wells. An ordinary one-way ANOVA was performed to determine the statistical difference between groups and p values are represented by $p<0.01$, *$p<0.001$, and ****$p<0.0001$.

Example 13

Caco-2 Permeability and Efflux Assay to Compare Compound 6 to Compound 24

Caco-2 permeability and efflux assays were performed in cell-based permeability model using Caco-2/TC7 cells. For permeability assays, Caco-2/TC7 cells were seeded on to Millipore Millicell 96 and for efflux assays, 24-well plates were used. The plates with cells were ready to use between 21-25 days of culturing. Both permeability and efflux assays were performed using the TECAN automated liquid handling platform. For permeability assays, test compounds were prepared at 20 µM test concentrations in permeability assay buffer (10 mM HEPES in HBSS buffer, pH 6.5) containing 0.5% BSA. Basolateral permeability buffer (pH 7.4) contains 5% BSA. For efflux assays, test compounds were prepared at 1 µM test concentrations in permeability assay buffer (10 mM HEPES in HBSS buffer, pH 7.4) containing 0.5% BSA. For efflux assays, the basolateral permeability buffer (pH 7.4) contained 0.5% BSA. The permeability assay was initiated by adding 20 µM test solution to apical side of plate containing Caco-2/TC7 cells. In the efflux assay, 1 µM test compound was added to an apical compartment for apical to basolateral (A to B) permeability determination. For basolateral to apical (B to A) permeability determination, the test compound was added to the basolateral side. The plate was incubated for 90 min under constant shaking at 37° C. At the end of the incubation period, samples taken were analyzed using high pressure liquid chromatography with tandem mass spectrometry. For each assay, apparent permeability ($P_{app}$) and recovery was calculated from mass spectrometry data. For permeability assay, $P_{app}$ values are reported as numbers×$10^{-07}$ cm/s. For efflux assays, the efflux ratio is calculated using $P_{app}$ (basolateral to apical) to $P_{app}$ (apical to basolateral), in addition to recovery values.

Permeability Data:

| Compound | $P_{app}$ (× $10^{-07}$ cm/s) 20 µM | Recovery (%) 20 µM |
|---|---|---|
| 24 | 377.00 | 80% |
| 6 | 377.00 | 73% |

Efflux Data:

| Compound | $P_{app}$ A to B (× $10^{-07}$ cm/s) 1 µM | Recovery A to B (%) 1 µM | $P_{app}$ B to A (× $10^{-07}$ cm/s) 1 µM | Recovery B to A (%) 1 µM | Efflux Ratio |
|---|---|---|---|---|---|
| 24 | 125.00 | 93% | 256.00 | 94% | 2.00 |
| 6 | 135.00 | 88% | 292.50 | 82.5% | 2.20 |

CYP Inhibition

The objective of this assay method was to determine the inhibitory potential of test articles, in vitro, against specific cytochrome P450 (CYP) enzymes, using human liver microsomes (HLMs). The test compounds were diluted from pure DMSO stocks to a final test concentration range of 10 µM-0.07 µM in a 0.5% DMSO solution. The compounds were co-incubated at 37° C. with 0.22 mg/mL human liver microsomes (HLMs), 50 mM phosphate buffer, 1.33 mM NADPH, 3.33 mM glucose-6-phosphate, 3.33 mM magnesium hexahydrate, 0.4 units/mL glucose-6-phosphate dehydrogenase, and appropriate concentrations of individual chemical probes for 10-30 minutes. After incubation, the samples were extracted, and protein precipitated in acetonitrile containing 0.1% formic acid. The samples were centrifuged to remove excess protein, and were analyzed by LDTD/MS/MS to determine $IC_{50}$ values. Key concentrations of substrates were as follows: CYP2D6 Substrate—Dextromethorphan at 10 µM. CYP3A4 Substrates—Testosterone at 60 µM, and Midazolam at 2 µM. Dextromethorphan and testosterone were incubated with the test compounds for 30 minutes each. Midazolam was incubated with the test compounds for 10 minutes. As shown in the Data Table below, both compounds 6 and 24 showed no CYP inhibition up to 10 µM.

Data:

| Compound | CYP inhibition mean IC$_{50}$ (INH) (µM) Isoform: CYP3A4 Substrate: testosterone | CYP inhibition mean IC$_{50}$ (INH) (µM) Isoform: CYP3A4 Substrate: midazolam | CYP inhibition mean IC$_{50}$ (INH) (µM) isoform: CYP2D6 Substrate: dextromethorphan |
|---|---|---|---|
| 24 | >10.000 | >10.000 | >10.000 |
| 6  | >10.000 | >10.000 | >10.000 |

Human, Rat, Dog, Mouse and Monkey Hepatocytes

Incubations were performed in 0.5 million hepatocytes cells/mL at 1 µM concentration of test compound in duplicate with rat, human, dog, monkey, or mouse hepatocytes, and the concentration-time course of test compound depletion was determined after withdrawing samples from the incubation at assay time points followed by liquid chromatography with tandem mass spectrometry analysis. An organic solvent was used to terminate incubations.

| Compound | Human Hepatocyte Intrinsic Clearance (µL/min/10$^7$ cells) | Rat Hepatocyte Intrinsic Clearance (µL/min/10$^7$ cells) | Mouse Hepatocyte Intrinsic Clearance (µL/min/10$^7$ cells) | Monkey Hepatocyte Intrinsic Clearance (µL/min/10$^7$ cells) | Dog Hepatocyte Intrinsic Clearance (µL/min/10$^7$ cells) |
|---|---|---|---|---|---|
| 24 | 12.7; 16.5 | 8.72 | 9.36 | >92 |  |
| 6  | 7.88; 9.49 | 9.00 | 6.63 | 27.2 |  |

Human Cytosol and S-9 Fractions

Incubations were performed in 1 mg/mL human liver cytosol with high aldehyde oxidase (AO)/xanthine oxidase (XO) activity or 2.5 mg/mL human liver S-9 fraction with high AO/XO activity at 1 µM concentration of test compound in duplicate, and the concentration-time course of test compound depletion was determined after withdrawing samples from the incubation at assay time points followed by liquid chromatography with tandem mass spectrometry analysis. An organic solvent was used to terminate incubations.

Calibration Approach for Aldehyde Oxidase Substrates

Zientek M, Jiang Y, Youdim K, Obach R S. In vitro-in vivo correlation for intrinsic clearance for drugs metabolized by human aldehyde oxidase. *Drag Metab Dispos.* 201038 (8):1322-1327. doi:10.1124/dmd.110.033555 describes a basic calibration approach for AO substrates.

This method provides a benchmarking tool for an in vitro-in vivo correlation of intrinsic clearance using commercial drugs known to be metabolized by AO.

It is known that pre-clinical species (mouse, rat and dog) cannot accurately predict AO metabolism due to their differential expression of the human AOX1 isoform of the enzyme. Mouse and rat contain the active four isoforms, AOX1, AOX2, AOX3 and AOX4, dog is lacking the active AOX1 enzyme, and only monkey contains active AOX1 isoform. Traditional allometric scaling approaches to predict human pharmacokinetics is difficult due to the lack of pre-clinical species available to accurately predict AO substrates. Therefore, an in vitro-in vivo calibration approach was undertaken using known AO substrates that have human pharmacokinetics in the clinic. Several of these drugs have failed in the clinic due to their poor PK properties. By using zaleplon (a lower clearance AO substrate) that has acceptable human pharmacokinetic properties as a benchmarking compound, a rank ordering calibration approach can be developed.

These available known AO substrates along with the test compounds were analyzed using three in vitro systems (pooled human liver cytosol, liver S-9 fractions and human hepatocytes isolated from livers perfused with HTK media). Scaled unbound intrinsic clearances were calculated for the test compounds/new chemical entities and were compared to the in vivo unbound intrinsic clearances of the known AO substrates. Compounds with AO mediated in vitro scaled unbound intrinsic clearances less than that of zaleplon are predicted to have acceptable AO in vivo clearance.

Raw Data

| Compound | Human Hepatocytes Intrinsic Clearance (µL/min/10$^6$ cells) | Human Liver Cytosol Intrinsic Clearance (µL/min/mg protein)_1 | Human Liver Cytosol Intrinsic Clearance (µL/min/mg protein)_2 | Human Liver S-9 Intrinsic Clearance (µL/min/mg protein)_1 | Human Liver S-9 Intrinsic Clearance (µL/min/mg protein)_2 |
|---|---|---|---|---|---|
| methotrexate | <2.7 | <0.7 | <0.7 | <1.1 | <1.1 |
| PF-4217903 | 4.08 | <0.7 | <0.7 | <1.1 | <1.1 |
| 5 | 7.74 | 0.7 | 1.4 | <1.1 | <1.1 |
| 4 | 7.45 | 1.2 | 2.1 | | |
| 6 | 7.88 | 1.5 | 2.2 | <1.1 | <1.1 |
| 2 | 6.36 | 1.5 | 1.7 | | |
| zaleplon | 7.53 | 3.1 | 3.4 | 2.11 | 3.32 |
| 1 | 10.3 | 3.4 | 3.3 | | |
| 24 | 12.7 | 5.1 | 5.0 | 3.06 | 2.76 |
| PF-945863 | 10.7 | 8.2 | 6.9 | 6.78 | 6.22 |
| zoniporide | 13.3 | 5.6 | 6.4 | 6.11 | 5.87 |
| O6-benzylguanine | 13.6 | 5.6 | 4.9 | 6.66 | 5.97 |
| DACA | 49.1 | 46.2 | 46.8 | 19.0 | 17.7 |
| carbazeran | 94.3 | 141 | 158 | 92.4 | 79.2 |

Scaled Data

| Compound | Estimated Free in vivo Intrinsic Clearance (Ref) | Human Liver S-9 in vitro scaled Intrinsic Clearance (ml/min/kg) | Human Liver Cytosol in vitro scaled Intrinsic Clearance (ml/min/kg) | Human Hepatocytes in vitro scaled Intrinsic Clearance (ml/min/kg) |
| --- | --- | --- | --- | --- |
| methotrexate | 0.44 | <3.4 | <1.5 | <6.9 |
| PF-4217903 | 46 | <3.4 | <1.5 | 10.4 |
| 5 | | 3.6 | 2.2 | 19.7 |
| 4 | | | 3.4 | 19.0 |
| 6 | | 3.6 | 3.9 | 20.0 |
| 2 | | | 4.3 | 16.2 |
| zaleplon | 65 | 7.1 | 6.0 | 19.2 |
| 1 | | | 6.9 | 26.2 |
| 24 | | 9.0 | 10.5 | 32.3 |
| PF-945863 | 170 | 20.1 | 15.4 | 27.2 |
| zoniporide | 180 | 18.6 | 12.4 | 33.8 |
| O6-benzylguanine | 360 | 19.5 | 10.7 | 34.6 |
| DACA | 3600 | 56.5 | 96.5 | 125 |
| carbazeran | 13000 | 263 | 307 | 234 |

Example 14

Metabolite Profiles of Compound 24 in Human Cryopreserved Hepatocytes in the Absence and Presence of the Aldehyde Oxidase Inhibitor Hydralazine The metabolite profiles of Compound 24 were investigated in vitro in human cryopreserved hepatocytes in the absence and presence of the aldehyde oxidase (AO) inhibitor hydralazine. A total of nine metabolites were identified and quantified by LC-MS following incubation of Compound 24 in human cryopreserved hepatocytes for 2 hours.

Following the incubation in human cryopreserved hepatocytes for 2 hours, 72.2% of unchanged parent remained, which was calculated based on the total integrated MS peak areas of Compound 24 and its identified metabolites. H10 was the most abundant metabolite detected and accounted for 20.3% of the total integrated MS peak areas of Compound 24 and its identified metabolites. Metabolite H4a accounted for 4.5% of the total integrated MS peak areas of Compound 24 and its identified metabolites. Each of other metabolites identified were <2% of the total integrated MS peak areas of Compound 24 and its identified metabolites.

Following the incubation in human cryopreserved hepatocytes for 2 hours in the presence of hydralazine, unchanged Compound 24 accounted for 90.9% of the total integrated MS peak areas of Compound 24 and its identified metabolites. The formation of the hydroxylated metabolite H10 was significantly inhibited and accounted for 1.6% of the total integrated MS peak areas of Compound 24 and its identified metabolites. H4a was the major metabolite and accounted for 5.4% of the total integrated MS peak areas of Compound 24 and its identified metabolites. Each of other metabolites identified were <1% of the total integrated MS peak areas of Compound 24 and its identified metabolites.

H10 was proposed to be derived from hydroxylation at the 2C position of the 3H-imidazole[4,5-b]pyridine moiety of Compound 24. H4a was proposed to be derived from hydration at the 3H-imidazole[4,5-b]pyridine moiety and glucuronide at the 2C position of the 3H-imidazole[4,5-b]pyridine moiety of Compound 24. H11a was proposed to be derived from glucuronidation of the 3H-imidazole[4,5-b]pyridine moiety of H10. H7 was proposed to be derived from the O-demethylation at 2-methoxyl-pyridine moiety of Compound 24. H6 was proposed to be glucuronide conjugate of Compound 24.

The proposed major metabolic pathways included AO-mediated hydroxylation followed by glucuronidation and a combination of hydration and glucuronidation. Other observed metabolic pathways included non-AO mediated hydroxylation followed by glucuronidation, direct glucuronidation, demethylation followed by glucuronidation, and combinations of oxidative deamination followed by oxidation.

Compound 24 was prepared in accordance with the procedure outlined in Example 1-92 of WO2017/015267.

Incubation Conditions

The general experimental design containing hydralazine is shown below:

| Reagent or Parameters | Final Concentration/Conditions |
| --- | --- |
| Compound 24 | 1 µM |
| Cryopreserved monkey hepatocytes | 0.5 × 10$^6$ cells/mL |
| Cryopreserved human hepatocytes | 1 × 10$^6$ cells/mL |
| Incubation time | 0, 15, 30, 60, 90, and 120 min |
| Hydralazine HCl | 10 µM |
| Incubation | 37° C. in CO$_2$ incubator |
| Incubation medium | KHB buffer |
| Total incubation volume | 0.5 mL |

After study sampling, the remaining samples from triplicate incubations were combined and processed for the metabolite identification study.

Sample Preparation

To each sample was added equal amounts of ice-cold acetonitrile (v/v) and the samples were then vortex mixed. Following centrifugation at approximately 13,000 rpm for 10 minutes, the supernatants were concentrated under nitrogen flow at 35° C. until approximately 0.1-0.2 mL of extract remained. Prior to analysis, the remaining extract was centrifuged at approximately 13,000 rpm for 15 minutes. The supernatant was injected into LC/UV/MS for analysis.

Instrument Conditions

Metabolite identification was performed on UPLC (Thermo Vanquish) coupled with UV (Thermo Vanquish) and mass spectrometry (MS) detection (Thermo Orbitrap ID-X).

| HPLC | |
|---|---|
| Column | Kinetex $C_{18}$, 1.7 μm, 100 Å, 100 × 2.1 mm |
| Mobile Phase | A: 10 mM ammonium acetate in water, pH 5 adjusted with formic acid |
| | B: Acetonitrile |
| Flow Rate | 0.30 mL/min |
| Column Temperature | 35° C. p |
| Gradient | |

| Time (min) | % A | % B |
|---|---|---|
| 0.0 | 95 | 5 |
| 3.0 | 95 | 5 |
| 23 | 55 | 45 |
| 24 | 5 | 95 |
| 28 | 5 | 95 |
| 28.1 | 95 | 5 |
| 32.0 | 95 | 5 |

| PDA | |
|---|---|
| UV Wavelength | 280 nm |

| MS | |
|---|---|
| Ion Mode | ESI positive |
| FTMS | Resolution = 12000 |

Data Evaluation

The mass peak areas were used for metabolite profiling, due to low sample concentrations. The percentage of metabolite or unchanged parent was calculated based on the total integrated MS peak areas of Compound 24 and its identified metabolites on the assumption of equal mass spectral response for equivalent molar concentration of the metabolites or parent compound. Metabolites having a peak area that accounts for equal to or more than 0.1% of the toral integrated MS peaks areas are reported in Table 1 below.

The metabolites are characterized based on their accurate masses (tolerance ≤5 ppm), mass fragmentation patterns, and comparison with other in vitro studies.

Figure 12A:
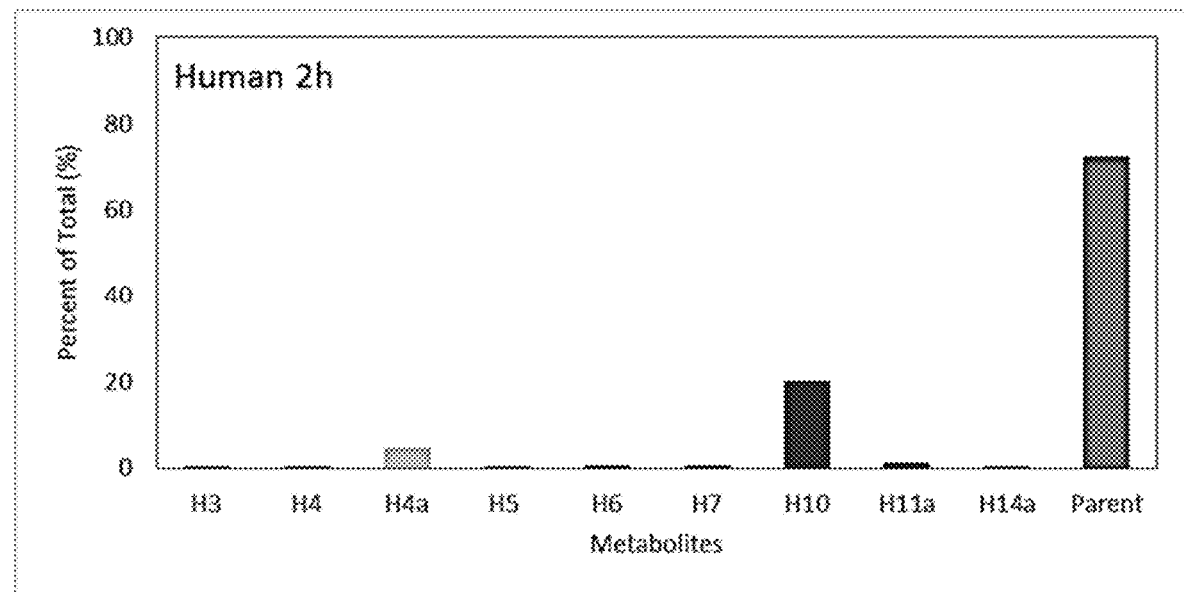
FIG. 12A shows an in vitro metabolic profile of Compound 24 following incubation in human cryopreserved hepatocytes in the absence of AO inhibitor hydralazine.
Figure 12B:
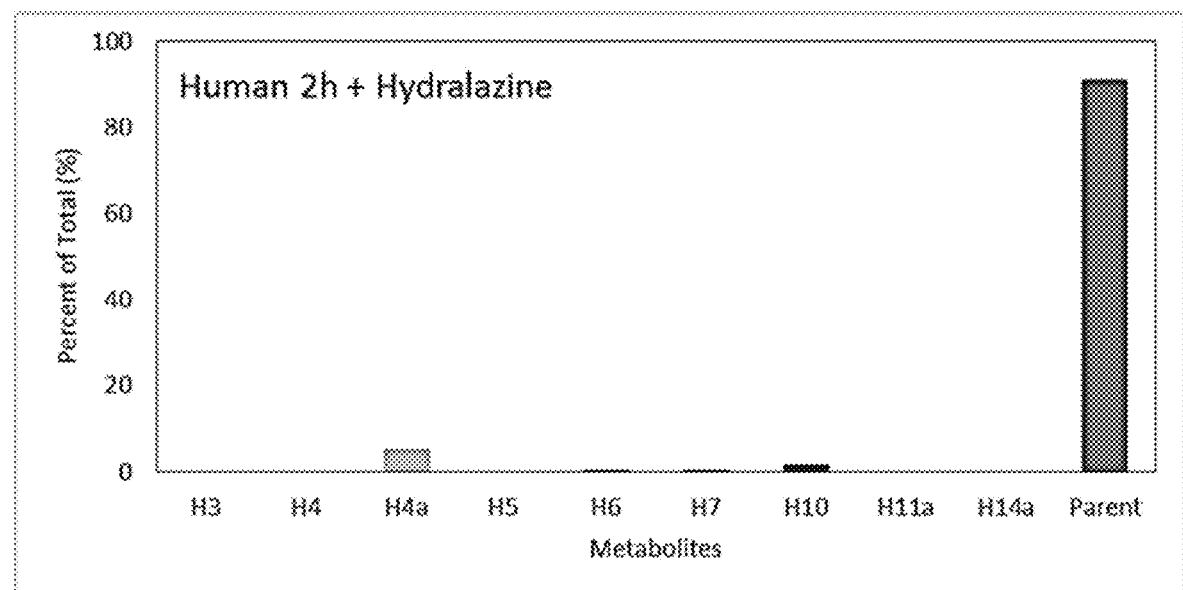
FIG. 12B shows an in vitro metabolic profile of Compound 24 following incubation in human cryopreserved hepatocytes in the presence of AO inhibitor hydralazine.

The metabolite profiles of Compound 24 were investigated in vitro in human cryopreserved hepatocytes in the absence and presence of AO inhibitor hydralazine. A total of nine metabolites were identified and quantified by LC-MS following incubation of Compound 24 in human cryopreserved hepatocytes for 2 hours. (See FIGS. 12A-12B)

Following the incubation in human cryopreserved hepatocytes for 2 hours, 72.2% of unchanged parent remained, which was calculated based on the total integrated MS peak areas of Compound 24 and its identified metabolites. H10 was the most abundant metabolite detected and accounted for 20.3% of the total integrated MS peak areas of Compound 24 and its identified metabolites. Metabolite H4a accounted for 4.5% of the total integrated MS peak areas of Compound 24 and its identified metabolites. Each of other metabolites identified were <2% of the total integrated MS peak areas of Compound 24 and its identified metabolites.

Following the incubation in human cryopreserved hepatocytes for 2 hours in the presence of AO inhibitor, hydralazine, unchanged Compound 24 accounted for 90.9% of the total integrated MS peak areas of Compound 24 and its identified metabolites. The formation of the hydroxylated metabolite H10 was significantly inhibited and accounted for 1.6% of the total integrated MS peak areas of Compound 24 and its identified metabolites. H4a was the major metabolite and accounted for 5.4% of the total integrated MS peak areas of Compound 24 and its identified metabolites. Each of other metabolites identified were <1% of the total integrated MS peak areas of Compound 24 and its identified metabolites.

H10 was proposed to be derived from hydroxylation at 2C position of 3H-imidazole[4,5-b]pyridine moiety of Compound 24. H4a was proposed to be derived from hydration at 3H-imidazole[4,5-b]pyridine moiety and glucuronide at 2C position of 3H-imidazole[4,5-b]pyridine moiety of Compound 24. H11a was proposed to be derived from glucuronidation of 3H-imidazole[4,5-b]pyridine moiety of H10. H7 was proposed to be derived from O—demethylation at

TABLE 1

Metabolite profiles of Compound 24 following incubation in human cryopreserved hepatocytes for 2 hours in the absence and presence of hydralazine

| Peak ID | Retention time in UV (min) | Formula Change (M = $C_{23}H_{22}N_4O_4$) | Theo. m/z (M + H)$^+$ | Human Hepatocytes Mass Peak Area | Human Hepatocytes % of Total | Human Hepatocytes + Hydralazine Mass Peak Area | Human Hepatocytes + Hydralazine % of Total |
|---|---|---|---|---|---|---|---|
| Parent | 21.50 | — | 419.1714 | 8.75E+07 | 72.2 | 1.32E+08 | 90.9 |
| H4 (P11) | 13.69 | [M − CH$_2$ + C$_6$H$_8$O$_6$] | 581.1878 | 1.57E+05 | 0.1 | 1.96E+05 | 0.1 |
| H4a | 14.07 | [M + O + 2H + C$_6$H$_8$O$_6$] | 613.2141 | 5.41E+06 | 4.5 | 7.79E+06 | 5.4 |
| H5 (P13a) | 14.40 | [M + O + C$_6$H$_8$O$_6$] | 611.1984 | 2.95E+05 | 0.2 | 3.77E+05 | 0.3 |
| H7 (P17) | 14.43 | [M − CH$_2$] | 405.1557 | 8.11E+05 | 0.7 | 9.24E+05 | 0.6 |
| H6 (P16a) | 14.59 | [M + C$_6$H$_8$O$_6$] | 595.2035 | 6.56E+05 | 0.5 | 9.12E+05 | 0.6 |
| H11a (P15b) | 14.83 | [M + O + C$_6$H$_8$O$_6$] | 611.1984 | 1.47E+06 | 1.2 | 1.44E+05 | 0.1 |
| H3 (P20a) | 15.81 | [M − C$_6$H$_5$N$_3$ + 2O] | 332.1129 | 1.14E+05 | <0.1 | 2.02E+05 | 0.1 |
| H14a | 19.22 | [M + O] | 435.1663 | 2.07E+05 | 0.2 | 2.91E+05 | 0.2 |
| H10 (P27) | 20.61 | [M + O] | 435.1663 | 2.46E+07 | 20.3 | 2.30E+06 | 1.6 |
| Total | | | | 1.21E+08 | 100.0 | 1.45E+08 | 100.0 |

2-methoxyl-pyrindine moiety of Compound 24. H6 was proposed to be glucuronide conjugate of Compound 24.

Figure 13:
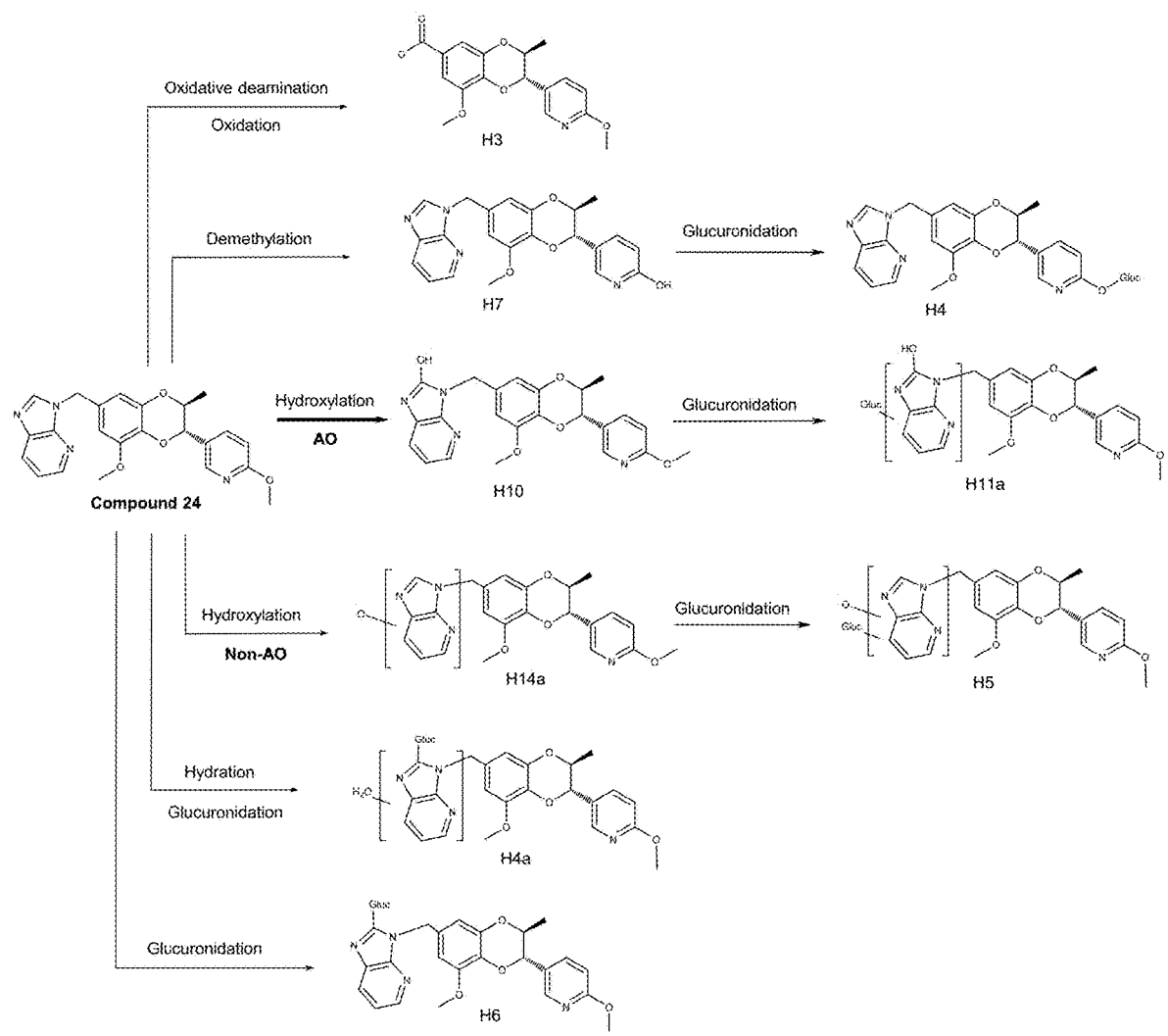
FIG. 13 shows proposed metabolic pathways of Compound 24 in cryopreserved human hepatocytes in the absence and presence of AO inhibitor hydralazine.

The proposed major metabolic pathways (FIG. 13) include AO-mediated hydroxylation followed by glucuronidation and combination of hydration and glucuronidation. Other observed metabolic pathways included non-AO mediated hydroxylation followed by glucuronidation, direct glucuronidation, demethylation followed by glucuronidation, and combination of oxidative deamination followed by oxidation.

Example 15

Metabolite Profiles of Compound 6 in Human Cryopreserved Hepatocytes in the Absence and Presence of Aldehyde Oxidase Inhibitor Hydralazine The metabolite profiles of Compound 6 were investigated in vitro in human cryopreserved hepatocytes in the absence and presence of aldehyde oxidase (AO) inhibitor hydralazine. A total of nine metabolites were identified and quantified by LC-MS following incubation of Compound 6 in human cryopreserved hepatocytes for 2 hours.

Following the incubation in human cryopreserved hepatocytes for 2 hours, 87.1% of unchanged parent remained, which was calculated based on the total integrated MS peak areas of Compound 6 and its identified metabolites. H10 and H4a were the major metabolites detected and accounted for 6.6% and 4.6% of the total integrated MS peak areas of Compound 6 and its identified metabolites, respectively. Each of other metabolites identified were <1% of the total integrated MS peak areas of Compound 6 and its identified metabolites.

Following the incubation in human cryopreserved hepatocytes for 2 hours in the presence of AO inhibitor, hydralazine, unchanged Compound 6 accounted for 92.0% of the total integrated MS peak areas of Compound 6 and its identified metabolites. The formation of the hydroxylated metabolite H10 was significantly inhibited and accounted for 0.9% of the total integrated MS peak areas of Compound 6 and its identified metabolites. H4a was the major metabolite and accounted for 5.7% of the total integrated MS peak areas of Compound 6 and its identified metabolites. Each of other metabolites identified were <1% of the total integrated MS peak areas of Compound 6 and its identified metabolites.

H10 was proposed to be derived from hydroxylation at the 2C position of the 3H-imidazole[4,5-b]pyridine moiety of Compound 6. H4a was proposed to be derived from hydration at the 3H-imidazole[4,5-b]pyridine moiety and glucuronide at the 2C position of the 3H-imidazole[4,5-b]pyridine moiety of Compound 6. H11a was proposed to be derived from glucuronidation of the 3H-imidazole[4,5-b]pyridine moiety of H10. H7 was proposed to be derived from O—demethylation at the 2-methoxyl-pyrindine moiety of Compound 6. H6 was proposed to be a glucuronide conjugate of Compound 6.

The proposed major metabolic pathways included AO-mediated hydroxylation followed by glucuronidation and a combination of hydration and glucuronidation. Other observed metabolic pathways included non-AO mediated hydroxylation followed by glucuronidation, direct glucuronidation, demethylation followed by glucuronidation, and combinations of oxidative deamination followed by oxidation.

Incubation Conditions

The general experimental design containing hydralazine is shown below:

| Reagent or Parameters | Final Concentration/Conditions |
|---|---|
| Compound 6 | 1 μM |
| Cryopreserved human hepatocytes | 1 × 10$^6$ cells/mL |
| Incubation time | 0, 15, 30, 60, 90, and 120 min |
| Hydralazine HCl | 10 μM |
| Incubation | 37° C. in $CO_2$ incubator |
| Incubation medium | KHB buffer |
| Total incubation volume | 0.5 mL |

After study sampling, the remaining samples from triplicate incubations were combined and processed for metabolite identification study.

Sample Preparation

To each sample was added equal amounts of ice-cold acetonitrile (v/v) and the samples were vortex mixed. Following centrifugation at approximately 13,000 rpm for 10 minutes, the supernatants was concentrated under nitrogen flow at 35° C. until approximately 0.1-0.2 mL of extract remained. Prior to analysis, the remaining extract was centrifuged at approximately 13,000 rpm for 15 minutes. The supernatant was injected into LC/UV/MS for analysis.

Instrument Conditions

Metabolite identification was performed on UPLC (Thermo Vanquish) coupled with UV (Thermo Vanquish) and mass spectrometry (MS) detection (Thermo Orbitrap ID-X).

| HPLC | | |
|---|---|---|
| Column | Kinetex $C_{18}$, 1.7 μm, 100 Å, 100 × 2.1 mm | |
| Mobile Phase | A: 10 mM ammonium acetate in water, pH 5 adjusted with formic acid | |
| | B: Acetonitrile | |
| Flow Rate | 0.30 mL/min | |
| Column Temperature | 35° C. | |
| Gradient | Time (min) | % A | % B |
| | 0.0 | 95 | 5 |
| | 3.0 | 95 | 5 |
| | 23 | 55 | 45 |
| | 24 | 5 | 95 |
| | 28 | 5 | 95 |
| | 28.1 | 95 | 5 |
| | 32.0 | 95 | 5 |
| PDA | | |
| UV Wavelength | 280 nm | |
| MS | | |
| Ion Mode | ESI positive | |
| FTMS | Resolution = 12000 | |

Data Evaluation

The mass peak areas are used for metabolite profiling, due to low sample concentrations. The percentage of metabolite or unchanged parent was calculated based on the total integrated MS peak areas of Compound 6 and its identified metabolites on the assumption of equal mass spectral response for equivalent molar concentration of the metabolites or parent compound. Metabolites having a peak area that accounts for equal to or more than 0.1% of the toral integrated MS peaks areas are reported in Table 2 below.

The metabolites are characterized based on their accurate masses (tolerance≤5 ppm), mass fragmentation patterns, and comparison with other in vitro studies.

Results

TABLE 2

Metabolite profiles of Compound 6 following incubation in human cryopreserved hepatocytes for 2 hours in the absence and presence of hydralazine

| Peak ID | Retention time in UV (min) | Formula Change (M = $C_{23}H_{21}DN_4O_4$) | Theo. m/z $(M + H)^+$ | Human Hepatocytes | | Human Hepatocytes + Hydralazine | |
|---|---|---|---|---|---|---|---|
| | | | | Mass Peak Area | % of Total | Mass Peak Area | % of Total |
| Parent | 21.49 | — | 420.1777 | 2.13E+07 | 87.1 | 6.50E+07 | 92.0 |
| H4 (P11) | 13.68 | $[M - CH_2 + C_6H_8O_6]$ | 582.1941 | 2.38E+04 | 0.1 | 7.32E+04 | 0.1 |
| H4a | 14.08 | $[M - D + O + 2H + C_6H_8O_6]$ | 613.2141 | 1.12E+06 | 4.6 | 4.01E+06 | 5.7 |
| H5 (P13a) | 14.37 | $[M + O + C_6H_8O_6]$ | 612.2047 | 4.11E+04 | 0.2 | 1.54E+05 | 0.2 |
| H7 (P17) | 14.43 | $[M - CH_2]$ | 406.1620 | 1.14E+05 | 0.5 | 3.54E+05 | 0.5 |
| H6 (P16a) | 14.58 | $[M - D + C_6H_8O_6]$ | 595.2035 | 1.03E+05 | 0.4 | 2.32E+05 | 0.3 |
| H11a (P15b) | 14.83 | $[M - D + O + C_6H_8O_6]$ | 611.1984 | 6.20E+04 | 0.3 | 3.27E+04 | <0.1 |
| H3 (P20a) | 15.83 | $[M - C_6H_5DN_3 + 2O]$ | 332.1129 | 5.18E+04 | 0.2 | 8.90E+04 | 0.1 |
| H14a | 19.20 | $[M + O]$ | 436.1726 | 1.48E+04 | <0.1 | 9.01E+04 | 0.1 |
| H10 (P27) | 20.61 | $[M - D + O]$ | 435.1663 | 1.62E+06 | 6.6 | 6.10E+05 | 0.9 |
| Total | | | | 2.44E+07 | 100.0 | 7.06E+07 | 100.0 |

Figure 14A:
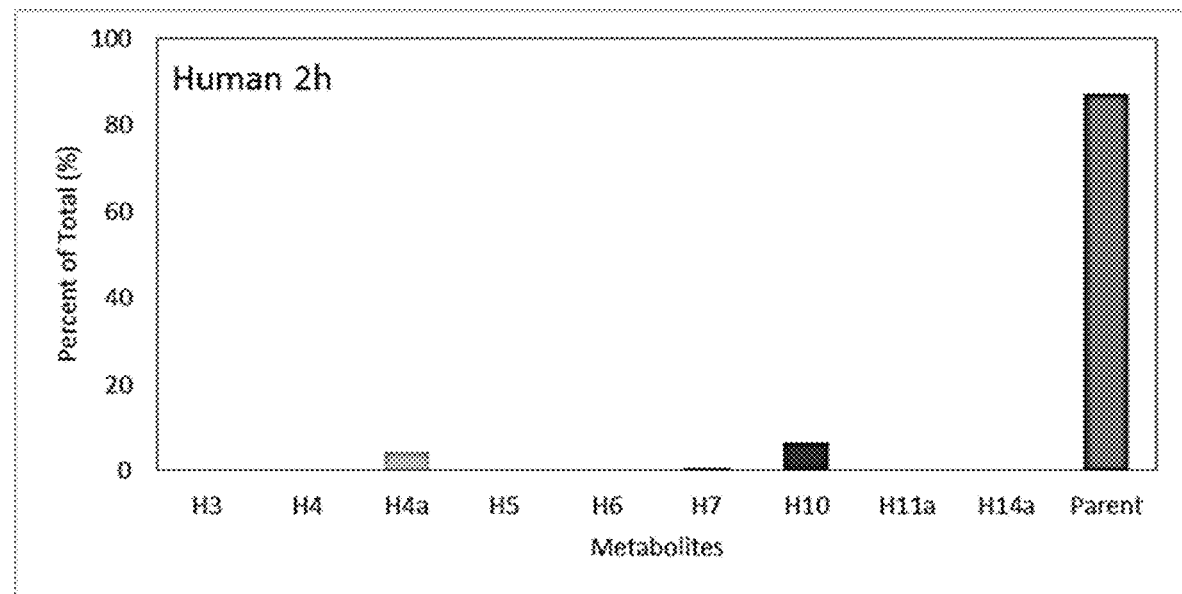
FIG. 14A shows an in vitro metabolic profile of Compound 6 following incubation in human cryopreserved hepatocytes in the absence of AO inhibitor hydralazine.
Figure 14B:
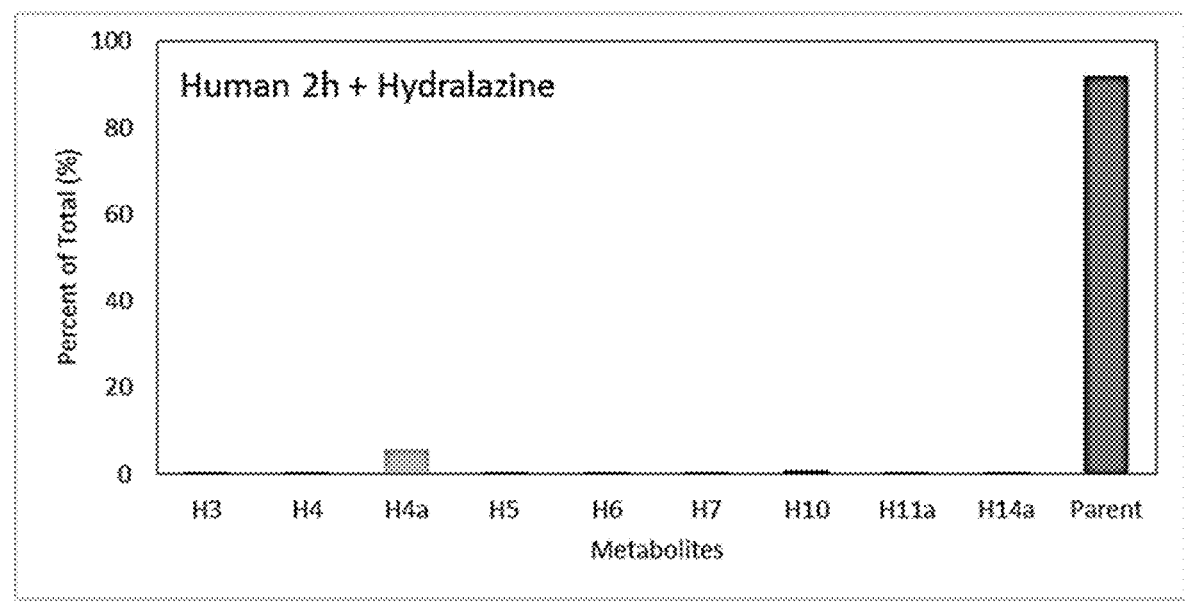
FIG. 14B shows an in vitro metabolic profile of Compound 6 following incubation in human cryopreserved hepatocytes in the presence of AO inhibitor hydralazine.

The metabolite profiles of Compound 6 were investigated in vitro in human cryopreserved hepatocytes in the absence and presence of AO inhibitor hydralazine. A total of nine metabolites were identified and quantified by LC-MS following incubation of Compound 6 in human cryopreserved hepatocytes for 2 hours. (See FIG. 14A-14B)

Following the incubation in human cryopreserved hepatocytes for 2 hours, 87.1% of unchanged parent remained, which was calculated based on the total integrated MS peak areas of Compound 6 and its identified metabolites. H10 and H4a were the major metabolites detected and accounted for 6.6% and 4.6% of the total integrated MS peak areas of Compound 6 and its identified metabolites, respectively. Each of other metabolites identified were <1% of the total integrated MS peak areas of Compound 6 and its identified metabolites.

Following the incubation in human cryopreserved hepatocytes for 2 hours in the presence of AO inhibitor, hydralazine, unchanged Compound 6 accounted for 92.0% of the total integrated MS peak areas of Compound 6 and its identified metabolites. The formation of the hydroxylated metabolite H10 was significantly inhibited and accounted for 0.9% of the total integrated MS peak areas of Compound 6 and its identified metabolites. H4a was the major metabolite and accounted for 5.7% of the total integrated MS peak areas of Compound 6 and its identified metabolites. Each of other metabolites identified were <1% of the total integrated MS peak areas of Compound 6 and its identified metabolites.

Figure 15:
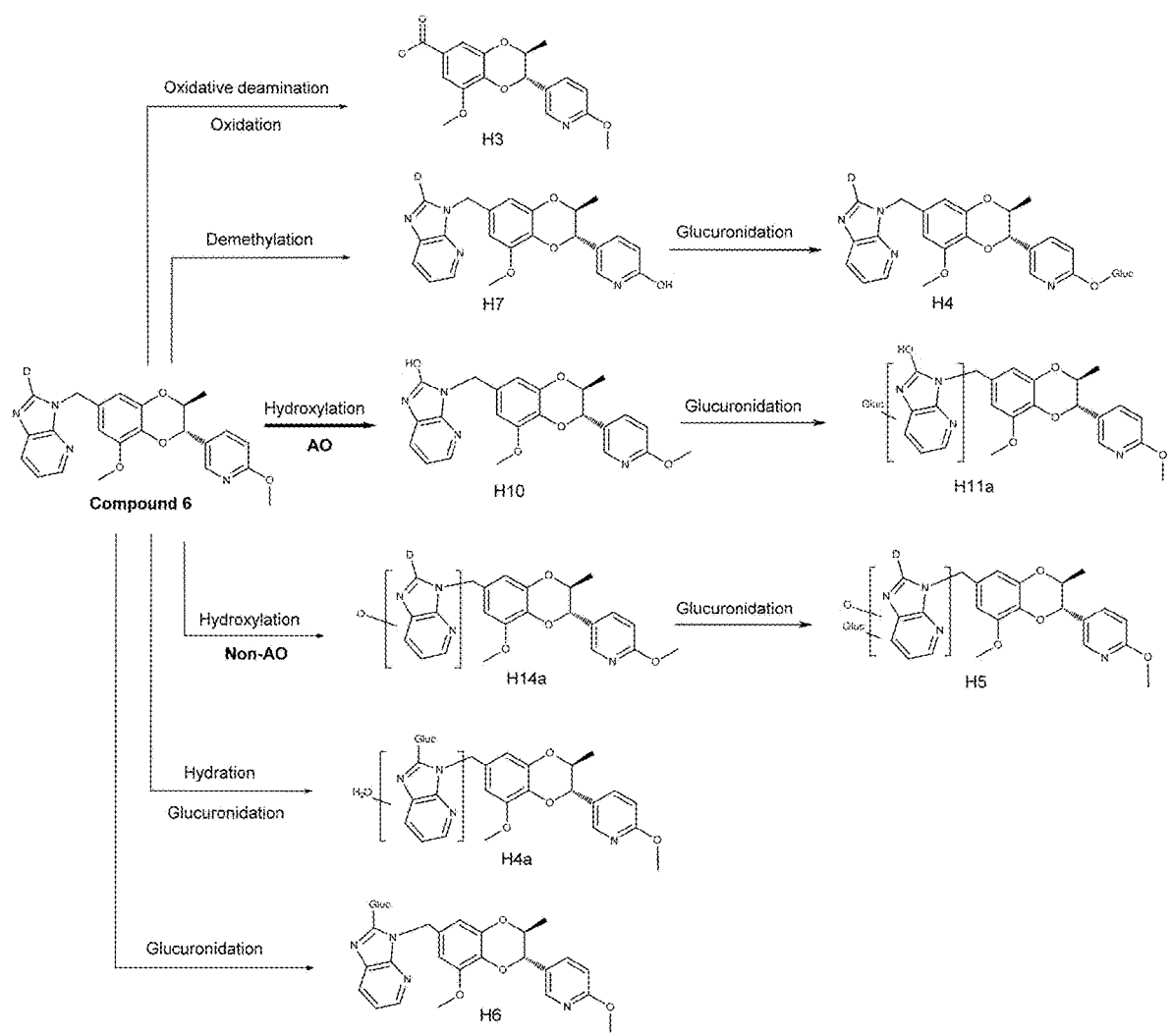
FIG. 15 shows proposed metabolic pathways of Compound 6 in cryopreserved human hepatocytes in the absence and presence of AO inhibitor hydralazine.

H10 was proposed to be derived from hydroxylation at the 2C position of the 3H-imidazole[4,5-b]pyridine moiety of Compound 6. H4a was proposed to be derived from hydration at the 3H-imidazole[4,5-b]pyridine moiety and glucuronide at the 2C position of the 3H-imidazole[4,5-b]pyridine moiety of Compound 6. H11a was proposed to be derived from glucuronidation of the 3H-imidazole[4,5-b]pyridine moiety of H10. H7 was proposed to be derived from O—demethylation at the 2-methoxyl-pyridine moiety of Compound 6. H6 was proposed to be a glucuronide conjugate of Compound 6. The proposed major metabolic pathways (FIG. 15) include AO-mediated hydroxylation followed by glucuronidation and a combination of hydration and glucuronidation. Other observed metabolic pathways included non-AO mediated hydroxylation followed by glucuronidation, direct glucuronidation, demethylation followed by glucuronidation, and combinations of oxidative deamination followed by oxidation.

Example 16

In Vitro Microglia Stimulation Study

To determine the impact of on human microglial cytokine/chemokine production following $CSF_1$ stimulation, the following experiments were conducted.

Test Articles:
DMSO
Compound 6—Diluted stock solution (10 mM) with culture media to get a 100 µM working solution and treated microglia at 1.5625 nM, 3.125 nM, 6.25 nM, 12.5 nM, 25 nM, 50 nM, 100 nM, or 200 nM.
Compound 24—Diluted stock solution (10 mM) with culture media to get a 100 µM working solution and treated microglia at 1.5625 nM, 3.125 nM, 6.25 nM, 12.5 nM, 25 nM, 50 nM, 100 nM, or 200 nM.
Recombinant Human $CSF_1$ (R&D Systems, cat #216-ML/CF, lot #MVN1218101)—Prepared 100 µg/mL stock solution by dissolving 50 µg in 500 µl PBS and treated microglia with 100 ng/mL.

Methods
Treatment and Stimulation of iCell Microglia
iCell microglia (human iPSC derived microglia) were acquired from FujiFilm (cat #C1110, lot #105458). These cells were thawed and maintained in iCell Microglia Complete Media according the manufacture instructions. For this assay, iCell microglia were resuspended at a concentration of $5 \times 10^5$ cells/mL and 100 µL of this cell suspension was added to the inner 60 wells of a 96-well plate. iCell microglia were allowed to rest overnight at 37° C., 5% $CO_2$. The following evening, the media was removed and replaced with Neurobasal Media (Gibco, cat #21103049) containing B27 supplement (Gibco, cat #17504044). Again, cells were allowed to rest overnight at 37° C., 5% $CO_2$. The following morning, cells were treated with either dimethyl sulfoxide (DMSO) or Compound 6 or Compound 24 for 30 minutes at 37° C., 5% $CO_2$. Cells were then stimulated with 100 ng/mL recombinant human $CSF_1$ for 24 hours. After stimulation, the culture supernatant was removed from each well and aliquoted into two different 96-well plates for subsequent ELISA assays.

CellTiter Glo 2.0 Viability Assay

Cell viability was determined using the CellTiter Glo 2.0 Luminescent Cell Viability Assay (Promega, cat #G9242). The assay reagent was first allowed to equilibrate to room temperature for 30 minutes. After culture supernatants were removed, 100 µL fresh room temperature media was added to each well. Subsequently, 100 µL of assay reagent was added to each well. The assay plate was then shaken for two minutes and left to rest for 10 minutes. 100 µL was transferred from each well to a white plate and luminescence was read immediately on the FlexStation3 Multi-Mode Microplate Reader (Molecular Devices, cat #Flex3) with SoftMax Pro Software.

Mouse MCP-1 ELISA

Culture supernatants were assayed with the Quantikine Human MCP-1 ELISA kit (R&D Systems, cat #SCP00). Samples were diluted 1:10 with Calibrator Diluent. Two hundred microliters of Standards and diluted Sample were then added to the wells. The plate was mixed by gently tapping the frame and sealed with an adhesive strip. The plate incubated for 2 hours at room temperature. After incubation, the plate was washed with approximately 400 µL of Wash Buffer using a squirt bottle 5 times. After the last wash, the plate was gently tapped on paper towels to remove excess moisture. Two hundred microliters of human MCP-1 conjugate was added to each well, covered with a new strip of adhesive tape, and incubated at room temperature for 2 hours. After incubation, the plate was washed as described above. Two hundred microliters of Substrate Solution was then added to each well and incubated for 30 minutes at room temperature in the dark. After incubation, fifty microliters of the acid stop solution was added to each well, and the plate was read on the FlexStation3 Multi-Mode Microplate Reader (Molecular Devices, cat #Flex3) with SoftMax Pro Software at 450 nm.

Results iCell microglia (human iPSC derived microglia) were plated at 50,000 cells per well and rested overnight. Media containing growth factors was removed and then the cells were allowed to rest overnight again. Next, cells were pre-treated with DMSO or Compound 6 or Compound 24 for 30 minutes, and then subjected to $CSF_1$ stimulation. Cell viability was assessed utilizing Promega's Cell Titer Glo Assay Kit. Cell culture supernatants from this experiment were processed in a MCP1 ELISA to determine whether stimulation/treatment impacted chemokine production.

Figure 16:
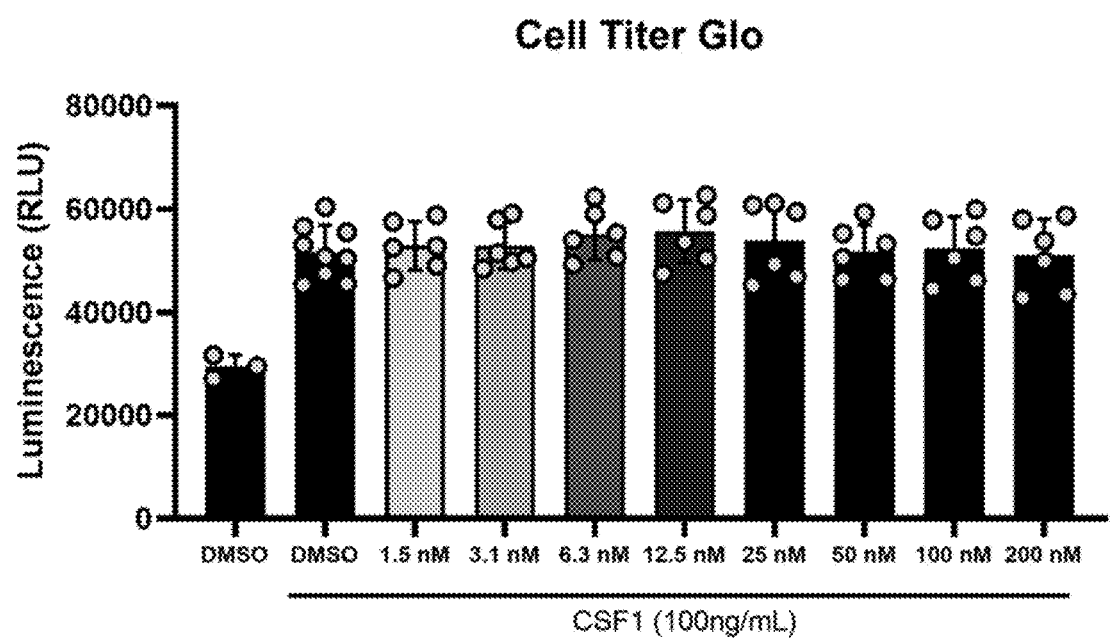
FIG. 16 shows cell viability following $CSF_1R$ inhibitor treatment and $CSF_1$ stimulation.

Compound 6 did not impact human microglia viability at the concentrations assessed in this experiment (FIG. 16). FIG. 16 depicts cell viability following $CSF_1R$ inhibitor treatment and $CSF_1$ stimulation as described above. iCell human microglia were plated at 50,000 cells/well and rested overnight following growth factor starvation. Cells were pre-treated with DMSO or RA16100017 for 30 minutes and then subjected to $CSF_1$ stimulation. Cell viability was assessed after 24 hours utilizing Promega's Cell Titer Glo 2.0 Assay Kit. $CSF_1$ stimulation induced an increase in cell viability and the $CSF_1R$ inhibitor had no impact on this effect. Each data point represents a single well while graphical columns represent the mean and standard deviation of six wells.

Figure 17:
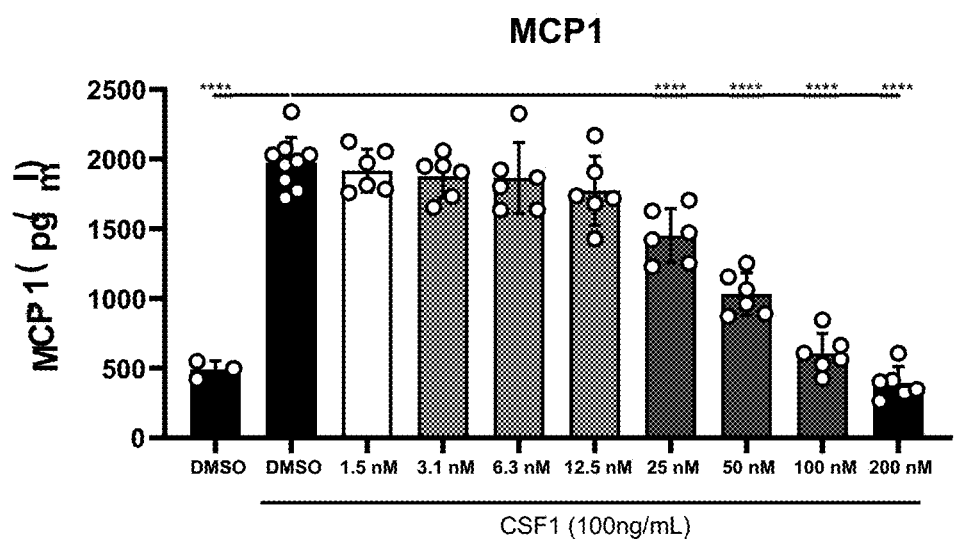
FIG. 17 shows the blocking effect of Compound 6 on $CSF_1$-induced MCP-1 production in this experiment.

As seen in FIG. 17, $CSF_1$ stimulation induced a significant increase in the release of MCP-1 (CCL2—chemokine). FIG. 17 shows the blocking effect of Compound 6 on $CSF_1$-induced MCP-1 production in this experiment. iCell human microglia were plated at 50,000 cells/well and rested overnight following growth factor starvation. Cells were pre-treated with DMSO or RA16100017 for 30 minutes and then subjected to $CSF_1$ stimulation. MCP-1 secretion was assessed after 24 hours utilizing R&D MCP1 Elisa Kit. The $CSF_1R$ inhibitor treatment significantly reduced MCP1 production in a concentration dependent manner (Ordinary one-way ANOVA). Each data point represents a single well while graphical columns represent the mean and standard deviation of six wells.

Figure 18A:
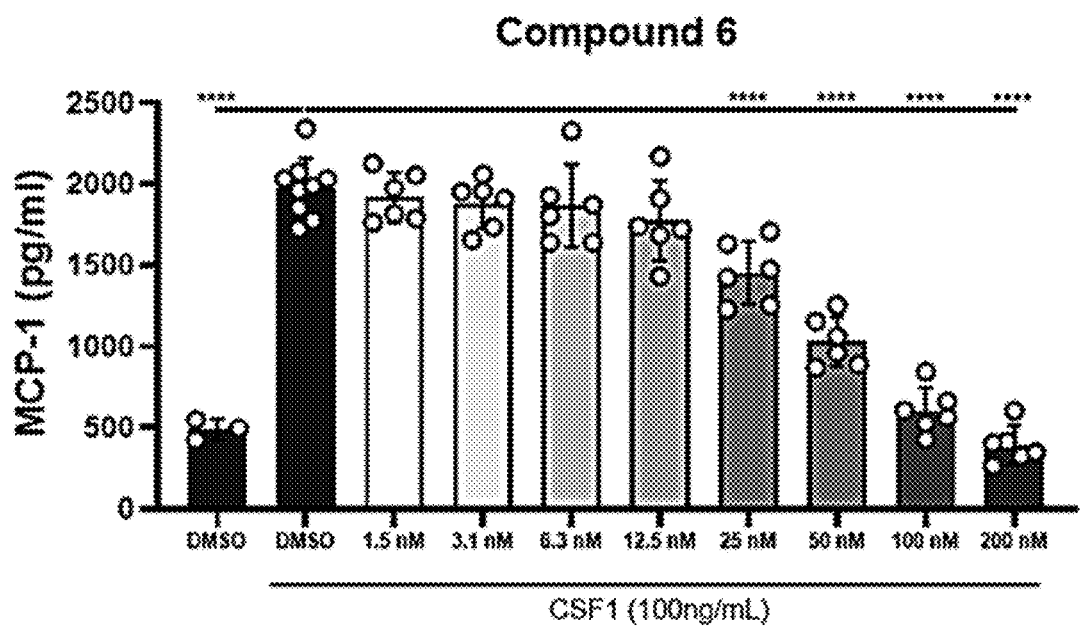
FIGS. 18A-18B compares MCP1 production of Compound 6 (FIG. 18A) with Compound 24 (FIG. 18B), showing similar effect on MCP1.
Figure 18B:
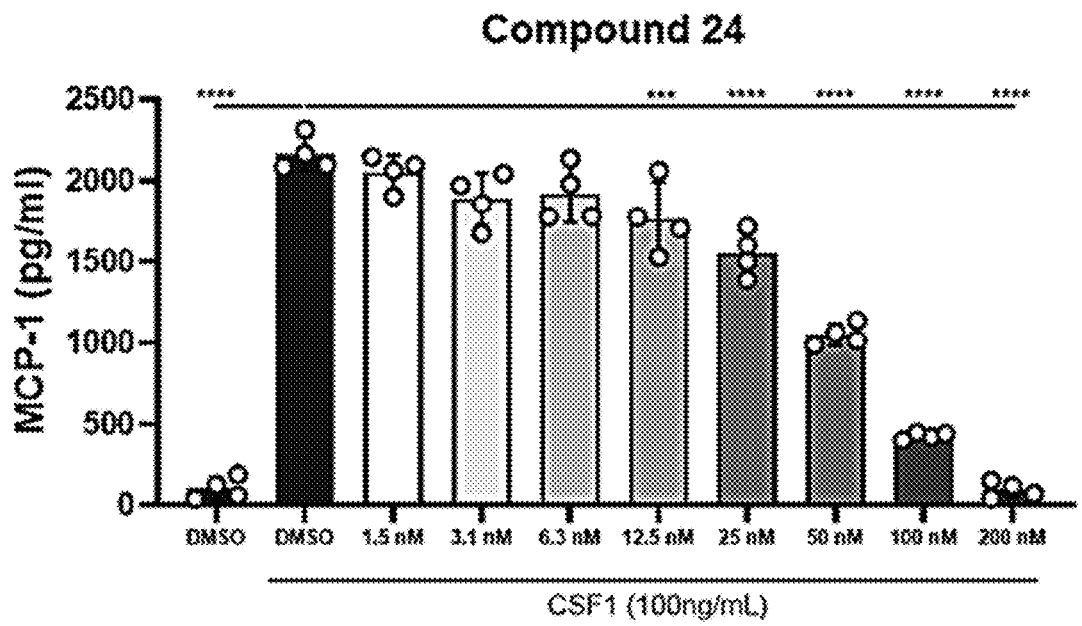

Compound 6 significantly reduced MCP1 production in a concentration dependent manner (Ordinary one-way ANOVA, $p<0.0001$). $CSF_1$ stimulation induced a significant increase in MCP1 production, and $CSF_1R$ inhibition with Compound 6 abrogated this effect in a concentration-dependent manner. FIG. 18 compares MCP1 production of Compound 6 with Compound 24, showing similar effect on MCP1.

Example 17

MOG-EAE

Experimental autoimmune encephalomyelitis (EAE) is primarily used as a non-clinical model of autoimmune inflammatory diseases of the CNS, and resembles many aspects of human multiple sclerosis. The myelin oligodendrocyte glycoprotein (MOG)-induced EAE model is ideal for exploring this immune-mediated mechanism of neuroinflammation and demyelination. In the following experiment, Compound 24 and Compound 6 were tested to evaluate possible efficacy in reducing disease scores in the mouse c57BL/6 EAE model.

Species: Female C57BL/6J 8-9 Weeks Old

| Grp # | Disease Induction | Treatment | Animals per group | Comments |
|---|---|---|---|---|
| 1 | MOG + CFA + PTX | Vehicle | 28 | Treatment p.o. BID for 7 days |
| 2 | MOG + CFA + PTX | 15 mg/kg Compound 24 | 29 | Treatment p.o. BID for 7 days |
| 3 | MOG + CFA + PTX | 15 mg/kg Compound 6 | 12 | Treatment p.o. BID for 7 days |

Test articles:
$MOG_{35-55}$ peptide (New England Peptides, lot #BU01787)—250 µg/mouse in 4 mg/mL complete Freund's adjuvant (CFA; Chondrex Inc, Cat #7009, lot #190446) *Bordetella pertussis* toxin (PTX, Sigma, cat #P7208-5OUG, lot #MKCL 1350)—280 ng/mouse in 200 µL PBS CSF-1R inhibitors—15 mg/kg
Vehicle—0.5% methylcellulose/0.2% Tween-80
Delivery:
  MOG peptide & CFA: subcutaneous injection to 2 sites in the hind flank (100 μL/site).
  *Bordetella pertussis* toxin: i.v. injection of 280 ng/mouse in 200 μL PBS on Day 0 and 2.
  CSF₁R inhibitor: oral gavage every 12 hours
  Vehicle: oral gavage every 12 hours
Time points:
  Day 0—Administer MOG peptide in CFA and PTX to Groups 1-3
  Day 2—Administer PTX by i.v. to Groups 1-3
  Day 9—Begin daily scoring of mice
  Day 11-14—Randomize mice to groups when reach score of 1 and begin treatment
  Day ~18-21—After 7 days of treatment, perfuse mice and euthanize animals.

Mice were clinically assessed daily for signs of paralytic disease and weighed intermittently to document weight loss. At study termination, ½ brain was fixed for histology and brain/liver/plasma were collected for exposure. Spinal cord and whole blood was collected for flow cytometry. Additional plasma aliquots were saved for follow up analysis.

Methods:

EAE Induction and Scoring

Female C57BL/6J mice were immunized with an emulsion of MOG$_{35-55}$ peptide (250 μg/mouse) in complete Freund's adjuvant (CFA). The emulsion was delivered by two subcutaneous injections to the hind flank in a volume of 100 μL per injection site. *Bordetella pertussis* toxin (PTX) was administered via tail vein injection on Day 0 and Day 2 at a dose of 280 ng/animal in 200 μL of PBS. Following EAE induction, the mice were monitored daily for paralytic symptoms and scored for their clinical presentation using a progressive scoring system (Score 0: no disease; Score 1: flaccid tail; Score 2: hindlimb weakness; Score 3: hindlimb paralysis; Score 4: Front limb weakness or partial paralysis; Score 5: death).

Animals were enrolled into the study as soon as they reached a disease score of 1. Each day, animals achieving a score of one for the first time were equally distributed across the treatment groups and treatment was initiated that evening. The vehicle and compound were color coded so that personnel scoring the study were blinded to treatment group. Animals were treated for seven days. One hour after the final dose (14 doses total, 7 days of treatment), animals were anesthetized, and blood was collected into an EDTA tube via retro-orbital bleed. Animals were then perfused with ice cold PBS and the appropriate tissue was collected for study endpoints.

Results

Figure 19A:
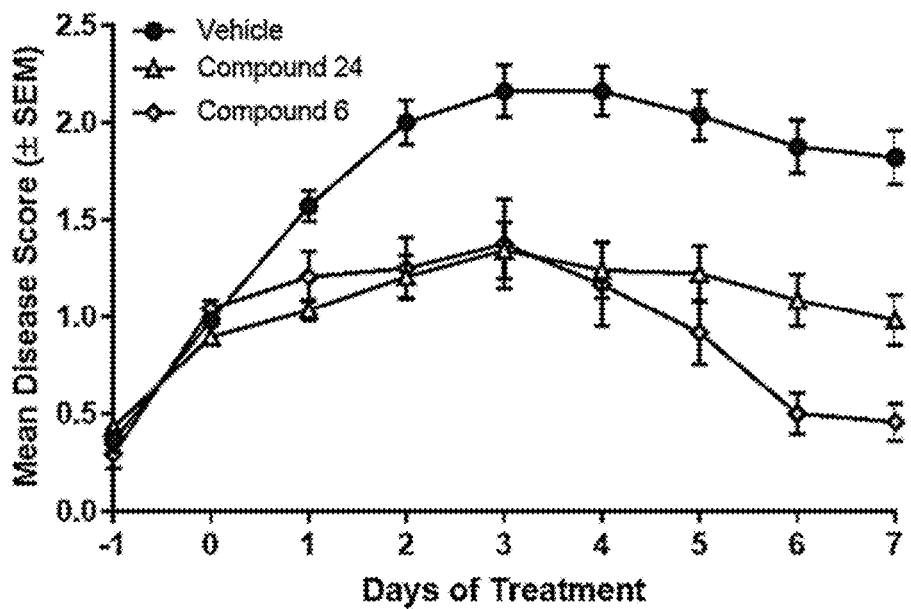
FIGS. 19A-19B show that both $CSF_1R$ inhibitors (Compound 6 and Compound 24) significantly mean disease scores. The deuterated $CSF_1R$ inhibitor, Compound 6, ameliorated paralytic symptoms to a surprisingly greater extent than nondeuterated Compound 24.
Figure 19B:
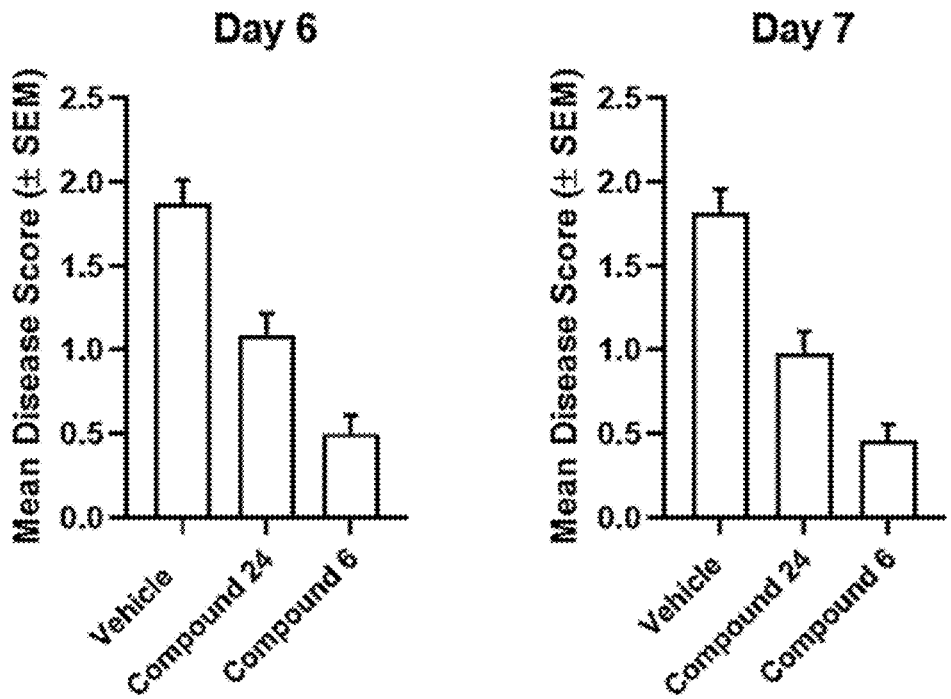

The protocol aimed to induce an EAE model with a higher concentration emulsion of MOG$_{35-55}$ and CFA. At a score of 1 or greater, EAE mice were randomized into three different treatment groups: vehicle, Compound 24 (15 mg/kg), or Compound 6 (15 mg/kg). Mean disease scores in this study (FIG. 19) demonstrate the standard disease course of the MOG$_{35-55}$-induced C57BL/6 EAE model of multiple sclerosis. Data points and error bars represent the group mean and the standard error of the mean respectively. As seen in FIG. 19, both CSF₁R inhibitors significantly mean disease scores. However, the deuterated CSF₁R inhibitor, Compound 6, ameliorated paralytic symptoms to a surprisingly greater extent than nondeuterated Compound 24.

What is claimed is:
1. A compound of Formula (I'):

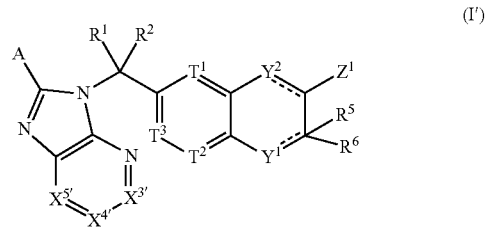

and/or stereoisomers, optical isomers, racemic and diastereomeric mixtures, and/or pharmaceutically acceptable salts thereof, wherein:

the dashed lines represent optional double bonds;

A is selected from H and D;

$X^{3'}$ is $CR^{3'}$ wherein $R^{3'}$ is selected from H and D;

$X^{4'}$ is $CR^{4'}$ wherein $R^{4'}$ is selected from H, and D;

$X^{5'}$ is $CR^{5'}$ wherein $R^{5'}$ is selected from H and D;

$T^1$, $T^2$, and $T^3$ are each independently selected from N or CR';

wherein each $R^{10}$ is independently selected from H, D, $(C_1-C_{10})$alkyl, $(C_3-C_{10})$cycloalkyl, $(C_1-C_{10})$alkylamine, $((C_1-C_{10})$alkyl)$_2$amine, $(C_2-C_{10})$alkynylamine, $(C_1-C_{10})$alkyl-C(O)O—, COOH—$(C_1-C_{10})$alkyl-, COOH—$(C_3-C_{10})$cycloalkyl-, $(C_1-C_{10})$alkoxy-, $R^{10A}$—$(C_1-C_{10})$alkyl-, $R^{10A}$—$(C_1-C_{10})$alkylamine, $R^{10A}$—$((C_1-C_{10})$alkyl)$_2$amine, $R^{10A}$—$(C_2-C_{10})$alkynylamine, $R^{10A}$—C(O)—, $R^{10A}$—$(C_1-C_{10})$alkyl-C(O)O—, $R^{10A}$—$(C_1-C_{10})$alkoxy-, HO—, and halo, cyano, $H_2N$—, $(CH_3)HN$—, $(CH_3)_2N$—, $R^{10A}R^{11}N$—, $R^{10A}R^{11}N(O)C$—, $R^{10A}(R^{11}C(O))N$—, $R^{10A}R^{11}NC(O)$ O—, $R^{10A}C(O)$—, $R^{10A}R^{11}NC(O)R^{10A}N$—, $(C_1-C_{10})$alkyl-OC(O)$R^{10A}N$—, $F_3C$—, $F_2HC$—, $CH_3F_2C$—, $FH_2C$—, $CH_3FHC$—, $(CH_3)_2FC$—;

wherein $R^{10A}$ and $R^{11}$ are each independently selected from H, D, $(C_1-C_{10})$alkyl, $(C_1-C_{10})$alkylamine, $((C_1-C_{10})$alkyl)$_2$amine, $(C_1-C_3)$alkynylamine, $(C_1-C_{10})$alkyl-C(O)O—, COOH—$(C_1-C_{10})$alkyl, $(C_1-C_{10})$alkoxy-, $(C_1-C_{10})$alkoxy-$(C_1-C_{10})$alkyl-, HO—, halo, $(CH_3)_2N$—, and $H_2N$—;

wherein each $(C_1-C_{10})$alkyl are further optionally substituted by one to four groups selected from D, $(C_1-C_{10})$alkyl, $(C_1-C_{10})$alkylamine, $((C_1-C_{10})$alkyl)$_2$amine, $(C_1-C_{10})$alkoxy-, $(C_1-C_{10})$alkoxy-$(C_1-C_{10})$alkyl-, HO—, halo, or $H_2N$—

$Y^1$ is O, $NR^{12}$, or $CR^{12}R^{13}$, wherein $R^{12}$ is absent or $R^{12}$ and $R^{13}$ are each independently selected from H, D, $(C_1-C_{10})$alkyl, $(C_1-C_{10})$alkylamine, $((C_1-C_{10})$alkyl)$_2$amine, $(C_1-C_3)$alkynylamine, $(C_1-C_{10})$alkoxy-, $(C_1-C_{10})$alkoxy-$(C_1-C_{10})$alkyl-, HO—, halo, and $H_2N$—;

$R^1$ and $R^2$ are each independently selected from H, D, $(C_1-C_{10})$alkyl, HO—, halo, and $H_2N$;

$R^5$ is absent or selected from the group H, D, $(C_1-C_{10})$alkyl, HO—, halo, and $H_2N$—; and $R^6$ is selected from the group D, $(C_1-C_{10})$alkyl, $(C_3-C_{10})$cycloalkyl, $(C_2-C_9)$heteroaryl, $(C_1-C_{10})$alkylamine, $((C_1-C_{10})$alkyl)$_2$amine, $R^{14}$-$(C_3-C_{10})$cycloalkyl, $R^{14}$-$(C_6-C_{14})$aryl, $R^{14}$-$(C_2-C_9)$heteroaryl, and $R^{14}$-$(C_1-C_{10})$alkylamine;

wherein $R^{14}$ is each independently selected from H, D, $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, $((C_1-C_{10})$alkyl$)_2$amine, $(C_1-C_{10})$alkoxy-, HO—, $F_2$HC—O—, halo, $(CH_3)_2$N—, $F_3$C—C(O)—, $F_3$C—, and $F_2$HC—;
  wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, $(C_3-C_{10})$cycloalkyl, $(C_2-C_9)$heterocycloalkyl, $(C_6-C_{14})$aryl, $(C_2-C_9)$heteroaryl, HO—, halo, or $H_2$N—; and $Z^1$ is selected from H, halo, and $(C_1-C_{10})$alkyl;

$Y^2$ is O, $NR^{17}$, or $CR^{17}R^{18}$;
  wherein $R^{17}$ is absent or $R^{17}$ and $R^{18}$ are each independently selected from H, $(C_1-C_{10})$alkyl, HO—, halo, or $H_2$N—;

wherein at least one of A, $R^{3'}$, $R^{4'}$, and $R^{5'}$ is D.

2. The compound of claim 1, wherein $T^1$, $T^2$, and $T^3$ are each independently $CR^{10}$.

3. The compound of claim 1, wherein each $R^{10}$ is independently selected from H, $(C_1-C_{10})$alkyl, $(C_3-C_{10})$cycloalkyl, $(C_1-C_{10})$alkoxy, and halo.

4. The compound of claim 1, wherein $Y^1$ and $Y^2$ are each O.

5. The compound of claim 1, wherein $Z^1$ is selected from H and $(C_1-C_{10})$alkyl.

6. The compound of claim 1, wherein $R^1$ and $R^2$ are each independently selected from H and D.

7. The compound of claim 1, wherein $R^6$ is selected from $(C_3-C_{10})$cycloalkyl, $(C_2-C_9)$heteroaryl, $R^{14}$-$(C_2-C_2)$heteroaryl, and $R^{14}$-$(C_1-C_{10})$alkylamine; wherein $R^{14}$ is each independently selected from the group consisting of H, $(C_1-C_{10})$alkyl, $(C_1-C_{10})$alkylamine, $(C_1-C_{10})$alkoxy-, HO—, $F_2$HC—O—, $F_3$C—C(O)—, $F_3$C—, and $F_2$HC—;
  and wherein each $(C_1-C_{10})$alkyl, $(C_6-C_{14})$aryl, $(C_2-C_9)$heteroaryl, $(C_3-C_{10})$cycloalkyl, or $(C_2-C_9)$heterocycloalkyl are further optionally substituted by one to four groups selected from $(C_1-C_{10})$alkyl, HO—, halo, or $H_2$N—.

8. The compound of claim 1, wherein:
$T^1$, $T^2$, and $T^3$ are each independently $CR^{10}$;
each $R^{10}$ is independently selected from H and $(C_1-C_{10})$alkoxy-;
$Y^1$ and $Y^2$ are each O;
$Z^1$ is $(C_1C_{10})$alkyl;
$R^6$ is $R^{14}$-$(C_2-C_9)$heteroaryl; and
$R^{14}$ is $(C_1-C_{10})$alkoxy-.

9. The compound of claim 8, wherein:
$T^1$, $T^2$, and $T^3$ are each independently $CR^{10}$;
each $R^{10}$ is independently selected from H and $(C_1-C_{10})$alkoxy-;
$Y^1$ and $Y^2$ are each O;
$Z^1$ is $(C_1-C_{10})$alkyl; and
$R^6$ is a $C_5$heteroaryl substituted with a $C_1$alkoxy group.

10. A compound selected from:

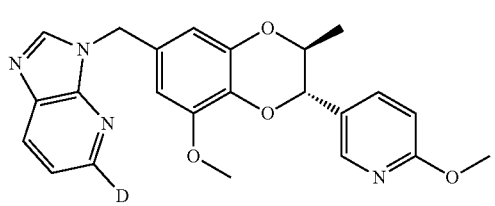

(+/-)-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-5-d

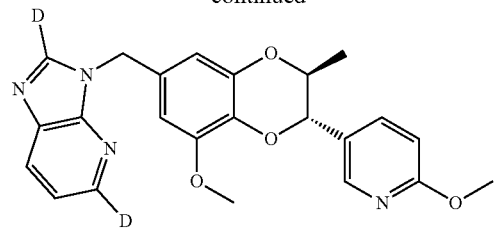

(+/-)-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-2,5-d2

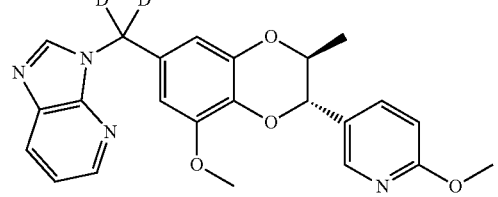

(+/-)-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine

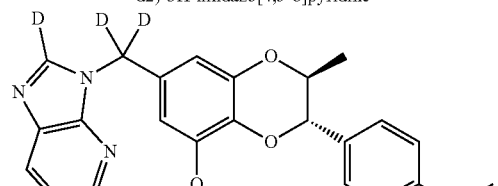

(+/-)-3-(((trans)-8-methoxy-2-(6-methoxypyridin-3-yl)-3-methyl-2,3-dihydrobenzo[b][1,4]dioxin-6-yl)methyl-d2)-3H-imidazo[4,5-b]pyridine-2-d

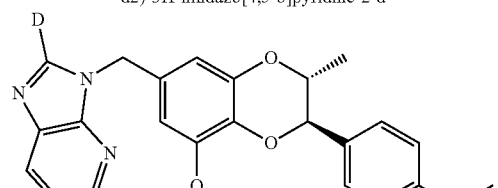

(+/-)-3-(((trans)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d

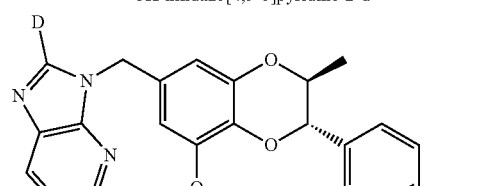

3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d and/or stereoisomers, optical isomers, racemic and diastereomeric mixtures, and/or pharmaceutically acceptable salts thereof.

11. A compound selected from 3-(((2S,3S)-8-methoxy-2-(6-methoxypyridin-3-yl)-3-methyl-2,3-dihydrobenzo[b][1, 4]dioxin-6-yl)methyl)-3H-imidazo[4,5-b]pyridine-2-d and/or stereoisomers, optical isomers, racemic and diastereomeric mixtures, and/or pharmaceutically acceptable salts thereof.

12. The compound of claim 11, which is 3-(((2S,3S)-8-methoxy-2-(6-methoxypyridin-3-yl)-3-methyl-2,3-dihydrobenzo[b] [1,4] dioxin-6-yl)methyl)-3H-imidazo[4,5-b]pyridine-2-d.

13. A pharmaceutical composition comprising a pharmaceutically acceptable excipient and a compound of claim 1 and/or a pharmaceutically acceptable salt thereof.

14. A pharmaceutical composition comprising a pharmaceutically acceptable excipient and a compound of claim 10 and/or a pharmaceutically acceptable salt thereof.

15. A method for treating an immune-mediated disease in a subject in need thereof comprising administering a compound according to claim 1 to the subject in a therapeutically effective amount.

16. A method for treating multiple sclerosis in a subject in need thereof comprising administering a compound according to claim 1 to the subject in a therapeutically effective amount.

17. A method for treating lupus nephritis in a subject in need thereof comprising administering a compound according to claim 1 to the subject in a therapeutically effective amount.

18. A method for treating a neurological disease in a subject in need thereof comprising administering a compound of claim 1 to the subject in a therapeutically effective amount.

19. The method of claim 18, wherein the neurological disease is amyotrophic lateral sclerosis (ALS).

20. The method of claim 18, wherein the neurological disease is progressive supranuclear palsy (PSP).

21. The method of claim 18, wherein the neurological disease is multiple system atrophy (MSA).

22. A solid form of 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d, characterized as Form A.

23. The solid form of claim 22, wherein 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d Form A is highly crystalline.

24. The solid form of claim 22, wherein 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d Form A has an X-ray powder diffraction pattern derived using Cu (Ka) radiation comprising three, four, five, six, or more peaks, in term of 2-theta degrees, chosen from: 7.6, 11.9, 16.6, 17.2, 18.6, 19.6, 22.4±0.2 degrees.

25. The solid form of claim 22, wherein 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d Form A has an X-ray powder diffraction pattern that is substantially in accordance with that shown in FIG. 20.

26. The solid form of claim 22, wherein 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d Form A is characterized by a differential scanning calorimetry (DSC) curve with an onset at about 159.25° C. and an endothermic peak at 163.78° C.

27. The solid form of claim 22, wherein 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d Form A is characterized by a Thermogravimetric Analysis (TGA) profile with negligible weight loss before 150° C.

28. The solid form of claim 22, wherein 3-(((2S,3S)-8-methoxy-2-(6-methoxypyridin-3-yl)-3-methyl-2,3-dihydrobenzo[b][1,4]dioxin-6-yl)methyl)-3H-imidazo[4,5-b]pyridine-2-d Form A is characterized by a DCS/TGA profile substantially in accordance with that shown in FIG. 22.

* * * * *

UNITED STATES PATENT AND TRADEMARK OFFICE
CERTIFICATE OF CORRECTION

PATENT NO.         : 11,530,216 B2
APPLICATION NO.    : 17/669950
DATED              : December 20, 2022
INVENTOR(S)        : John L. Kane, Jr., Nellwyn A. Hagan and Maria A. Fitzgerald Page 1 of 1

It is certified that error appears in the above-identified patent and that said Letters Patent is hereby corrected as shown below:

In the Claims

1. In Claim 1, Column 68, Line 25, "CR';", should be -- CR10; --

2. In Claim 7, Column 69, Line 29, "(C3-C10)cycloalkyl, (C2-C9)heteroaryl, R14-(C2-C2)heteroaryl,", should be -- (C3-C10)cycloalkyl, (C2-C9)heteroaryl, R14-(C6-C14)aryl, R14-(C2-C9)heteroaryl, --

3. In Claim 8, Column 69, Line 43, "Z1 is (C1C10)alkyl;", should be -- Z1 is (C1-C10)alkyl; --

4. In Claim 8, Column 69, Line 45, "R14 is (Ci-C10)alkoxy-", should be
-- R14 is (C1-C10)alkoxy-. --

5. In Claim 10, Column 70, Line 45, "(+/-)-3-(((trans)", should be -- 3-(((2R,3R)-8-methoxy-2-(6- --

6. In Claim 24, Column 72, Line 13, "derived using Cu (Ka) radiation comprising three, four, five,", should be -- derived using Cu (Kα) radiation comprising three, four, five, --

Signed and Sealed this
Nineteenth Day of September, 2023

Katherine Kelly Vidal
*Director of the United States Patent and Trademark Office*